United States Patent
Pearlman et al.

(10) Patent No.: US 7,112,670 B2
(45) Date of Patent: Sep. 26, 2006

(54) CRYSTAL FORM

(75) Inventors: Bruce Allen Pearlman, Kalamazoo, MI (US); Frederick J. Antosz, Kalamazoo, MI (US)

(73) Assignee: Pharmacia Corporation, Chesterfield, MO (US)

( * ) Notice: Subject to any disclaimer, the term of this patent is extended or adjusted under 35 U.S.C. 154(b) by 0 days.

(21) Appl. No.: 10/666,175

(22) Filed: Sep. 19, 2003

(65) Prior Publication Data

US 2004/0127702 A1 Jul. 1, 2004

Related U.S. Application Data

(63) Continuation-in-part of application No. 10/392,833, filed on Mar. 21, 2003.

(60) Provisional application No. 60/425,596, filed on Nov. 12, 2002, provisional application No. 60/411,874, filed on Sep. 19, 2002.

(51) Int. Cl.
- C07J 21/00 (2006.01)
- C07J 53/00 (2006.01)
- A61K 31/585 (2006.01)

(52) U.S. Cl. .............. 540/41; 540/43; 552/502; 552/508; 552/638; 514/175

(58) Field of Classification Search .......... 540/41, 540/43; 552/502, 508, 638; 514/175, 951
See application file for complete search history.

(56) References Cited

U.S. PATENT DOCUMENTS

| | | | |
|---|---|---|---|
| 3,565,924 A | 2/1971 | De Luca et al. | 260/397.2 |
| 3,833,622 A | 9/1974 | Babcock et al. | 260/397.2 |
| 4,504,657 A | 3/1985 | Bouzard et al. | 544/30 |
| 4,521,431 A | 6/1985 | Crookes | 514/471 |
| 4,559,332 A | 12/1985 | Grob et al. | |
| 5,773,610 A * | 6/1998 | McWhorter et al. | 540/200 |
| 5,962,697 A * | 10/1999 | Fleck et al. | 548/566 |
| 5,981,744 A * | 11/1999 | Ng et al. | 540/41 |
| 6,180,780 B1 * | 1/2001 | Ng et al. | 540/43 |
| 6,335,441 B1 * | 1/2002 | Ng et al. | 540/23 |
| 6,410,054 B1 * | 6/2002 | Thosar et al. | 424/489 |
| 6,444,813 B1 | 9/2002 | Bergren | 544/137 |
| 6,495,165 B1 * | 12/2002 | Thosar et al. | 424/489 |
| 6,592,902 B1 * | 7/2003 | Thosar et al. | 424/489 |
| 6,610,844 B1 * | 8/2003 | Ng et al. | 540/41 |
| 6,630,587 B1 * | 10/2003 | Ng et al. | 540/41 |
| 6,638,937 B1 * | 10/2003 | Murugesan et al. | 514/255.05 |
| 6,716,829 B1 * | 4/2004 | Rocha et al. | 514/171 |
| 2004/0097475 A1 * | 5/2004 | Wuts | 514/173 |

FOREIGN PATENT DOCUMENTS

| | | |
|---|---|---|
| WO | WO 97/21720 | 6/1997 |
| WO | WO 98/25948 | 6/1998 |
| WO | WO 01/41535 A2 * | 6/2001 |
| WO | WO0141535 | 6/2001 |
| WO | WO0142272 | 6/2001 |
| WO | WO 03/082894 A2 | 10/2003 |

* cited by examiner

*Primary Examiner*—Sabiha N. Qazi
(74) *Attorney, Agent, or Firm*—R. Steve Thomas; Charles Ashbrook

(57) ABSTRACT

The present invention involves a novel crystal form of 17β-hydroxy-7α-(5'-methyl-2'-furyl)-pregna-4,9(11)-dien-3-one-21-carboxylic acid, γ-lactone, having the formula

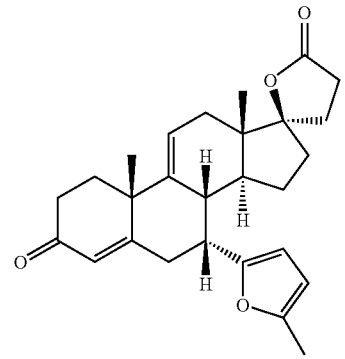

which is an intermediate useful in preparation of an important pharmaceutical, eplerenone.

8 Claims, No Drawings

CRYSTAL FORM

CROSS-REFERENCE TO RELATED APPLICATIONS

This application is a continuation-in-part of application Ser. No. 10/392,833, filed Mar. 21, 2003, which claims the priority benefit of U.S. Provisional Patent Application Ser. No. 60/411,874 filed Sep. 19, 2002 and U.S. Provisional Patent Application Ser. No. 60/425,596 filed Nov. 12, 2002.

BACKGROUND OF THE INVENTION

1. Field of the Invention

The present invention is a novel crystal form of 17β-hydroxy-7α-(5'-methyl-2'-furyl)-pregna-4,9(11)-dien-3-one-21-carboxylic acid, γ-lactone.

The present invention includes a process for the transformation of a 3-enol ether $\Delta^{3,5}$-steroid to the corresponding $\Delta^{4,6}$-3-ketal steroid (I-P).

The present invention includes a process for the transformation of a $\Delta^{4,6}$-3-keto steroid or ketal thereof (I), to the corresponding $\Delta^{4}$-3-ketosteroid-7α-carboxylic acid (VI).

The present invention also includes a novel processes and novel intermediates to produce the pharmaceutically useful compound eplerenone.

Further, the invention includes processes for transformation of 11α-hydroxy-17-lactone (CI) or 11α-hydroxy steroids (CIV) to the corresponding $\Delta^{9(11)}$-17-lactone (CII) or $\Delta^{9(11)}$-steroids (CV) using a N-fluoroalkylamine reagents (CVI).

2. Description of the Related Art

There is no reliable method to predict the existence of a crystal form of a pharmaceutical. Further, if a material is crystalline there is no reliable method to predict its physical properties. Therefore, patents to novel crystal forms are well known. For example, U.S. Pat. No. 3,565,924 discloses and claims 25-hydroxycocalciferol (25-HCC) which is a non-crysalline solid. Later a novel crystal form, 25-HCC hemihydrate was patented, see U.S. Pat. No. 3,833,622. U.S. Pat. No. 4,521,431 discloses crystal forms 1 and 2 of ranitidine hydrochloride. U.S. Pat. No. 4,504,657 claims "crystalline 7-[D-.alpha.-(p-hydroxyphenyl)acetamido]-3-methyl-3-cephem-4-carboxylic acid monohydrate. U.S. Pat. No. 6,452,007 B1 claims the "S" and "T" crystal forms of 1-[5-methanesulfonamidoindolyl-2-carbonyl]4-[3-(1-methylethylamino)-2-pyridinyl]piperazine. U.S. Pat. No. 6,444,813 B2 claims a novel crystal form of a known antibacterial agent, linezolid.

International Publications WO01/41535 and WO01/42272 disclose crystal forms of pharmaceutical agent eplerenone.

SUMMARY OF INVENTION

Disclosed is a process for the preparation of a $\Delta^{4,6}$-ketal of formula (I-P)

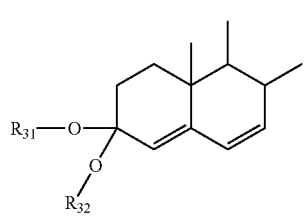

(I-P)

where $R_{31}$ and $R_{32}$ are
(1) the same or different and are $C_1$–$C_3$ alkyl, and
(2) taken with the attached —O—C—O— to form a cyclic ketal of 5 or 6 atoms of the formula —(CH$_2$)—(CR$_{33}$R$_{34}$)$_{n1}$—(CH$_2$)— where n, is 0 or 1;
where $R_{33}$ and $R_{34}$ are the same or different and are
—H,
$C_1$–$C_3$ alkyl, which comprises
(1) contacting a $\Delta^{3,5}$-3-enol ether of formula (Alkyl enol ether)

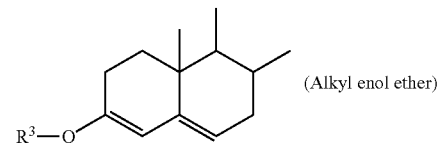

(Alkyl enol ether)

where $R^3$ is
$C_1$$C_3$ alkyl,
$CH_3$—CO—,
Φ-CO— or
$R_{Si-1}R_{Si-2}R_{Si-3}$Si— where $R_{Si-1}$, $R_{Si-2}$ and $R_{Si-3}$ are the same or different and are $C_1$–$C_4$ alkyl; with a hydride abstractor and an alcohol selected from the group consisting of alcohols of the formula:
(a) $R_{31}$—OH, where $R_{31}$ is as defined above,
(b) $R_{32}$—OH, where $R_{32}$ is as defined above,
(c) HO—(CH$_2$)—(CR$_{33}$R$_{34}$)$_{n1}$—(CH$_2$)—OH where $n_1$, $R_{33}$ and $R_{34}$ are as defined above,
(d) HO—CH$_2$—CH$_2$—OH.

Also disclosed is a 7α-substituted steroid of formula (II)

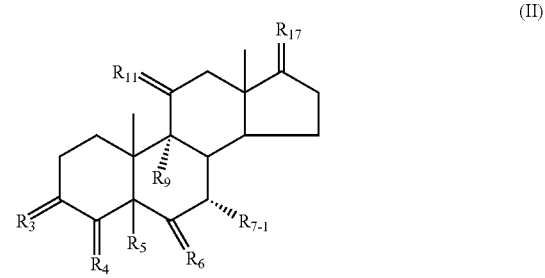

(II)

where
(I) $R_3$ is =O; $R_4$ is $R_{4-1}$:$R_{4-2}$ where one of $R_{4-1}$ and $R_{4-2}$ is —H and the other of $R_{4-1}$ and $R_{4-2}$ is taken together with $R_5$ to form a second bond between the carbon atoms to which they are attached; $R_6$ is —H:—H;
(II) $R_3$ is $R_{3-3}$:$R_{3-4}$ and $R_4$ is $R_{4-3}$:$R_{4-4}$ where one of $R_{3-3}$ and $R_{3-4}$ is —O—$R_{31}$ where $R_{31}$ is $C_1$–$C_3$ alkyl, the other of $R_{3-3}$ and $R_{3-4}$ is taken together with one of $R_{4-3}$ and $R_{4-4}$ to form a second bond between the carbon atoms to which they are attached, and the other of $R_{4-3}$ and $R_{4-4}$ is —H; $R_6$ is $R_{6-3}$:$R_{6-4}$ where one of $R_{6-3}$ and $R_{6-4}$ is taken together with $R_5$ to form a second bond between the carbon atoms to which they are attached and the other of $R_{6-3}$ and $R_{6-4}$ is —H;

(III) $R_3$ is $\alpha$-$R_{3-5}$:$\beta$-$R_{3-6}$ where $R_{3-5}$ is —O—$R_{31}$ and $R_{3-6}$ is —O—$R_{32}$ where $R_{31}$ and $R_{32}$ are the same or different and are selected from the group consisting of $C_1$–$C_3$ alkyl and $R_{31}$ and $R_{32}$ are taken with the attached —O—C—O— to form a cyclic ketal of 5 or 6 atoms of the formula

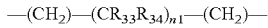

where $n_1$ is 0 or 1;

where $R_{33}$ and $R_{34}$ are the same or different and are —H and $C_1$–$C_3$ alkyl; $R_4$ is —H:—H; $R_6$ is $R_{6-5}$:$R_{6-6}$ where one of $R_{6-5}$ and $R_{6-6}$ is taken together with $R_5$ to form a second bond between the carbon atoms to which they are attached and the other of $R_{6-5}$ and $R_{6-6}$ is —H;

(IV) $R_3$ is $\alpha$-$R_{3-7}$:$\beta$-$R_{3-8}$ where $R_{3-7}$ is —O—$R_{31}$ and $R_{3-8}$ is —O—$R_{32}$ where $R_{31}$ and $R_{32}$ are as defined above; $R_4$ is $R_{4-7}$:$R_{4-8}$ where one of $R_{4-7}$ and $R_{4-8}$ is taken together with $R_5$ to form a second bond between the carbon atoms to which they are attached and the other of $R_{4-7}$ and $R_{4-8}$ is —H; $R_6$ is —H:—H;

where $R_{7-1}$ is a molecular fragment of the formula (-A1)

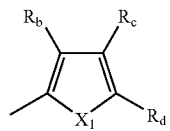

or of the formula (-A2)

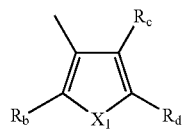

where $X_1$ is:
—S—,
—O— or
—N$X_{1-1}$— and where $X_{1-1}$ is:
—H,
$C_1$–$C_4$ alkyl,
—CO—O$X_{1-2}$ where $X_{1-2}$ is $C_1$–$C_4$ alkyl or —$CH_2$-$\Phi$,
—CO—$X_{1-2}$ where $X_{1-2}$ is as defined above,
—CO-$\Phi$ where -$\Phi$ is substituted in the o-position with —CO—O—($C_1$–$C_4$ alkyl),
—$SO_2$—($C_1$–$C_3$ alkyl),
—$SO_2$-$\Phi$ where $\Phi$ is optionally substituted with 1 or 2
$C_1$–$C_4$ alkyl,
$C_1$–$C_4$ alkoxy;
where $R_b$ is selected from the group consisting of
—H,
$C_1$–$C_4$ alkyl or
phenyl optionally substituted with 1 or 2
$C_1$–$C_4$ alkyl,
$C_1$–$C_4$ alkoxy,
where $R_c$ is selected from the group consisting of:
—H,
$C_1$–$C_4$ alkyl,
$C_1$–$C_4$ alkoxy,
—O—Si(R)$_3$ where the R's are the same or different and are —H, $C_1$–$C_4$ alkyl, -$\Phi$, $C_1$–$C_4$ alkoxy and —OH,
—F, —Cl, —Br, —I,
—CO—$OCH_3$ and
—CO—$R_{c-1}$ where $R_{c-1}$ is $C_1$–$C_4$ alkyl or -$\Phi$;
where $R_d$ is selected from the group consisting of
—H,
—C≡N,
$C_1$–$C_{10}$ alkyl;
$C_1$–$C_4$ alkoxy;
—$CH_2$—O$R_{d-1}$ where $R_{d-1}$ is —H or $C_1$–$C_4$ alkyl,
—$CH_2$—N($R_{d-6}$)$_2$ where the two $R_{d-6}$ are the same or different and are:
$C_1$–$C_4$ alkyl,
-$\Phi$,
—CO—$R_{d-6a}$ where $R_{d-6a}$ is $C_1$–$C_4$ alkyl or -$\Phi$,
—$CH_2$—O—CO—$R_{d-1}$ where $R_{d-1}$ is as defined above,
—CH(O$R_{d-1}$)$_2$ where $R_{d-1}$ is as defined above and where the two $R_{d-1}$ taken together are:
—$CH_2$—$CH_2$—,
—$CH_2$—$CH_2$—$CH_2$—,
—$CH_2$—C($CH_3$—)$_2$—$CH_2$—,
—CH(—O—CO—$R_{d-1}$)$_2$ where $R_{d-1}$ is as defined above,
—Si(R)$_3$ where R is as defined above,
—O—Si(R)$_3$ where R is as defined above,
—Sn($R_{b-1}$)$_3$ where $R_{b-1}$ is as defined above,
—S—$R_{d-5}$ where $R_{d-5}$ is $C_1$–$C_4$ alkyl or -$\Phi$,
—N($R_{d-6}$)$_2$ where $R_{d-6}$ is as defined above, where $R_c$ and $R_d$ taken together with the atoms to which they are attached to form where $E_1$ are the same or different and are:
—H,
$C_1$–$C_4$ alkyl,
—F, —Cl, —Br, —I,
—O$E_{1-1}$ where $E_{1-1}$ is:
—H,
$C_1$–$C_4$ alkyl,
-$\Phi$ or
—Si$E_{1-2}E_{1-3}E_{1-4}$ where $E_{1-2}$, $E_{1-3}$ and $E_{1-4}$ are the same or different and are $C_1$–$C_4$ alkyl or $C_1$–$C_4$ alkoxy,
—S—$E_{1-5}$ where $E_{1-5}$ is $C_1$–$C_4$ alkyl or -$\Phi$,
—S—(O)$_{1-2}$-$E_{1-5}$ where $E_{1-5}$ is as defined above,
—N($R_{d-6}$)$_2$ where the two $R_{d-6}$ are the same or different and are as defined above,
—P(O)(O—$E_{1-1}$)$_2$ where $E_{1-1}$ is as defined above,
—Si(R)$_3$ where R is as defined above;

$$—CE_1=M \qquad (-B)$$

where $E_1$ is as defined above and
where M is:
(1) =O,
(2) =N—$E_2$ where $E_2$ is selected from the group consisting of —H
$C_1$–$C_4$ alkyl,
$C_1$–$C_4$ alkenyl containing 1 or 2 double bonds,
$C_1$–$C_4$ alkynyl containing 1 triple bond,
—CO—O$E_{2-1}$ where $E_{2-1}$ is —H or $C_1$–$C_4$ alkyl, —C(E$_{2-1}$)$_2$—OE$_{2-2}$ where E$_{2-1}$ are the same or different and are as defined above and where E$_{2-2}$ is
C$_1$–C$_4$ alkyl,
-Φ or
—Si(R)$_3$ where the three R are the same or different and are defined above,
—OE$_{2-2}$ where E$_{2-2}$ is as defined above,
—S—E$_{2-3}$ where E$_{2-3}$ is C$_1$–C$_4$ alkyl or -Φ,
—S—(O)$_{1-2}$-E$_{2-3}$ where E$_{2-3}$ is as defined above,
—N(R$_{d-6}$)$_2$ where the two R$_{d6}$ are the same or different and are as defined above;
—Si(R)$_3$ where the three R are as defined above;
(3) =C(E$_2$)$_2$ where the E$_2$ are the same or different and are as defined above,
where E$_1$ and E$_2$ are taken together with the atoms to which they are attached to form a ring of 5 thru 7 members, optionally containing 3 thru 5
—O—,
—S—,
—N=,
—NX$_{1-1}$— where X$_{1-1}$ is as defined above,
—CE$_2$= where E$_2$ is as defined above,
—C(R$_b$)$_2$— where R$_b$ is as defined above, and optionally containing 1 or 2 additional double bonds;

—C≡C—E$_2$ (-C)

where E$_2$ is as defined above;

—CH$_2$—CH=CH$_2$ (-D1)

—CH=C=CH$_2$ (-D2)

—CH$_2$—C≡C—H (-D3)

where R$_9$ is:
(1) —H,
(2) —OH,
(3) —O-(HYDROXY PROTECTING GROUP) where HYDROXY PROTECTING GROUP is selected from the group consisting of
—Si(—CH$_3$)$_3$,
—Si(—CH$_2$—CH$_3$)$_3$,
—CO—CH$_3$,
—CO—H and
—SiH(CH$_3$)$_2$,
(4) —F;
where R$_{11}$ is:
(1) =O,
(2) —H:—H,
(3) α-R$_{11-1}$:β-R$_{11-2}$ where R$_{11-1}$ is:
  (a) —H,
  (b) —O—R$_{11-3}$ where R$_{11-3}$ is:
    (i) —H,
    (ii) a HYDROXY PROTECTING GROUP) where HYDROXY PROTECTING GROUP is as defined above, and where R$_{11-2}$ is:
  (a) —H,
  (b) —O—R$_{11-4}$ where R$_{11-4}$ is:
    (i) —H,
    (ii) a HYDROXY PROTECTING GROUP) where HYDROXY PROTECTING GROUP is as defined above, with the proviso that one of R$_{11-1}$ and R$_{11-2}$ must be —H,
(4) R$_{11-5}$:R$_{11-6}$ where one of R$_{11-5}$ or R$_{11-6}$ and R$_9$ are taken together with R$_9$ to form a second bond between C-9 and C-11 and the other of R$_{11-5}$ or R$_{11-6}$ is —H,
(5) α-R$_{11-7}$:β-R$_{11-8}$ where R$_{11-7}$ and R$_9$ are taken together with —O— to form an epoxide between C-9 and C-11 and R$_{11-8}$ is —H;
where R$_{17}$ is:
(1) =O;
(2) α-R$_{17-1}$:β-R$_{17-2}$ where R$_{17-1}$ is:
  (a) —H,
  (b) —C≡C—H,
  (c) —C≡N,
  (d) —C≡C—CH$_2$—O—R$_{17-1-1}$ where R$_{17-1-1}$ is selected from the group consisting of
    (i) —H,
    (ii) —Si(R$_{17-1-2}$)$_3$ where R$_{17-1-2}$ are the same or different and are C$_1$–C$_4$ alkyl,
    (iii) 1-ethoxyethyl,
    (iv) 2-tetrahydropyranyl,
  (e) —C≡C—CH$_2$—O-(HYDROXY PROTECTING GROUP), where HYDROXY PROTECTING GROUP is as defined above,
  (f) —CH$_2$—CH$_2$—CH$_2$—OH,
  (g) —CH$_2$—CH$_2$—CH$_2$—O-(HYDROXY PROTECTING GROUP), where HYDROXY PROTECTING GROUP is as defined above,
  (h) —CH$_2$—CH$_2$—CO—O$^-$ and where R$_{17-2}$ is —OH;
(3) α-R$_{17-3}$:β-R$_{17-4}$ where R$_{17-3}$ is —OH and where R$_{17-4}$ is:
  (a) —CO—CH$_3$,
  (b) —CO—CH$_2$—OH,
  (c) —CO—CH$_2$—O—CO—(CH$_2$)$_{0-3}$—CH$_3$;
(4) α-R$_{17-5}$:β-R$_{17-6}$ where R$_{17-5}$ and R$_{17-6}$ are taken with the attached carbon atom to form a three member epoxide containing —O—CH$_2$— where the attachment of the —O is at R$_{17-6}$ in the β-orientation and the attachment of the CH$_2$— is at R$_{17-5}$ in the α-orientation;
(5) α-R$_{17-7}$:β-R$_{17-8}$ where R$_{17-7}$ and R$_{17-8}$ are taken with the attached carbon atom to form a five member lactone containing —O—CO—CH$_2$—CH$_2$— where the attachment of the CH$_2$— is at R$_{17-7}$ in the α-orientation and the attachment of the —O is at R$_{17-8}$ in the β-orientation;
(6) —O—CH(OR$_{17-9}$)—CH$_2$—CH$_2$ . . . where the bond from the oxygen (—O) is one of the four bonds at C-17 in the β-configuration and the bond from the methylene group (CH$_2$ . . . ) is another of the four bonds at C-17 in the α-configuration to form a 5 member heterocycle containing one oxygen atom, where R$_{17-9}$ is —H or C$_1$–C$_3$ alkyl;
(7) α-R$_{17-11}$:β-R$_{17-12}$ where R$_{17-10}$ is —(CH$_2$)$_{1-2}$—CH=CH$_2$ and R$_{17-12}$ is —OH.

Further disclosed is a cis enedione of the formula (III-cis)

and a trans enedione of the formula (III-trans)

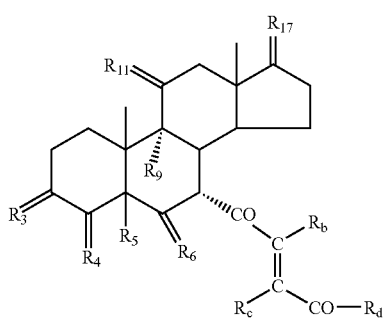

(III-trans)

where
(I) $R_3$ is =O; $R_4$ is $R_{4-1}$:$R_{4-2}$ where one of $R_{4-1}$ and $R_{4-2}$ is —H and the other of $R_{4-1}$ and $R_{4-2}$ is taken together with $R_5$ to form a second bond between the carbon atoms to which they are attached; $R_6$ is —H:—H;

(III) $R_3$ is α-$R_{3-5}$:β-$R_{3-6}$ where $R_{3-5}$ is —O—$R_{31}$ and $R_{3-6}$ is —O—$R_{32}$ where $R_{31}$ and $R_{32}$ are the same or different and are selected from the group consisting of
$C_1$–$C_3$ alkyl and
$R_{31}$ and $R_{32}$ are taken with the attached —O—C—O— to form a cyclic ketal of 5 or 6 atoms of the formula —(CH$_2$)—(CR$_{33}$R$_{34}$)$_{n1}$—(CH$_2$)— where $n_1$ is 0 or 1;
where $R_{33}$ and $R_{34}$ are the same or different and are —H and $C_1$–$C_3$ alkyl; $R_4$ is —H:—H; $R_6$ is $R_{6-5}$:$R_{6-6}$ where one of $R_{6-5}$ and $R_6$ is taken together with $R_5$ to form a second bond between the carbon atoms to which they are attached and the other of $R_{6-5}$ and $R_{6-6}$ is —H;

(IV) $R_3$ is α-$R_{3-7}$:β-$R_{3-8}$ where $R_{3-7}$ is —O—$R_{31}$ and $R_{3-8}$ is —O—$R_{32}$ where $R_{31}$ and $R_{32}$ are as defined above; $R_4$ is $R_{4-7}$:$R_{4-8}$ where one of $R_{4-7}$ and $R_{4-8}$ is taken together with $R_5$ to form a second bond between the carbon atoms to which they are attached and the other of $R_{4-7}$ and $R_{4-8}$ is —H; $R_6$ is —H:—H;
where $R_9$, $R_{11}$ $R_{17}$ are as defined above;
where $R_b$ is selected from the group consisting of
—H,
$C_1$–$C_4$ alkyl or
phenyl optionally substituted with 1 or 2
  $C_1$–$C_4$ alkyl,
  $C_1$–$C_4$ alkoxy,
where $R_c$ is selected from the group consisting of:
—H,
$C_1$–$C_4$ alkyl,
$C_1$–$C_4$ alkoxy,
—O—Si(R)$_3$ where the R's are the same or different and are —H, $C_1$–$C_4$ alkyl, -Φ, $C_1$–$C_4$ alkoxy and —OH,
—F, —Cl, —Br, —I,
—CO—OCH$_3$ and
—CO—$R_{c-1}$ where $R_{c-1}$ is $C_1$–$C_4$ alkyl or -Φ;
where $R_d$ is selected from the group consisting of
—H,
—C≡N,
$C_1$–$C_{10}$ alkyl;
$C_1$–$C_4$ alkoxy;
—CH$_2$—OR$_{d-1}$ where $R_{d-1}$ is —H or $C_1$–$C_4$ alkyl, —CH$_2$—N(R$_{d-6}$)$_2$ where the two R$_{d-6}$ are the same or different and are:
$C_1$–$C_4$ alkyl,
-Φ,
—CO—R$_{d-6a}$ where R$_{d-6a}$ is $C_1$–$C_4$ alkyl or -Φ,
—CH$_2$—O—CO—R$_{d-1}$ where R$_{d-1}$ is as defined above,
—CH(OR$_{d-1}$)$_2$ where R$_{d-1}$ is as defined above and where the two R$_{d-1}$ taken together are:
—CH$_2$—CH$_2$—,
—CH$_2$—CH$_2$—CH$_2$—,
—CH$_2$—C(CH$_3$—)$_2$—CH$_2$—,
—CH(—O—CO—R$_{d-1}$)$_2$ where R$_{d-1}$ is as defined above,
—Si(R)$_3$ where R is as defined above,
—O—Si(R)$_3$ where R is as defined above,
—Sn(R$_{b-1}$)$_3$ where R$_{b-1}$ is as defined above,
—S—R$_{d-5}$ where R$_{d-5}$ is $C_1$–$C_4$ alkyl or -Φ,
—N(R$_{d-6}$)$_2$ where R$_{d-6}$ is as defined above,
where $R_c$ and $R_d$ taken together with the atoms to which they are attached to form

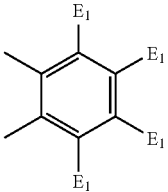

where $E_1$ are the same or different and are:
—H,
$C_1$–$C_4$ alkyl,
—F, —Cl, —Br, —I,
—OE$_{1-1}$ where E$_{1-1}$ is:
—H,
$C_1$–$C_4$ alkyl,
-Φ or
—SiE$_{1-2}$E$_{1-3}$E$_{1-4}$ where E$_{1-2}$, E$_{1-3}$ and E$_{1-4}$ are the same or different and are $C_1$–$C_4$ alkyl or $C_1$–$C_4$ alkoxy,
—S—E$_{1-5}$ where E$_{1-5}$ is $C_1$–$C_4$ alkyl or -Φ,
—S—(O)$_{1-2}$—E$_{1-5}$ where E$_{1-5}$ is as defined above,
—N(R$_{d-6}$)$_2$ where the two R$_{d-6}$ are the same or different and are as defined above,
—P(O)(O—E$_{1-1}$)$_2$ where E$_{1-1}$ is as defined above,
—Si(R)$_3$ where R is as defined above.

Disclosed is 17β-hydroxy-7α-(5'-methyl-2'-furyl)-pregna-4,9(11)-dien-3-one-21-carboxylic acid, γ-lactone a compound of the formula

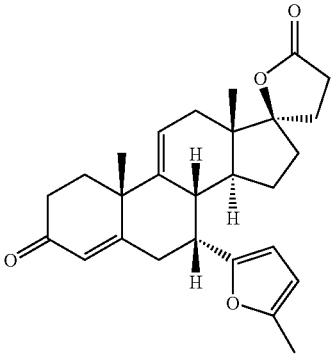

in crystalline form having a powder X-ray diffraction spectrum of:

Two-Theta Angle (°) with a range of

| From | To |
|---|---|
| 6.46 | 6.59 |
| 10.46 | 10.70 |
| 11.48 | 11.70 |
| 12.55 | 12.79 |
| 14.19 | 14.36 |
| 15.06 | 15.30 |
| 16.10 | 16.65 |
| 16.55 | 16.74 |
| 17.79 | 18.01 |
| 18.25 | 18.46 |
| 19.46 | 19.70 |
| 20.06 | 20.30 |
| 20.86 | 21.25 |
| 21.60 | 21.80 |
| 23.14 | 23.35 |
| 24.74 | 24.95 |
| 25.15 | 25.96 |
| 25.85 | 26.05 |
| 27.35 | 27.55 |
| 28.26 | 28.90 |
| 28.75 | 28.85 |
| 29.91 | 30.14 |
| 30.90 | 31.10 |
| 31.86 | 32.05 |
| 32.59 | 32.79 |
| 33.14 | 33.89 |
| 33.63 | 34.00 |
| 34.27 | 34.49 |
| 35.52 | 35.75 |
| 36.06 | 36.30 |
| 37.02 | 37.21 |
| 37.74 | 37.91 |
| 38.42 | 38.64 |
| 39.35 | 39.39 | to a reasonable degree of scientific certainty, where
Two-Theta Angle is measured in degrees.

Also disclosed is 17β-hydroxy-7α-(5'-methyl-2'-furyl)-pregna-4,9(11)-dien-3-one-21-carboxylic acid, γ-lactone in crystalline form having a powder X-ray diffraction spectrum of: Two-Theta Angle (°) and Relative Intensity (%) with a ranges of:

| Two-Theta Angle (°) | | Relative Intensity (%) | |
|---|---|---|---|
| From | To | From | To |
| 6.46 | 6.59 | 1.0 | 1.6 |
| 10.46 | 10.70 | 10.7 | 58.3 |
| 11.48 | 11.70 | 11.7 | 20.8 |
| 12.55 | 12.79 | 2.2 | 4.2 |
| 14.19 | 14.36 | 14.4 | 100.0 |
| 15.06 | 15.30 | 15.3 | 29.5 |
| 16.10 | 16.65 | 7.2 | 50.3 |
| 16.55 | 16.74 | 16.7 | 66.4 |
| 17.79 | 18.01 | 18.0 | 100.0 |
| 18.25 | 18.46 | 18.5 | 34.5 |
| 19.46 | 19.70 | 6.1 | 12.6 |
| 20.06 | 20.30 | 19.5 | 28.1 |
| 20.86 | 21.25 | 16.1 | 36.3 |
| 21.60 | 21.80 | 10.8 | 20.0 |
| 23.14 | 23.35 | 23.3 | 48.0 |
| 24.74 | 24.95 | 11.5 | 19.0 |
| 25.15 | 25.96 | 4.4 | 30.3 |
| 25.85 | 26.05 | 12.1 | 31.2 |
| 27.35 | 27.55 | 9.5 | 22.7 |
| 28.26 | 28.90 | 2.1 | 6.2 |
| 28.75 | 28.85 | 6.6 | 11.1 |
| 29.91 | 30.14 | 1.9 | 3.5 |
| 30.90 | 31.10 | 5.6 | 10.4 |
| 31.86 | 32.05 | 1.2 | 3.7 |
| 32.59 | 32.79 | 0.9 | 2.3 |
| 33.14 | 33.89 | 1.6 | 4.5 |
| 33.63 | 34.00 | 1.1 | 4.9 |
| 34.27 | 34.49 | 1.4 | 2.2 |
| 35.52 | 35.75 | 1.3 | 3.9 |
| 36.06 | 36.30 | 7.9 | 27.0 |
| 37.02 | 37.21 | 3.9 | 6.2 |
| 37.74 | 37.91 | 1.0 | 2.2 |
| 38.42 | 38.64 | 1.2 | 2.9 |
| 39.35 | 39.39 | 1.6 | 1.8 | to a reasonable degree of scientific certainty, where
Two-Theta Angle is measured in degrees and
Relative Intensity is the intensity percentage of each peak relative to the strongest peak.

Further disclosed is 17β-hydroxy-7α-(5'-methyl-2'-furyl)-pregna-4,9(11)-dien-3-one-21-carboxylic acid, γ-lactone in crystalline form having a powder X-ray diffraction spectrum of Two-Theta Angle (°), d-spacing (Å) and Relative Intensity (%) with ranges of:

| Two-Theta Angle (°) | | d-spacing (Å) | | Relative Intensity (%) | |
|---|---|---|---|---|---|
| From | To | From | To | From | To |
| 6.46 | 6.59 | 13.39 | 13.66 | 1.0 | 1.6 |
| 10.46 | 10.70 | 8.26 | 8.45 | 10.7 | 58.3 |
| 11.48 | 11.70 | 7.56 | 7.70 | 11.7 | 20.8 |
| 12.55 | 12.79 | 6.92 | 7.05 | 2.2 | 4.2 |
| 14.19 | 14.36 | 6.16 | 6.24 | 14.4 | 100.0 |
| 15.06 | 15.30 | 5.79 | 5.88 | 15.3 | 29.5 |
| 16.10 | 16.65 | 5.32 | 5.50 | 7.2 | 50.3 |
| 16.55 | 16.74 | 5.29 | 5.35 | 16.7 | 66.4 |
| 17.79 | 18.01 | 4.92 | 4.98 | 18.0 | 100.0 |
| 18.25 | 18.46 | 4.80 | 4.86 | 18.5 | 34.5 |
| 19.46 | 19.70 | 4.50 | 4.56 | 6.1 | 12.6 |
| 20.06 | 20.30 | 4.37 | 4.42 | 19.5 | 28.1 |
| 20.86 | 21.25 | 4.18 | 4.26 | 16.1 | 36.3 |
| 21.60 | 21.80 | 4.07 | 4.11 | 10.8 | 20.0 |
| 23.14 | 23.35 | 3.81 | 3.84 | 23.3 | 48.0 |
| 24.74 | 24.95 | 3.57 | 3.60 | 11.5 | 19.0 |
| 25.15 | 25.96 | 3.43 | 3.54 | 4.4 | 30.3 |
| 25.85 | 26.05 | 3.42 | 3.44 | 12.1 | 31.2 |
| 27.35 | 27.55 | 3.24. | 3.26 | 9.5 | 22.7 |
| 28.26 | 28.90 | 3.09 | 3.16 | 2.1 | 6.2 |
| 28.75 | 28.85 | 3.09 | 3.10 | 6.6 | 11.1 |
| 29.91 | 30.14 | 2.96 | 2.98 | 1.9 | 3.5 |
| 30.90 | 31.10 | 2.87 | 2.89 | 5.6 | 10.4 |
| 31.86 | 32.05 | 2.79 | 2.81 | 1.2 | 3.7 |
| 32.59 | 32.79 | 2.73 | 2.75 | 0.9 | 2.3 |
| 33.14 | 33.89 | 2.64 | 2.70 | 1.6 | 4.5 |
| 33.63 | 34.00 | 2.63 | 2.66 | 1.1 | 4.9 |
| 34.27 | 34.49 | 2.60 | 2.61 | 1.4 | 2.2 |
| 35.52 | 35.75 | 2.51 | 2.53 | 1.3 | 3.9 |
| 36.06 | 36.30 | 2.47 | 2.49 | 7.9 | 27.0 |
| 37.02 | 37.21 | 2.41 | 2.43 | 3.9 | 6.2 |
| 37.74 | 37.91 | 2.37 | 2.38 | 1.0 | 2.2 |
| 38.42 | 38.64 | 2.33 | 2.34 | 1.2 | 2.9 |
| 39.35 | 39.39 | 2.29 | 2.29 | 1.6 | 1.8 | to a reasonable degree of scientific certainty, where
Two-Theta Angle is measured in degrees,
d-Spacing is measured in angstroms, and
Relative Intensity is the intensity percentage of each peak relative to the strongest peak.

DETAILED DESCRIPTION OF THE INVENTION

Eplerenone is 9α,11α-epoxy-17β-hydroxypregn-4-en-3-one-7α,21-dicarboxylic acid, γ-lactone, methyl ester and as such contains a 7α-carbomethoxy substituent. It is useful as a pharmaceutical agent for the treatment of hypertension and congestive heart failure. A major difficulty in the production of eplerenone is introduction of the 7α-carbomethoxy substituent. The processes and intermediates of the present invention are improved processes for the preparation of eplerenone.

CHART A discloses the general process of the invention when the adduct at the 7α-position, —$R_{7-1}$ is (-A1). The process of the present invention begins with a protected or unprotected $\Delta^{4,6}$-3-keto steroid (I). Since the steroid A-ring can be protected or not protected, CHART B discloses an improved process for protection of the $\Delta^{4,6}$-3-keto steroid (I) starting material as a C-3 protected $\Delta^{4,6}$-3-ketal steroid (I-P). CHART C discloses an alternative route (ozonolysis) for transformation of the 7α-substituted steroid (II) to eplerenone (IX). CHART D discloses the general process when the steroid A-ring is unprotected and $R_{7-1}$ is the variable substituent (-A1). CHART E discloses the preferred process for the transformation of a $\Delta^{4,6}$-3-keto steroid or ketal thereof (I) to eplerenone (IX). CHART F discloses the reversible nature of the conversion of the carboxylic acid (VI) with the 5,7-lactone (VII). CHART G discloses the general process of the invention when —$R_{7-1}$ is (-A2). CHART H discloses the general process of the invention when —$R_{7-1}$ is (-B), (-C), (-D1), (-D2) or (-D3).

The first step in the process of CHART A is to prepare a 7α-substituted steroid (II) of the formula

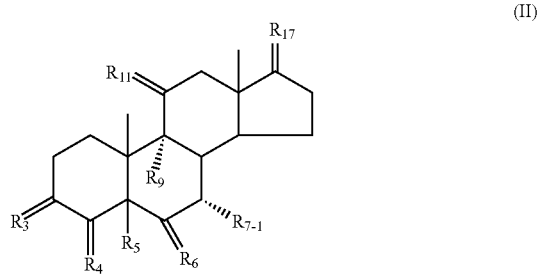

(II)

where (I) $R_3$ is =O; $R_4$ is $R_{4-1}$:$R_{4-2}$ where one of $R_{4-1}$ and $R_{4-2}$ is —H and the other of $R_{4-1\ and\ R4-2}$ is taken together with $R_5$ to form a second bond between the carbon atoms to which they are attached; $R_6$ is —H:—H;

(II) $R_3$ is $R_{3-3}$:$R_{3-4}$ and $R_4$ is $R_{4-3}$:$R_{4-4}$ where one of $R_{3-3}$ and $R_{3-4}$ is —O—$R_{31}$ where $R_{31}$ is $C_1$–$C_3$ alkyl, the other of $R_{3-3}$ and $R_{3-4}$ is taken together with one of $R_{4-3}$ and $R_{4-4}$ to form a second bond between the carbon atoms to which they are attached, and the other of $R_{4-3}$ and $R_{4-4}$ is —H; $R_6$ is $R_{6-3}$:$R_{6-4}$ where one of $R_{6-3}$ and $R_{6-4}$ is taken together with $R_5$ to form a second bond between the carbon atoms to which they are attached and the other of $R_{6-3}$ and $R_{6-4}$ is —H;

(III) $R_3$ is α-$R_{3-5}$:β-$R_{3-6}$ where $R_{3-5}$ is —O—$R_3$, and $R_{3-6}$ is —O—$R_{32}$ where $R_{31}$ and $R_{32}$ are the same or different and are selected from the group consisting of $C_1$–$C_3$ alkyl and $R_{31}$ and $R_{32}$ are taken with the attached —O—C—O— to form a cyclic ketal of 5 or 6 atoms of the formula

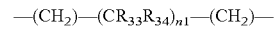

where $n_1$ is 0 or 1;

where $R_{33}$ and $R_{34}$ are the same or different and are —H and $C_1$–$C_3$ alkyl; $R_4$ is —H:—H; $R_6$ is $R_{6-5}$:$R_{6-6}$ where one of $R_{6-5}$ and $R_{6-6}$ is taken together with $R_5$ to form a second bond between the carbon atoms to which they are attached and the other of $R_{6-5}$ and $R_{6-6}$ is —H;

(IV) $R_3$ is α-$R_{3-7}$:β-$R_{3-8}$ where $R_{3-7}$ is —O—$R_{31}$ and $R_{3-8}$ is —O—$R_{32}$ where $R_{31}$ and $R_{32}$ are as defined above; $R_4$ is $R_{4-7}$:$R_{4-8}$ where one of $R_{4-7}$ and $R_{4-8}$ is taken together with $R_5$ to form a second bond between the carbon atoms to which they are attached and the other of $R_{4-7}$ and $R_{4-8}$ is —H; $R_6$ is —H:—H;

where $R_{7-1}$ is a molecular fragment of the formula (-A1)

(-A1)

or of the formula (-A2)

(-A2)

where $X_1$ is:
—S—,
—O— or
—N$X_{1-1}$— and where $X_{1-1}$ is:
—H,
$C_1$–$C_4$ alkyl,
—CO—O$X_{1-2}$ where $X_{1-2}$ is $C_1$–$C_4$ alkyl or —$CH_2$-Φ,
—CO—$X_{1-2}$ where $X_{1-2}$ is as defined above,
—CO-Φ where -Φ is substituted in the o-position with —CO—O—($C_1$–$C_4$ alkyl),
—$SO_2$—($C_1$–$C_3$ alkyl),
—$SO_2$-Φ where Φ is optionally substituted with 1 or 2 $C_1$–$C_4$ alkyl, $C_1$–$C_4$ alkoxy;
where $R_b$ is selected from the group consisting of
—H,
$C_1$–$C_4$ alkyl or
phenyl optionally substituted with 1 or 2
$C_1$–$C_4$ alkyl,
$C_1$–$C_4$ alkoxy,
where $R_c$ is selected from the group consisting of:
—H,
$C_1$–$C_4$ alkyl,
$C_1$–$C_4$ alkoxy,
—O—Si(R)$_3$ where the R's are the same or different and are —H, $C_1$–$C_4$ alkyl, -Φ, $C_1$–$C_4$ alkoxy and
—OH,
—F, —Cl, —Br, —I,
—CO—OCH$_3$ and
—CO—$R_{c-1}$ where $R_{c-1}$ is $C_1$–$C_4$ alkyl or -Φ;
where $R_d$ is selected from the group consisting of
—H,
—C≡N, $C_1$–$C_{10}$ alkyl;
$C_1$–$C_4$ alkoxy;
—$CH_2$—$OR_{d-1}$ where $R_{d-1}$ is —H or $C_1$–$C_4$ alkyl,
—$CH_2$—$N(R_{d-6})_2$ where the two $R_{d-6}$ are the same or different and are:
$C_1$–$C_4$ alkyl,
-Φ,
—CO—$R_{d-6a}$ where $R_{d-6a}$ is $C_1$–$C_4$ alkyl or -Φ,
—$CH_2$—O—CO—$R_{d-1}$ where $R_{d-1}$ is as defined above,
—$CH(OR_{d-1})_2$ where $R_{d-1}$ is as defined above and where the two $R_{d-1}$ taken together are:
—$CH_2$—$CH_2$—,
—$CH_2$—$CH_2$—$CH_2$—,
—$CH_2$—$C(CH_3)_2$—$CH_2$—,
—$CH(-O—CO—R_{d-1})_2$ where $R_{d-1}$ is as defined above,
—$Si(R)_3$ where R is as defined above,
—O—$Si(R)_3$ where R is as defined above,
—$Sn(R_{b-1})_3$ where $R_{b-1}$ is as defined above,
—S—$R_{d-5}$ where $R_{d-5}$ is $C_1$–$C_4$ alkyl or -Φ,
—$N(R_{d-6})_2$ where $R_{d-6}$ is as defined above,
where $R_c$ and $R_d$ taken together with the atoms to which they are attached to form

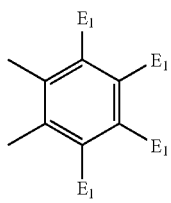

where $E_1$ are the same or different and are:
—H,
$C_1$–$C_4$ alkyl,
—F, —Cl, —Br, —I,
—$OE_{1-1}$ where $E_{1-1}$ is:
—H,
$C_1$–$C_4$ alkyl,
-Φ or
—$SiE_{1-2}E_{1-3}E_{1-4}$ where $E_{1-2}$, $E_{1-3}$ and $E_{1-4}$ are the same or different and are $C_1$–$C_4$ alkyl or $C_1$–$C_4$ alkoxy,
—S—$E_{1-5}$ where $E_{1-5}$ is $C_1$–$C_4$ alkyl or -Φ,
—S—$(O)_{1-2}$—$E_{1-5}$ where $E_{1-5}$ is as defined above,
—$N(R_{d-6})_2$ where the two $R_{d-6}$ are the same or different and are as defined above,
—P(O)(O—$E_{1-1})_2$ where $E_{1-1}$ is as defined above,
—$Si(R)_3$ where R is as defined above;

—$CE_1$=M     (-B)

where $E_1$ is as defined above and
where M is:
(1) =O,
(2) =N—$E_2$ where $E_2$ is selected from the group consisting of
—H
$C_1$–$C_4$ alkyl,
$C_1$–$C_4$ alkenyl containing 1 or 2 double bonds,
$C_1$–$C_4$ alkynyl containing 1 triple bond,
—CO—$OE_{2-1}$ where $E_{2-1}$ is —H or $C_1$–$C_4$ alkyl,
—$C(E_{2-1})_2$—$OE_{2-2}$ where $E_{2-1}$ are the same or different and are as defined above and where $E_{2-2}$ is
$C_1$–$C_4$ alkyl,
-Φ or
—$Si(R)_3$ where the three R are the same or different and are defined above, —$OE_{2-2}$ where $E_{2-2}$ is as defined above,
—S—$E_{2-3}$ where $E_{2-3}$ is $C_1$–$C_4$ alkyl or -Φ,
—S—$(O)_{1-2}$—$E_{2-3}$ where $E_{2-3}$ is as defined above,
—$N(R_{d-6})_2$ where the two $R_{d6}$ are the same or different and are as defined above;
—$Si(R)_3$ where the three R are as defined above;
(3) =$C(E_2)_2$ where the $E_2$ are the same or different and are as defined above,
where $E_1$ and $E_2$ are taken together with the atoms to which they are attached to form a ring of 5 thru 7 members, optionally containing 3 thru 5
—O—,
—S—,
—N=,
—$NX_{1-1}$— where $X_{1-1}$ is as defined above,
—$CE_2$= where $E_2$ is as defined above,
—$C(R_b)_2$— where $R_b$ is as defined above, and optionally containing 1 or 2 additional double bonds;

—C≡C—$E_2$     (-C)

where $E_2$ is as defined above;

—$CH_2$—CH=$CH_2$     (-D1)

—CH=C=$CH_2$     (-D2)

—$CH_2$—C≡C—H     (-D3)

where $R_9$ is:
(1) —H,
(2) —OH,
(3) —O-(HYDROXY PROTECTING GROUP) where HYDROXY PROTECTING GROUP is selected from the group consisting of
—$Si(-CH_3)_3$,
—$Si(-CH_2-CH_3)_3$,
—CO—$CH_3$,
—CO—H and
—$SiH(CH_3)_2$,
(4) —F;
where $R_{11}$ is:
(1) =O,
(2) —H:—H,
(3) α-$R_{11-1}$:β-$R_{11-2}$ where $R_{11-1}$ is:
(a) —H,
(b) —O—$R_{11-3}$ where $R_{11-3}$ is:
(i) —H,
(ii) a HYDROXY PROTECTING GROUP) where HYDROXY PROTECTING GROUP is as defined above, and where $R_{11-2}$ is:
(a) —H,
(b) —O—$R_{11-4}$ where $R_{11-4}$ is:
(i) —H,
(ii) a HYDROXY PROTECTING GROUP) where HYDROXY PROTECTING GROUP is as defined above, with the proviso that one of $R_{11-1}$ and $R_{11-2}$ must be —H,
(4) $R_{11-5}$:$R_{11-6}$ where one of $R_{11-5}$ or $R_{11-6}$ and $R_9$ are taken together with $R_9$ to form a second bond between C-9 and C-11 and the other of $R_{11-5}$ or $R_{11-6}$ is —H,
(5) α-$R_{11-7}$:β-$R_{11-8}$ where $R_{11-7}$ and $R_9$ are taken together with —O— to form an epoxide between C-9 and C-11 and $R_{11-8}$ is —H;
where $R_{17}$ is:
(1) =O;
(2) α-$R_{17-1}$:β-$R_{17-2}$ where $R_{17-1}$ is:
(a) —H,
(b) —C≡C—H, (c) —C≡N,
(d) —C≡C—CH$_2$—O—R$_{17-1-1}$ where R$_{17-1-1}$ is selected from the group consisting of
  (i) —H,
  (ii) —Si(R$_{17-1-2}$)$_3$ where R$_{17-1-2}$ are the same or different and are C$_1$–C$_4$ alkyl,
  (iii) 1-ethoxyethyl,
  (iv) 2-tetrahydropyranyl,
(e) —C≡C—CH$_2$—O-(HYDROXY PROTECTING GROUP), where HYDROXY PROTECTING GROUP is as defined above,
(f) —CH$_2$—CH$_2$—CH$_2$—OH,
(g) —CH$_2$—CH$_2$—CH$_2$—O-(HYDROXY PROTECTING GROUP) where HYDROXY PROTECTING GROUP is as defined above,
(h) —CH$_2$—CH$_2$—CO—O$^-$ and where R$_{17-2}$ is —OH;
(3) α-R$_{17-3}$:β-R$_{17-4}$ where R$_{17-3}$ is —OH and where R$_{17-4}$ is:
  (a) —CO—CH$_3$,
  (b) —CO—CH$_2$—OH,
  (c) —CO—CH$_2$—O—CO—(CH$_2$)$_{0-3}$—CH$_3$;
(4) α-R$_{17-5}$:β-R$_{17-6}$ where R$_{17-5}$ and R$_{17-6}$ are taken with the attached carbon atom to form a three member epoxide containing —O—CH$_2$— where the attachment of the —O is at R$_{17-6}$ in the β-orientation and the attachment of the CH$_2$— is at R$_{17-5}$ in the α-orientation;
(5) α-R$_{17-7}$: β-R$_{17-8}$ where R$_{17-7}$ and R$_{17-8}$ are taken with the attached carbon atom to form a five member lactone containing —O—CO—CH$_2$—CH$_2$— where the attachment of the CH$_2$— is at R$_{17-7}$ in the α-orientation and the attachment of the —O is at R$_{17-8}$ in the β-orientation;
(6) —O—CH(OR$_{17-9}$)—CH$_2$—CH$_2$ . . . where the bond from the oxygen (—O) is one of the four bonds at C-17 in the β-configuration and the bond from the methylene group (CH$_2$ . . . ) is another of the four bonds at C-17 in the α-configuration to form a 5 member heterocycle containing one oxygen atom, where R$_{17-9}$ is —H or C$_1$–C$_3$ alkyl;
(7) α-R$_{17-11}$:β-R$_{17-12}$ where R$_{17-10}$ is —CH$_2$)$_2$—CH=CH$_2$ and R$_{17-12}$ is —OH; which comprises:
(1) contacting a Δ$^{4,6}$-3-keto steroid or ketal thereof (I) of the formula

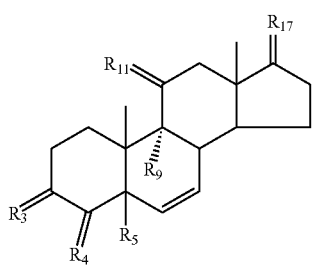

(I)

where
(I) R$_3$ is =O; R$_4$ is R$_{4-1}$:R$_{4-2}$ where one of R$_{4-1}$ and R$_{4-2}$ is —H and the other of R$_{4-1}$ and R$_{4-2}$ is taken together with R$_5$ to form a second bond between the carbon atoms to which they are attached;

(I-ketal) R$_3$ is R$_{3-9}$:R$_{3-10}$ where R$_{3-9}$ is —O—R$_{31}$ and R$_{3-10}$ is —O—R$_{32}$ where R$_{31}$ and R$_{32}$ are the same or different and are selected from the group consisting of
C$_1$–C$_3$ alkyl and
R$_{31}$ and R$_{32}$ are taken with the attached —O—C—O— to form a cyclic ketal of 5 or 6 atoms of the formula —(CH$_2$)—(CR$_{33}$R$_{34}$)$_{n1}$—(CH$_2$)— where n, is 0 or 1;

where R$_{33}$ and R$_{34}$ are the same or different and are —H and C$_1$–C$_3$ alkyl; R$_4$ is R$_{4-9}$:R$_{4-10}$ where one of R$_{4-9}$ and R$_{4-10}$ is taken together with R$_5$ to form a second bond between the carbon atoms to which they are attached and the other of R$_{4-9}$ and R$_{4-10}$ is —H;

where R$_9$, R$_{11}$ and R$_{17}$ are as defined above, with an adduct selected from compounds
(a) of the formula (A)

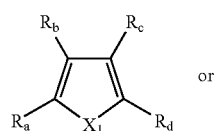

(A1)

or

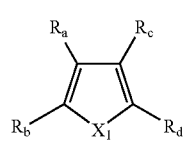

(A2)

where X$_1$, R$_b$, R$_c$ and R$_d$ are as defined above, and
where R$_a$ is selected from the group consisting of —H, —ZnL, —BL, —SiL$_3$, —SnL$_3$, —Cu, —CuL, —AlL$_2$, —HgL, —Ag, —MgL, —Li and —COOH, where L is —OH, C$_1$–C$_4$ alkyl, —F, —Cl, —Br, —I, —CN, —O(C$_1$–C$_3$ alkyl), 2-thienyl, (CH$_3$)$_2$C(O—)—C(O—)C(CH$_3$)$_2$ and

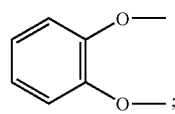

;

(b) of the formula (A')

R$_b$—CO—CHR$_b$—CHR$_c$—CO—R$_d$   (A')

where R$_b$, R$_c$ and R$_d$ are as defined above;
(c) of the formula (A")

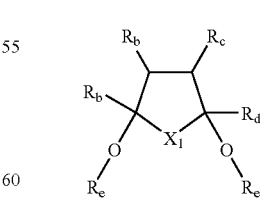

(A")

where R$_e$ is:
C$_1$–C$_4$ alkyl,
—CO—(C$_1$–C$_4$ alkyl or -Φ),
—Si(R)$_3$ where R is as defined above and where X$_1$, R$_b$, R$_c$ and R$_d$ are as defined above;

(d) of the formula (B)

$$R_a\text{—}CE_1\text{=}M \quad (B)$$

where $R_a$, $E_1$ and M are as defined above;
(e) of the formula (C)

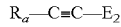
$$R_a\text{—}C\text{≡}C\text{—}E_2 \quad (C)$$

where $R_a$ and $E_2$ are as defined above;
(f) of the formulas (D1, D2 and D3)

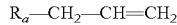
$$R_a\text{—}CH_2\text{—}CH\text{=}CH_2 \quad (D1)$$

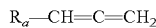
$$R_a\text{—}CH\text{=}C\text{=}CH_2 \quad (D2)$$

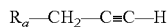
$$R_a\text{—}CH_2\text{—}C\text{≡}C\text{—}H \quad (D3)$$

where $R_a$ is as defined above, in the presence of:
(1) a Lewis Acid,
(2) a proton acid with a $pK_a$ of < about 5 or
(3) a salt of a secondary amine of the formula

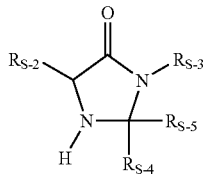

where
$R_{S-2}$ is —H, $C_1$–$C_4$ alkyl, -Φ, and —$CH_2$-Φ;
$R_{S-3}$ is —H, $C_1$–$C_4$ alkyl;
$R_{S-4}$ is —H, $C_1$–$C_4$ alkyl, -Φ;
$R_{S-5}$ is —H, $C_1$–$C_4$ alkyl, -Φ;
and

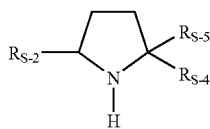

where
$R_{S-2}$ is —H, $C_1$–$C_4$ alkyl, -Φ, and —$CH_2$-Φ;
$R_{S-4}$ is —H, $C_1$–$C_4$ alkyl, -Φ;
$R_{S-5}$ is —H, $C_1$–$C_4$ alkyl, -Φ;
with an acid of $pK_a$ of < about 2.

For the $\Delta^4$-3-keto or ketal thereof (I) starting material it is preferred that $R_3$, $R_4$ and $R_5$ are (I) $R_3$ is =O; $R_4$ is $R_{4-1}$:$R_{4-2}$ where one of $R_{4-1}$ and $R_{4-2}$ is —H and the other of $R_{4-1}$ and $R_{4-2}$ is taken together with $R_5$ to form a second bond between the carbon atoms to which they are attached; $R_6$ is —H:—H.

For the 7α-substituted steroid (II), there were four sets of steroid A-/B-rings identified above. Groups (I), (III) and (IV) are operable in the processes of the present invention. However, group (II) where $R_3$ is $R_{3-3}$:$R_{3-4}$ and $R_4$ is $R_{43}$:$R_{4-4}$ where one of $R_{3-3}$ and $R_{3-4}$ is —O—$R_{31}$ where $R_{31}$ is $C_1$–$C_3$ alkyl, the other of $R_{3-3}$ and $R_{3-4}$ is taken together with one of $R_{4-3}$ and $R_{4-4}$ to form a second bond between the carbon atoms to which they are attached, and the other of $R_{4-3}$ and $R_{4-4}$ is —H; $R_6$ is $R_{6-3}$:$R_{6-4}$ where one of $R_{6-3}$ and $R_{6-4}$ is taken together with $R_5$ to form a second bond between the carbon atoms to which they are attached and the other of $R_{6-3}$ and $R_{6-4}$ is —H; is a $\Delta^{3,5}$-3,3-dialkoxy ring system which, as such, can not be transformed to the other intermediates of the present invention. It is useful because it can be transformed to the corresponding $\Delta^4$-3-keto steroid A-/B-ring system which is useful in the processes of the present invention.

For the 7α-substituted steroid (II) and other steroidal compounds of the invention, except the 5,7-bislactone (VII), with regard to the steroidal A-/B-rings, it is preferred that $R_3$, $R_4$, $R_5$ and $R_6$ are selected from the group consisting of:

(I) $R_3$ is =O; $R_4$ is $R_{4-1}$:$R_{4-2}$ where one of $R_{4-1}$ and $R_{4-2}$ is —H and the other of $R_{4-1}$ and $R_{4-2}$ is taken together with $R_5$ to form a second bond between the carbon atoms to which they are attached; $R_6$ is —H:—H;

(II) $R_3$ is α-$R_{3-5}$:β-$R_{3-6}$ where $R_{3-5}$ is —O—$R_{31}$ and $R_{3-6}$ is —O—$R_{32}$ where $R_{31}$ and $R_{32}$ are taken with the attached —O—C—O— to form a cyclic ketal of 5 atoms of the formula —$(CH_2)$—$(CR_{33}R_{34})_{n1}$—$(CH_2)$— where $n_1$ is 0; $R_4$ is —H:—H; $R_6$ is $R_{6-5}$:$R_{6-6}$ where one of $R_{6-5}$ and $R_{6-6}$ is taken together with $R_5$ to form a second bond between the carbon atoms to which they are attached and the other of $R_{6-5}$ and $R_{6-6}$ is —H;

(III) $R_3$ is α-$R_{3-5}$:β-$R_{3-6}$ where $R_{3-5}$ is —O—$R_{31}$ and $R_{3-6}$ is —O—$R_{32}$ where $R_{31}$ and $R_{32}$ are taken with the attached —O—C—O— to form a cyclic ketal of 6 atoms of the formula —$(CH_2)$—$(CR_{33}R_{34})_{n1}$—$(CH_2)$— where $n_1$ is 1 and $R_{33}$ and $R_{34}$ are both $C_1$ alkyl; $R_4$ is —H:—H; $R_6$ is $R_{6-5}$:$R_{6-6}$ where one of $R_{6-5}$ and $R_{6-6}$ is taken together with $R_5$ to form a second bond between the carbon atoms to which they are attached and the other of $R_{6-5}$ and $R_{6-6}$ is —H.

For the 7α-substituted steroid (II) and other steroidal compounds of the invention, except the 5,7-bislactone (VII), with regard to the steroidal A-/B-rings, it is more preferred that $R_3$, $R_4$, $R_5$ and $R_6$ are:

(I) $R_3$ is =O; $R_4$ is $R_{4-1}$:$R_{4-2}$ where one of $R_{4-1}$ and $R_{4-2}$ is —H and the other of $R_{4-1}$ and $R_{4-2}$ is taken together with $R_5$ to form a second bond between the carbon atoms to which they are attached; $R_6$ is —H:—H.

With regard to the steroidal C-ring, it is preferred that $R_9$ and $R_{11}$ are:
(a) $R_{11}$ is $R_{11-5}$:$R_{11-6}$ where one of $R_{11-5}$ or $R_{11-6}$ and $R_9$ are taken together with $R_9$ to form a second bond between C-9 and C-11 and the other of $R_{11-5}$ or $R_{11-6}$ is —H,
(b) α-$R_{11-7}$:β-$R_{11-8}$ where $R_{11-7}$ and $R_9$ are taken together with —O— to form an epoxide between C-9 and C-11 and $R_{11-8}$ is —H,
(c) $R_9$ is —H and $R_{11}$ is α-$R_{11-1}$:β-$R_{11-2}$ where $R_{11-1}$ is —O—$R_{11-3}$ where $R_{11-3}$ is —H, and where $R_{11-2}$ is —H.
It is more preferred that $R_9$ and $R_{11}$ are:
(a) $R_{11}$ is $R_{11-5}$:$R_{11-6}$ where one of $R_{11-5}$ or $R_{11-6}$ and $R_9$ are taken together with $R_9$ to form a second bond between C-9 and C-11 and other of $R_{11-5}$ or $R_{11-6}$ is —H.

With regard to the steroidal D-ring, it is preferred that $R_{17}$ is selected from the group consisting of:
(a) α-$R_{17-7}$:β-$R_{17-8}$ where $R_{17-7}$ and $R_{17-8}$ are taken with the attached carbon atom to form a five member lactone containing —O—CO—$CH_2$—$CH_2$— where the attachment of the $CH_2$— is at $R_{17-7}$ in the α-orientation and the attachment of the —O is at $R_{17-8}$ in the β-orientation,
(b) =O;
(c) α-$R_{17-1}$:β-$R_{17-2}$ where $R_{17-1}$ is —C≡C—H and where $R_{17-2}$ is —OH,
(d) —C≡C—$CH_2$—O—$R_{17-1-1}$.

With regard to the 7α-substituted steroid (II), it is preferred that $R_{7-1}$ is substituent of formula (-A1). It is also preferred that $X_1$ is —O—. It is preferred that $R_b$ and $R_d$ are —H and it is preferred that $R_d$ is $C_1$ alkyl. It is preferred that $R_a$ is —H. It is preferred that for $R_a$ that L is —ZnL is —Cl, —Br, —I;
—BL is catecholate,
two —OH,
HO—$CH_2$—$CH_2$—OH,
HO—$CH_2$—$CH_2$—$CH_2$—OH,
HO—$CH_2$—$C(CH_3)_2$—$CH_2$—OH;
—$SiL_3$ is $C_1$ alkyl;
—$SnL_3$ is $C_1$ or n-$C_4$ alkyl;
—CuL is 2-thienyl or —CN and
—$AlL_2$ is $C_1$–$C_2$ alkyl.

When $R_a$ is Cu, there can be two $R_a$ groups for one Cu in which case the Cu is anionic.

The preferences for the variable substituents $R_3$, $R_4$, $R_5$, $R_6$, $R_{7-1}$, $R_9$, $R_{11}$, $R_{17}$, $R_a$, $R_b$, $R_c$, $R_d$ and $X_1$ are not just for the $\Delta^{4,6}$-3-keto steroid or ketal thereof (I) and/or the 7α-substituted steroid (II), but rather are for all the compounds (I) thru (XV) of the invention, except as expressly noted. Similarly, the preferences for other variable substituents such as $R_{7-2}$ discussed below and/or chemical reagents used in this patent such as oxygen donating agent, halogenating agent, isomerization catalyst, hydroperoxy-deoxygenating agent, acid forming agent, acylation catalyst, oxidatively cleaving agent, deoxygenating agent, are defined the same throughout the patent as the first time they are discussed. Since many of these variable substituents and chemical reagents are referred to numerous times, it would be redundant each time they are used to repeatedly mention what is included, what is preferred and more preferred.

It is preferred that the acid reactant be a Lewis acid. The Lewis acid must be electrophilic enough to complex with the $\Delta^{4,6}$-3-keto steroid or ketal thereof (I), but not so electrophilic that it complexes with the nucleophilic reagent (A1), (A2), (B), (C), (D1), (D2) or (D3) as is known to those skilled in the art. Further, it is preferred that the Lewis Acid be used in the presence of an alcohol selected from the group consisting of $C_1$–$C_3$ alcohols, ethylene glycol, 1,2- or 1,3-propylene glycol, 2,2-dimethyl- or 2,2-diethyl-1,3-propylene glycol and phenol. It is more preferred that the alcohol be a $C_1$–$C_3$ alcohol or mixture thereof.

Useful Lewis acids include those selected from the group consisting of $BX_3$, $AlX_3$, $SnX_2$, $SnX_4$, $SiX_4$, $MgX_2$, $ZnX_2$, $TiX_4$,
Rh(acac)($CH_2CH_2$)$_2$(2,2'-bis(diphenylphosphino)-1,1'-binaphthyl),
Rh($CH_3$—C≡N)$_2$(cyclooctadiene)($BF_4$),
Rh(acac)($CH_2CH_2$)$_2$(dppb),
$LiClO_4$,
K10 Montmorillonite clay,
Yb(OTf)$_3$,
LiCo($B_9C_2H_{11}$)$_2$,
$PdX_2$,
$CrX_3$,
$FeX_3$,
$CoX_3$,
$NiX_2$,
$SbX_5$,
$InX_3$,
Sc(OTf)$_3$,
$\Phi_3C^+X^-$
(R)$_3$SiX where R is $C_1$–$C_4$ alkyl and -Φ; where X is selected from the group consisting of $F^-$, $Cl^-$, $Br^-$, $I^-$, —O—$SO_2CF_3^-$, $PF_6^-$, $BF_4^-$, and $ClO_4^-$;
Pd($CH_3$—CO—O$^-$)$_2$;
$BF_3$-diethyletherate complex;
$BF_3$-acetic acid complex;
$BF_3$-methyl-t-butyl ether complex;
$BF_3$-di-n-butyletherate complex;
$BF_3$-dimethyletherate complex;
$BF_3$-dimethylsulfide complex;
$BF_3$-phenol complex;
$BF_3$-phosphoric acid complex and
$BF_3$-tetrahydrofuran complex. It is preferred that the Lewis acid is selected from the group consisting of $BF_3$, $BF_3$-diethyletherate complex, $BF_3$-acetic acid complex, $BF_3$-methyl-t-butyl ether complex, $BF_3$-di-n-butyletherate complex, $BF_3$-dimethyletherate complex, $BF_3$-dimethylsulfide complex, $BF_3$-phenol complex, $BF_3$-phosphoric acid complex and $BF_3$-tetrahydrofuran complex. It is more preferred that the Lewis acid is $BF_3$-diethyletherate. It is even more preferred that the $BF_3$-diethyletherate is used in the presence of $C_1$–$C_3$ alcohol and still more preferred is the use of the $BF_3$-diethyletherate in the presence of $C_2$ alcohol. Useful acids with a $pK_a$ of < about 5 are selected from the group consisting of formic acid, acetic acid, propionic acid, benzoic acid, acid, hydrofluoric acid, fluoroboric acid, p-toluenesulfonic acid, methanesulfonic acid, benzenesulfonic acid, trifluoromethanesulfonic acid, perchloric acid, trifluoroacetic and trichloroacetic. It is preferred that the acid with a $pK_a$ of < about 5 is acetic acid. When performing the transformation of the $\Delta^{4,6}$-3-keto steroid or ketal thereof (I) to the corresponding 7α-substituted steroid (II), at least one equivalent of the reagent of formulas (A), (B) or (C) should be used, it is preferable to use from one to two equivalents. Use of additional reagent is not a problem, but rather a waste of compound. The reaction can be carried out in a variety of solvents, such as in a solvent/solvent mixture selected from the group consisting of:

$C_1$–$C_6$ alcohols, a solvent mixture of $C_1$–$C_6$ alcohols and a solvent selected from the group consisting of acetonitrile, nitromethane, toluene, methylene chloride and acetic acid. One factor to be considered in selecting a Lewis acid and solvent is the acid sensitivity of the 7α-substituted steroid (I). The reaction must be performed with a Lewis acid and in a solvent where the product is stable as is known to those skilled in the art. It is preferred that the solvent be a protic solvent, one that has a $pK_a$ of less than about 19. The reaction can be performed in a temperature range of from about −78° to about 60°; preferably in a temperature range of from about −40° to about −15°. It is more preferred to perform the reaction at about −20°. The reaction normally will take from a few hours to a day depending on the number of equivalent used and the reaction temperature.

Useful 7α-substituted steroids (II) include those selected from the group consisting of:

17β-hydroxy-7α-(5'-methyl-2'-furyl)-pregna-4,9-dien-3-one-2-carboxylic acid, γ-lactone, 11α,17β-dihydroxy-7α-(5'-methyl-2'-furyl)-pregn-4-en-3-one-21-carboxylic acid, γ-lactone, 9α,11α-epoxy-17β-hydroxy-7α-(5'-methyl-2'-furyl)-pregn-4-en-3-one-21-carboxylic acid, γ-lactone, 17β-hydroxy-7α-(5'-t-butyl-2'-furyl)-pregna-4,9(11)-dien-3-one-21-carboxylic acid, γ-lactone, 11α,17β-dihydroxy-7α-(5'-t-butyl-2'-furyl)-pregn-4-en-3-one-21-carboxylic acid, γ-lactone, 11α,17β-dihydroxy-7α-(4'-bromo-2'-furyl)-pregn-4-en-3-one-21-carboxylic acid, γ-lactone, 11α,17β-dihydroxy-7α-(4'-methyl-2'-furyl)-pregn-4-en-3-one-21-carboxylic acid, γ-lactone and 7α-allyl-17β-hydroxypregna-4,9(11)-dien-3-one, 21-carboxylic acid, γ-lactone.

Rather than carrying the 7α-substituted steroid (II) on to the next step in situ, it is preferred to isolate and purify the 7α-substituted steroid (H) before performing the next step. The preferred method of purification of the 7α-substituted steroid (II) is by crystallization. The process for purifying the 7α-substituted steroid of formula (II) comprises crystallizing the 7α-substituted steroid (II), which contains greater than 5% of the 7Oβ-isomer from a solvent selected from the group consisting of ethyl acetate, n-propyl acetate and butyl acetate. It is preferred to obtain the 7α-substituted steroid (II) in greater than 99.8% isomeric purity and it is preferred that the crystallization solvent is n-propyl acetate. Crystallization co-solvents may be used.

The above purification of the 7α-substituted steroid (II) results in crystalline 7α-substituted steroid (II). However, crystalline 7α-substituted steroid (II) can also be readily obtained from other solvents, including methylene chloride, methanol, acetonitrile, acetone; cyclohexane and iso-octane as well as solvent mixtures of these solvents or a mixture of acetonitrile with water. Crystalline 7α-substituted steroid (II) can be readily obtained by methods well known to those skilled in the art for crystallization. For example, the 7α-substituted steroid (II) desired to be obtained in crystalline form is dissolved in a minimal amount of a suitable solvent, the mixture is heated until all the 7α-substituted steroid (II) is in solution and then the mixture is cooled until crystals result. Alternatively, once the 7α-substituted steroid (II) is in solution in a suitable solvent such as ethyl acetate, the volume of the solvent can be reduced by distillation, or by passing a stream of a dry inert gas such as nitrogen over the mixture to concentrate the 7α-substituted steroid (II). Further, anti-solvents, such as cyclohexane or iso-octane, can be added to the warm mixture to help reduce the solubility of the 7α-substituted steroid (II) in the solvent and promote its crystallization as is known to those skilled in the art. The preferred solvents for crystallization are those used for purification.

It has been determined by powder X-ray diffraction (PXRD) that the crystals of 17β-hydroxy-7α-(5'-methyl-2'-furyl)-pregna-4,9(11)-dien-3-one-21-carboxylic acid, γ-lactone (II) regardless of which process of the invention was used to make it and regardless of what solvent(s) it is crystallized from, that only one crystal form is produced. EXAMPLEs 39–53 are PXRD analysis of different samples of crystalline 17β-hydroxy-7α-(5'-methyl-2'-furyl)-pregna-4,9(11)-dien-3-one-21-carboxylic acid, γ-lactone (1H) obtained by various process and crystallized from various solvent systems. The results are substantially identical. The differences are due to the identity and amount of a particular impurity that may be present as well as residual solvent as is known to those skilled in the art. It is known to those skilled in the art that even if the same sample is subjected to PXRD on more than one occasion, that the results will not be identical. That is know as experimental error and understood by those skilled in the art. It is the overall analysis that determines whether or not two crystal forms are the same or different.

In determining the PXRD of a crystal, the particular instrument used as well as the power of the instrument will affect the results. In determining whether two samples have the same or different crystal form, a scientist will compare the location of peaks or bands and look to see if there are any new bands in either sample not present in the other. In addition, the relative intensity of the peaks is very important.

The next step in the process of CHART A, is the conversion of the 7α-substituted steroid (II) to the corresponding cis-enedione (III-cis), by an oxidative process which comprises (1) contacting the 7α-substituted steroid of formula (II) with an agent selected from the group consisting of:
  (a) a halogenating agent in the presence of water and a base whose conjugate acid has a $pK_a$ of > about 8,
  (b) an oxygen donating agent,
  (c) electrochemical oxidation,
  (d) a quinone in the presence of water or
  (e) nonquinone oxidants. It is preferred that the agent be a halogenating agent. Useful halogenating agents include those selected from the group consisting of dibromodimethylhydantoin, dichlorodimethylhydantoin, diiododimethylhydantoin, N-chlorosuccinamide, N-bromosuccinamide, N-iodosuccinamide, trichloroisocyanuric acid, t-butylhypochlorite and 3-bromo-1-chloro-5,5-dimethylhydantoin; it is preferred that the halogenating is dibromodimethylhydantoin. When using a halogenating agent, the amount used should be at least one equivalent of the halogenating agent; preferably from about 1.0 to about 1.05 equivalents of the halogenating agent are used. It is more preferred that the amount of halogenating agent be about 1.01 equivalents. The reason is that one equivalent is required to complete the reaction but any excess needs to be quenched. Suitable quenching agents include bisulfite, isobutylvinyl ether, 2-methylfuran and hypophosphorous acid.

Useful oxygen donating agents include those selected from the group consisting of:
  a peracid,
  singlet oxygen followed by either phosphite or thiourea,
  triplet oxygen,
  hydrogen peroxide with a ketone selected from the group consisting of $Q_4$—CO—$Q_5$ where $Q_4$ and $Q_5$ are the same or different and are:
    $C_1$–$C_4$ alkyl optionally substituted with 1 thru 9 —Cl or —F, and where the
    $Q_4$ and $Q_5$ are taken together with the attached carbon atom to form a cyclic ketone of 5 thru 7 members and ketones of the formula:

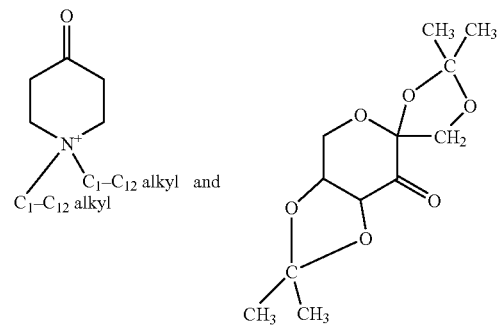

hydrogen peroxide in combination with methyltrioxorhenium,
  trichloroacetonitrile/hydrogen peroxide,
  trichloroacetamide/hydrogen peroxide,
  DDQ/water,
  p-chloranil/water,
  Φ-C(CH$_3$)$_2$—O—OH or an alkylhydroperoxide in combination with a metal containing activator, where alkyl is from $C_4$–$C_{10}$ alkyl and metal containing activator is selected from the group consisting of Ti(isopropoxide)$_4$, peroxotungstophosphate, VO(acetylacetonate)$_2$ and MO hexacarbonyl. It is preferred that the oxygen donating agent is a peracid. Useful peracids include those selected from the group consisting of:

(a) perbenzoic acid optionally substituted with 1 or 2 —Cl or —NO$_2$, (b) percarboxylic acids of the formula $C_{n2}(Q_6)2_{n2+1}$—CO$_3$H where n$_2$ is 1 thru 4 and Q$_6$ is —H, —Cl or —F, (c) perphthalic acid and (d) magnesium peroxyphthalate. An excess oxygen donating agent present must also be quenched as was done for the halogenating agents. Base is required to neutralize the acid produced during the transformation of the 7α-substituted steroid (II) to the cis-enedione (III-cis). Use bases include those selected from the group consisting of acetate, bicarbonate, carbonate, propionate, benzoate, dibasic phosphate and borate; it is more preferred that the base be acetate. For example, when the halogenating agent is dibromodimethylhydantoin, hydrobromic acid is produced. Hence, one equivalent of base per equivalent of acid produced is required. In practice, a slight excess is used, about 1.5 equivalents. Suitable solvents for this reaction are those which are water miscible and which dissolves both the 7α-substituted steroid (II) and the halogenating agent or oxygen donating agent. Acetone and THF are preferred solvents. The reaction is performed at room temperature, about 20 to about 25°. The reaction takes a few hours depending on the reactivity of the oxygenating donating agent or halogenating agent. When formed, the cis-enedione (UI-cis) does not have to be isolated and purified, but rather can be used in subsequent transformations "as is" or in situ. It is preferred that the cis-enedione (M-cis) is 17β-hydroxy-7α-(cis-1',4'-dioxopent-2'-en-1'yl)pregna-4,9(11)-dien-3-one-21-carboxylic acid, γ-lactone. Other oxidants useful for transformation of the 7α-substituted steroid (II) to the cis-enedione (III-cis) include quinones (listed elsewhere). The 7α-substituted steroid (I) is contacted with a stoichiometric amount of quinone and at least a stoichiometric amount of water in a water-miscible organic solvent. The contacting is preferably done at around room temperature. In addition, the oxidation can be accomplished by electrochemistry. The electrochemical oxidation is accomplished by contacting the 7α-substituted steroid (II) with a sub-stoichiometric amount of a quinone (preferably DDQ) and at least a stoichiometric amount of water in an electrochemical cell using standard electrochemical techniques such as are described in U.S. Pat. No. 4,270,994. Finally, the oxidation can be accomplished with non-quinone agents which include, manganic acetate, potassium permanganate, ceric ammonium nitrate, iodosobenzene, iodobenzenediacetate, iodobenzenebistrifluoroacetate, chromic acid ("Jones reagent"), and lead tetraacetate. These reactions are typically run in aqueous acetone as solvent at around room temperature (20–25°), although many water-miscible organic co-solvents can be used in place of acetone. Other oxidizing agents that effect this transformation include hydrogen peroxide or an organic hydroperoxide (listed elsewhere) in combination with a metal catalyst such as methyltrioxorhenium, palladium acetate, ruthenium trichloride, or ruthenium tetroxide. These reactions can be run in any solvent in which the 7α-substituted steroid (II) is soluble such as methylene chloride, acetone, etc. The reactions involving ruthenium catalysts are preferably run in aqueous acetonitrile.

In the process of CHART A, the cis-enedione (M-cis) can be transformed to the corresponding trans-enedione (III-trans) or it can be converted to the peroxy compound (IV-OOH), the hydroxy compound (IV-OH), the biscarbonyl compound (V) or the carboxylic acid (VI) or mixture thereof. When the term carboxylic acid (VI) is used, it refers to and includes the pharmaceutically acceptable salts thereof. These will include the sodium, potassium, lithium, magnesium, tetrabutylammonium and the carboxylic acid salts with DBU, tetramethylquanidine, triethylamine and others. The identity of the particular cation is not important since eventually it is lost when forming an acid which ultimately is converted to the methyl ester (VIII) and eplerenone (IX) which requires a methyl ester at the 7α-position. It is preferable to convert the cis-enedione (III-cis) to the corresponding trans-enedione (R$_1$-trans) rather than convert the cis-enedione (III-cis) to a mixture of peroxy (IV-OOH), hydroxy (IV-OH) and biscarbonyl (V) compounds.

When the cis-enedione (III-cis) is transformed to the corresponding trans-enedione (III-trans), the cis-enedione (III-cis) is contacted with an isomerization catalyst which can be either a chemical agent including:

(a) a strong acid of pK$_a$ of < about 2;

(b) a tertiary amine whose conjugate acid has a pK$_a$> about 8 and (c) salt of a tertiary amine whose conjugate acid has a pK$_a$> about 8, (d) I$_2$, (e) (C$_1$–C$_4$)$_3$P, (f) Φ$_3$P, or a physical agent such as (g) heating to about 80°.

It is preferred that the isomerization catalyst be a strong acid of pK$_a$ of < about 2. When the isomerization catalyst is a strong acid of pK$_a$ of < about 2, useful strong acids of pK$_a$ of < about 2 include those selected from the group consisting of hydrochloric acid, hydrobromic acid, hydroiodoic acid, hydrofluoroic acid, sulfuric acid, phosphoric acid, nitric acid, trichloroacetic acid and trifluoroacetic acid, it is preferred that the strong acid of pK$_a$ of < about 2 be hydrochloric acid. When the isomerization catalyst is a strong acid of pK$_a$ of < about 2, it is preferred that it be used in anhydrous form or if used in as an aqueous mixture that the reaction be performed as a two phase system with the aqueous phase being separate. When the isomerization catalyst is a tertiary amine whose conjugate acid has a pK$_a$> about 8, useful tertiary amines whose conjugate acid has a pK$_a$> about 8 include those selected from the group consisting of (Q$_3$)$_3$N were Q$_3$ is C$_1$–C$_3$ alkyl, DBU, DBN, DABCO, pyridine, p-dimethylaminopyridine and pyrrolidinylpyridine. When the isomerization catalyst is salt of a tertiary amine whose conjugate acid has a pK$_a$> about 8, it is preferred that the salt of a tertiary amine whose conjugate acid has a pK$_a$> about 8 be pyridine hydrochloride. Regardless of which chemical agent is used, only a catalytic amount is required. For example, after formation of the cis-enedione (III-cis) just adding commercial chloroform containing the usual impurity of hydrochloric acid is sufficient to effect the transformation to the corresponding trans-enedione (III-trans), see EXAMPLE 4, Part 2. The isomerization of cis-enedione (III-cis) to the corresponding trans-enedione (III-trans) can be performed at 20–25° (room temperature). At room temperature, the reaction usually takes a few hours. It is necessary to monitor the course of the reaction by standard methods such as LC or TLC to ensure that it does not go too long. If the reaction goes too long, the reaction reforms the 7α-substituted steroid (II) with a Δ$^6$-double bond. Once the reaction has proceeded to completeness where it is desirous to terminate the reaction, the reaction can be terminated as follows. When the isomerization catalyst is an acid or salt of a tertiary amine whose conjugate acid has a pK$_a$ of >8, one can terminate the reaction by washing with water. If aqueous acid is used as the isomerization catalyst, it is best to separate the phases and then wash the non-aqueous phase with water. If the isomerization catalyst is a tertiary amine whose conjugate acid has a $pK_a$ of >8, then the reaction mixture is washed with aqueous acid followed by water. The trans-enedione (M-trans) can be isolated and purified, however it is preferred not to isolate and purify it but rather carry it on in situ.

In the process of CHART A, the next step is the conversion of either the cis-enedione ($R_1$-cis) or trans-enedione (III-trans), or mixture thereof, to the corresponding hydroperoxy (IV-OOH) compound, hydroxy (IV-OH) compound, biscarbonyl (V) compound and/or the carboxylic acid (VI) or mixtures thereof. The cis-enedione (III-cis) or trans-enedione (III-trans), or mixture there of, is transformed to the corresponding hydroxy compound, peroxy compound (IV-OOH), or biscarbonyl compound (V) or carboxylic (VI) by contacting the cis-enedione (III-cis) or trans-enedione (III-trans) or a mixture thereof, with ozone in the presence of an alcohol of the formula $R_{7-2}$—OH where $R_{7-2}$ is —H or $C_1$–$C_4$ alkyl optionally substituted with one or two —OH. This includes water, methanol, ethanol, propyl alcohol, isopropyl alcohol, ethylene glycol, glycerol, etc. It is preferred that $R_{7-2}$ is —H, $C_1$ or is iso-$C_3$; it is more preferred that $R_{7-2}$ is a mixture of —H, $C_1$ and iso-$C_3$. This means a mixture of water, methanol and isopropanol is the preferred $R_{7-2}$—OH. The steroidal starting materials must be in solution using a solvent that will dissolve them at the cold temperatures at which it is preferred to perform this reaction. Methylene chloride is the preferred solvent. The reaction temperatures can be as low as about −100° up to about 40°. It is preferred that the temperature be from about −78° to about −20'; it is more preferred that the temperature be about −50°. The lower the temperature, the more selectivity; the higher the temperature the less selectivity. Hence, the actual temperature used will depend on the particular reactants used and the degree of selectivity desired. The reaction is permitted to run until the starting material is reduced to a small amount. The ozone must be stopped when the starting material is consumed or the ozone will destroy the product by reacting with the $\Delta^4$- and/or $\Delta^{9(11)}$-double bonds if present. The alcohol, $R_{7-2}$—OH, is used in a large excess to efficiently trap the carbonyl oxide intermediate produced. Further, the reaction temperature, the time the reaction is permitted to run and the nature of the particular alcohol, $R_{7-2}$—OH, determines the identity of the product or if more than one product is produced, the ratio of products. If the alcohol, $R_{7-2}$—OH, has a hindered $R_{7-2}$ group, then the product is more likely to be the biscarbonyl compound (V), all other things being equal. Similarly, if the alcohol, $R_{7-2}$—OH, does not have a hindered $R_{7-2}$ group, such as methyl, then the product is more likely to be the hydroxy compound (IV-OH), all other things being equal. The preferred product produced by the oxidation process is the carboxylic acid (VI).

The hydroperoxy compound (IV-OOH) can be converted to the corresponding hydroxy compound (IV-OH) by contacting the hydroperoxy compound (IV-OOH) with a hydroperoxy-deoxygenating agent. It is preferred to use a mild hydroperoxy-deoxygenating agent, one which both deoxygenates, and second does not add to the steroid molecule. Useful hydroperoxy-deoxygenating agents include those selected from the group consisting of:

$Q_1Q_2S$ where $Q_1$ and $Q_2$ are the same or different and are $C_1$–$C_4$ alkyl or phenyl,
bisulfite,
sulfite,
thiosulfate,
tetrahydrothiophene,
hydrosulfite,
thiourea,
butyl vinyl ether,
($C_1$–$C_4$ alkyl)$_3$ phosphine,
triphenylphosphine, and
tetramethylethylene. It is preferred that the hydroperoxy-deoxygenating agent is dimethylsulfide. When the hydroperoxy-deoxygenating agent is bisulfite and sulfite, sodium and potassium are the preferred cations. One equivalent of the hydroperoxy-deoxygenating agent is required, but more then one equivalent, such as about two equivalents, are normally used to ensure that all of the hydroperoxy compound (IV-OOH) is reduced. The reaction is performed at 20–25° and is usually complete in about 1 hour. The hydroxy compound (IV-OH) can be isolated and purified if desired, however, it is preferable to carry it on in situ without isolating or purifying it. It is preferred that the hydroxy compound (IV) is 17β-hydroxy-7α-(1'-oxo-2'-isopropoxy-2'-hydroxy-ethyl)pregna-4,9(11)-dien-3-one-21-carboxylic acid, γ-lactone.

The hydroperoxy compound (IV-OOH) can be transformed to the corresponding carboxylic acid (VI) by contacting the hydroperoxy compound (IV-OOH) with a carboxylic acid forming agent selected from the group consisting of:

(a) heat,
(b) a base whose conjugate acid has a $pK_a$ of about 5 or above,
(c) an acid which has a $pK_a$ of less than about 3,
(d) an acylating agent. When the carboxylic acid forming agent is (a) heat, the reaction mixture should be heated to the range of from about 30° to about 120°; preferably from about 80° to about 90°. When the carboxylic acid forming agent is, (b) a base whose conjugate acid has a $pK_a$ of about 5 or above, useful bases include inorganic bases selected from the group consisting of hydroxide, bicarbonate, and carbonate and organic bases selected from the group consisting of $(Q_3)_3N$ were $Q_3$ is $C_1$–$C_3$ alkyl, DBU, DBN, DABCO, pyridine and p-dimethylaminopyridine. It is preferred that the base is bicarbonate. Sufficient base is necessary to neutralize the steroid acid produced and any additional acid by-products. When the carboxylic acid forming agent is, (c) an acid which has a $pK_a$ of less than about 3, useful acids include those selected from the group consisting of hydrochloric acid, sulfuric acid, phosphoric acid, nitric acid and organic acids of the formula of $R_{acid-1}$—COOH where $R_{acid-1}$ is —H and $C_1$–$C_3$ alkyl optionally substituted with 1 thru 3 —Cl and —F; preferred are formic acid and trifluoroacetic acid. While catalytic amounts of acid are sufficient, several equivalent are preferred. When the carboxylic acid forming agent is, (d) an acylating agent, useful acylating agents are selected from the group consisting of $R_{acid-2}$—CO—O—CO—$R_{acid-2}$ where $R_{acid-2}$ is
—H,
$C_1$–$C_3$ alkyl optionally substituted with 1 thru 3 —Cl and —F and
-Φ. It is preferred that acylating agent is acetic anhydride or trifluoracetic anhydride. One equivalent of the acylating agent is required. When using an acylating agent, it is preferred to use it with an acylation catalyst. Preferred acylation catalysts are pyridine and p-dimethylaminopyridine (DMAP). With regard to solvents, it is important to perform the process under homogenous reaction conditions to avoid decomposition of the hydroperoxy compound (IV-OOH). This means using one phase conditions. Therefore, the solvent of choice will depend on the carboxylic acid forming agent used. If the carboxylic acid forming agent requires water to dissolve the reagent such as when the carboxylic acid forming agent is bicarbonate, then a water miscible organic solvent such as acetone, methanol, DMF or isopropanol is required. If the carboxylic acid forming agent is pyridine then the organic solvent can be a water immiscible organic solvent such as acetonitrile, methylene chloride or ethyl acetate. Hence, the selection of the solvent depends on the nature of the carboxylic acid forming agent used as is know to those skilled in the art. With the exception of the carboxylic acid forming agent (a) heat, the other acid forming agents (b), (c) and (d) can all be reacted at 20–25°. The reaction is quite fast and is usually over in less than one hour.

Both the hydroxy compound (IV-OH) and the biscarbonyl compound (V) are converted to the corresponding carboxylic acid (VI) in the same manner. The process involves contacting the hydroxy compound (IV-OH) or the biscarbonyl compound (V), or mixture thereof, with an oxidatively cleaving agent. Useful oxidatively cleaving agents are selected from the group consisting of:

(1) hydrogen peroxide with a carboxylic acid forming agent selected from the group consisting of:
  (a) heat,
  (b) a base whose conjugate acid has a $pK_a$ of about 5 or above,
  (c) an acid which has a $pK_a$ of less than about 3,
  (d) an acylating agent and an acylation catalyst;
(2) $KRSO_5$;
(3) hydrogen peroxide with a ketone selected from the group consisting of $Q_4$—CO—$Q_5$ where $Q_4$ and $Q_5$ are the same or different and are:
  $C_1$–$C_4$ alkyl optionally substituted with 1 thru 9 —Cl or —F,
  where the $Q_4$ and $Q_5$ are taken together with the attached carbon atom to form a cyclic ketone of 5 thru 7 members, and ketones of the formula:

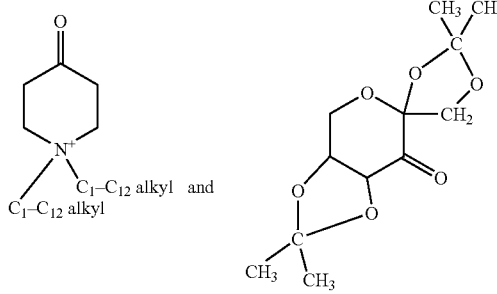

(4) hydrogen peroxide in combination with methyltrioxorhenium,
(5) Φ-C(CH$_3$)$_2$—O—OH or an alkylhydroperoxide in combination with a metal containing activator, where alkyl is from $C_4$–$C_{10}$ alkyl and metal containing activator is selected from the group consisting of Ti(isopropoxide)$_4$, peroxotungstophosphate, VO(acetylacetonate)$_2$ and Mo hexacarbonyl;
(6) peracids selected from the group consisting of
  (a) perbenzoic acid optionally substituted with 1 or 2 —Cl or —NO$_2$,
  (b) percarboxylic acids of the formula $C_{n2}(Q_6)2_{n2+1}$—CO$_3$H where $n_2$ is 1 thru 4 and $Q_6$ is —H, —Cl or —F,
  (c) perphthalic acid,
(d) magnesium peroxyphthalate. It is preferred that the oxidatively cleaving agent is hydrogen peroxide with a carboxylic acid forming agent. When the carboxylic acid forming agents are (a) heat, (b) a base whose conjugate acid has a $pK_a$ of about 5 or above, (c) an acid which has a $pK_a$ of less than about 3 or (d) an acylating agent and an acylation catalyst, they should be used in the same manner as discussed above for the transformation of the hydroperoxy compound (IV-OOH) to the corresponding carboxylic acid (VI). As stated above, one equivalent of the oxidatively cleaving agent is required. Two equivalents are normally used and the reaction is monitored so that when the reaction nears completion it is stopped, or quenched, and worked up before the oxidatively cleaving agent attacks the $\Delta^4$- and/or $\Delta^{9(11)}$-steroid double bonds. Hydrogen peroxide and bicarbonate are preferred as the oxidatively cleaving agent. With regard to solvents it is important to perform the process under homogenous reaction conditions, meaning one phase conditions. Therefore, the solvent of choice will depend on the oxidatively cleaving agent used. If the carboxylic acid forming agent requires water to dissolve the reagent such as when the carboxylic acid forming agent is bicarbonate, then a water miscible organic solvent such as acetone, DMF, methanol or isopropanol is required. If the carboxylic acid forming agent is pyridine then the organic solvent can be a water immiscible organic solvent such as acetonitrile, methylene chloride or ethyl acetate. Hence, the selection of the solvent depends on the nature of the carboxylic acid forming agent used as is known to those skilled in the art. With the exception of the carboxylic acid forming agent (a) heat, the other acid forming agents (b), (c) and (d) can all be reacted at 20–25°. The reaction is quite fast and is usually over in less than one hour. If the reaction mixture contains some hydroperoxy compound (IV-OOH), then it is useful to first treat the reaction mixture with a hydroperoxy-deoxygenating agent. It is preferred that the hydroperoxy-deoxygenating agent is dimethylsulfide. There are a number of processes to transform a carboxylic acid (VI) to the corresponding 5,7-lactone (VII), where the C- and D-rings of the starting carboxylic acid (VI) and product 5,7-lactone are the same. The processes differ depending on the nature of the steroid A-/B-rings of the starting carboxylic acid (VI). They use different reactants and produce 5,7-lactones (VI) with different steroid A-/B-rings. One of these processes produces a 5,7-lactone of formula (VI)

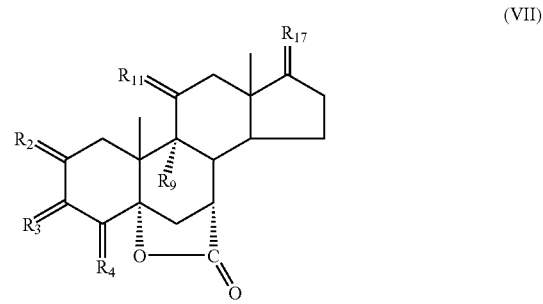

(VII)

where
(Va) $R_2$ is —H:—H; $R_3$ is =O; $R_4$ is —H:—H;
(Vb) $R_2$ is —H:—H; $R_3$ is $R_{3a}$:$R_{3b}$ where both $R_{3a}$ and $R_{3b}$ are —OH and $R_4$ is —H:—H;

where $R_9$, $R_{11}$ and $R_{11}$ are as defined above, which comprises:

(1) contacting a carboxylic acid of formula (VI)

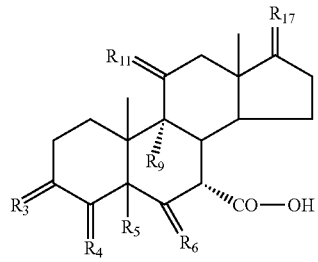

(VI)

where (I) $R_3$ is =O; $R_4$ is $R_{4-1}$:$R_{4-2}$ where one of $R_1$ and $R_{4-2}$ is —H and the other of $R_{4-1}$ and $R_{4-2}$ is taken together with $R_5$ to form a second bond between the carbon atoms to which they are attached; $R_6$ is —H:—H;

(III) $R_3$ is $\alpha$-$R_{3-5}$:$\beta$-$R_{3-6}$ where $R_{3-5}$ is —O—$R_{31}$ and $R_{3-6}$ is —O—$R_{32}$ where $R_{31}$ and $R_{32}$ are the same or different and are selected from the group consisting of $C_1$–$C_3$ alkyl and $R_{31}$ and $R_{32}$ are taken with the attached —O—C—O— to form a cyclic ketal of 5 or 6 atoms of the formula

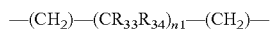

—(CH$_2$)—(CR$_{33}$R$_{34}$)$_{n1}$—(CH$_2$)— where $n_1$ is 0 or 1;

where $R_{33}$ and $R_{34}$ are the same or different and are —H and $C_1$–$C_3$ alkyl; $R_4$ is —H:—H; $R_6$ is $R_{6-5}$:$R_{6-6}$ where one of $R_{6-5}$ and $R_{6-6}$ is taken together with $R_5$ to form a second bond between the carbon atoms to which they are attached and the other of $R_{6-5}$ and $R_{6-6}$ is —H;

(IV) $R_3$ is $\alpha$-$R_{3-7}$:$\beta$-$R_{3-8}$ where $R_{3-7}$ is —O—$R_{31}$ and $R_{3-8}$ is —O—$R_{32}$ where $R_{31}$ and $R_{32}$ are as defined above; $R_4$ is $R_{4-7}$:$R_{4-8}$ where one of $R_{4-7}$ and $R_{4-8}$ is taken together with $R_5$ to form a second bond between the carbon atoms to which they are attached and the other of $R_{4-7}$ and $R_{4-8}$ is —H; $R_6$ is —H:—H;

where $R_9$, $R_{11}$ and $R_{17}$ are as defined above; with a reaction medium which has a pH of less than about 5. The conversion of the carboxylic acid (VI) to the corresponding 5,7-lactone (VII) is an equilibrium reaction. The lower the pH used for the reaction medium the more the equilibrium shifts toward the 5,7-lactone (VII), hence the desire to keep the pH less than 5 and preferably in the range of 1 thru 5. It is preferred to perform the reaction under anhydrous conditions; under anhydrous conditions it is preferred that the acid be a strong acid of $pK_a$ less than about 2. Useful strong acids include those selected from the group consisting of fluorosulfonic, chlorosulfonic, benzenesulfonic, p-toluenesulfonic, methanesulfonic, trifluoromethanesulfonic, trifluoroacetic, trichloroacetic, hydrochloric, sulfuric, phosphoric and nitric; it is preferred that the acid is benzenesulfonic, p-toluenesulfonic or methanesulfonic acid. Alternatively, the process can be performed using aqueous acid as the catalyst. Under these conditions it is preferred to perform the process in a two-phase system. The amount of acid used in not very important and can be present in an amount from catalytic to excess. Bases are also operable to catalyze the reaction of the carboxylic acid (VI) to the corresponding 5,7-lactone (VII) as long as they are used in a catalytic amount. Useful bases include those selected from the group consisting of hydroxide, bicarbonate, carbonate, DBU, DBN, DABCO, pyridine, p-dimethylaminopyridine, $Q_7$—COO$^-$ where $Q_7$ is —H, $C_1$–$C_3$ alkyl or -Φ, $(Q_3)_3$N where $Q_3$ is $C_1$–$C_3$ alkyl; preferred are hydroxide, bicarbonate, carbonate, triethylamine or pyridine. The solvents for the transformation of the carboxylic acid (VI) to the corresponding 5,7-lactone (VII) are helpful in effecting the equilibrium of the reaction. It is preferred to use a solvent in which the starting carboxylic acid (VI) is soluble and in which the 5,7-lactone (VII) is not soluble. That way the 5,7-lactone (VII) precipitates out as it is formed pushing the equilibrium towards the desired 5,7-lactone (VII). A preferred solvent is acetone. This reaction is performed from about 0° to about 25° and is complete in a few hours. Depending on the pH of the reaction medium and solvent used, ratios of <95/5 of carboxylic acid (VI)/5,7-lactone (VII) are obtained. Since this process step is an equilibrium reaction, the pH of the reaction medium helps control the final position of the equilibrium as is known to those skilled in the art.

A second process for producing a 5,7-lactone of formula (VII)

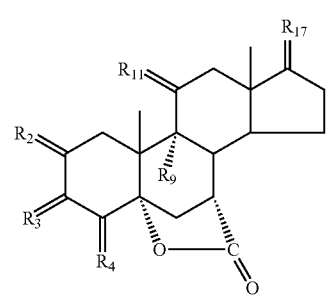

(VII)

where (Va) $R_2$ is —H:—H, $R_3$ is =O and $R_4$ is —H:—H;

where $R_9$, $R_{11}$ and $R_{17}$ are as defined above, comprises:

(1) contacting a carboxylic acid of formula (VI)

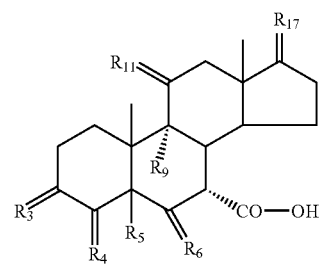

(VI)

where (I) $R_3$ is =O; $R_4$ is $R_{4-1}$:$R_{4-2}$ where one of $R_{4-1}$ and $R_{4-2}$ is —H and the other of $R_{4-1}$ and $R_{4-2}$ is taken together with $R_5$ to form a second bond between the carbon atoms to which they are attached; $R_6$ is —H:—H;

where $R_9$, $R_{11}$ and $R_{17}$ are as defined above; under anhydrous conditions with an anhydrous reaction medium of pH less than about 5. It is preferred that the reaction medium contains an acid which has a $pK_a$ of < about 4. Useful acids which have a $pK_a$ of < about 4 include those selected from the group consisting of fluorosulfonic, chlorosulfonic, benzenesulfonic, p-toluenesulfonic, methanesulfonic, trifluoromethanesulfonic, trifluoroacetic, trichloroacetic, hydrochloric, sulfuric, phosphoric and nitric. It is preferred that the acid is benzenesulfonic, p-toluenesulfonic or methanesulfonic. It is also preferred that the carboxylic acid (VI) is reacted with the acid in a two-phase system. The process also includes reacting the carboxylic acid (VI) with a catalytic amount of base. Useful bases include those selected from the group consisting of hydroxide, bicarbonate, carbonate, DBU, DBN, DABCO, pyridine, p-dimethylaminopyridine, $Q_7$—COO$^-$ where $Q_7$ is —H, $C_1$–$C_3$ alkyl or -Φ, $(Q_3)_3N$ where $Q_3$ is $C_1$–$C_3$ alkyl.

A third process for producing a 5,7-lactone of formula (VII)

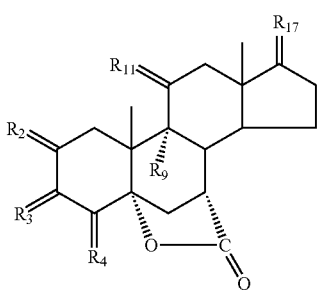

where
(Vc) $R_2$ is —H:—H, $R_3$ is —O—$R_{3a}$:—O—$R_{3b}$ where $R_{3a}$ and $R_{3b}$ the same and are $C_1$–$C_3$ alkyl or where $R_{3a}$ and $R_{3b}$ are taken together with the attached —O—C—O— to form a cyclic ketal of 5 or 6 atoms of the formula

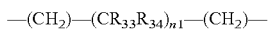

where $n_1$ is 0 or 1;
where $R_{33}$ and $R_{34}$ are the same or different and are —H and $C_1$–$C_3$ alkyl, and $R_4$ is —H: —H;
(VI) $R_2$ is —H:—H; $R_3$ is $R_{3c}$:$R_{3d}$ and $R_4$ is $R_{4c}$:$R_{4d}$ where one of $R_{3c}$ and $R_{3d}$ is taken with one of $R_{4c}$ or $R_{4d}$ to form a second bond between the carbon atoms to which they are attached and the other of $R_{3c}$ and $R_{3d}$ is $CH_3$—O— or $C_2H_5$—O—; and the other of $R_{4c}$ and $R_{4d}$ is —H; or
(VII) $R_2$ is $R_{2e}$:$R_{2f}$ and $R_3$ is $R_{3e}$:$R_{3f}$ where one of $R_{2e}$ and $R_{2f}$ is taken with one of $R_{3e}$ or $R_{3f}$ to form a second bond between the carbon atoms to which they are attached and the other of $R_{2e}$ and $R_{2f}$ is —H, and the other of $R_{3e}$ and $R_{3f}$ is $CH_3$—O— or $C_2H_5$—O—; or mixtures thereof,
where $R_9$, $R_{11}$ and $R_{17}$ are as defined above, comprises:
(1) contacting a carboxylic acid of formula (VI)

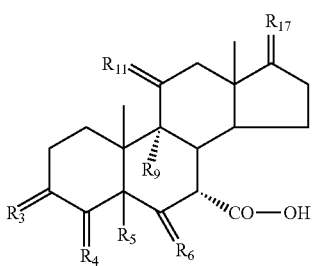

where
(III) $R_3$ is α-$R_{3-5}$:β-$R_{3-6}$ where $R_{3-5}$ is —O—$R_{31}$ and $R_{3-6}$ is —O—$R_{32}$ where $R_{31}$ and $R_{32}$ are the same or different and are selected from the group consisting of $C_1$–$C_3$ alkyl and
$R_{31}$ and $R_{32}$ are taken with the attached —O—C—O— to form a cyclic ketal of 5 or 6 atoms of the formula

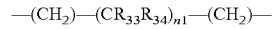

where $n_1$ is 0 or 1;
where $R_{33}$ and $R_{34}$ are the same or different and are —H and $C_1$–$C_3$ alkyl; $R_4$ is —H:—H; $R_6$ is $R_{6-5}$:$R_{6-6}$ where one of $R_{6-5}$ and $R_{6-6}$ is taken together with $R_5$ to form a second bond between the carbon atoms to which they are attached and the other of $R_{6-5}$ and $R_{6-6}$ is —H;
(IV) $R_3$ is α-$R_{3-7}$:β-$R_{3-8}$ where $R_{3-7}$ is 4-$R_{31}$ and $R_{3-8}$ is —O—$R_{32}$ where $R_{31}$ and $R_{32}$ are as defined above; $R_4$ is $R_{4-7}$:$R_{4-8}$ where one of $R_{4-7}$ and $R_{4-8}$ is taken together with $R_5$ to form a second bond between the carbon atoms to which they are attached and the other of $R_{47}$ and $R_{4-8}$ is —H; $R_6$ is —H:—H;
where $R_9$, $R_{11}$ and $R_{17}$ are as defined above; with at least a catalytic amount of acid. It is preferred that the acid have a $pK_a$ of < about 4 and are as discussed above.

The present invention includes a process for the preparation of a methyl ester of formula (VIII)

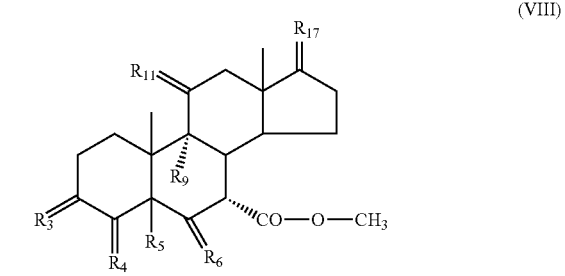

where
(I) $R_3$ is =O; $R_4$ is $R_{4-}$:$R_{4-2}$ where one of $R_{4-1}$ and $R_{4-2}$ is —H and the other of $R_{4-1}$ and $R_{4-2}$ is taken together with $R_5$ to form a second bond between the carbon atoms to which they are attached; $R_6$ is —H:—H;
where $R_9$, $R_{11}$ and $R_{17}$ are as defined above, which comprises:
(1) contacting a 5,7-lactone of the formula (VII)

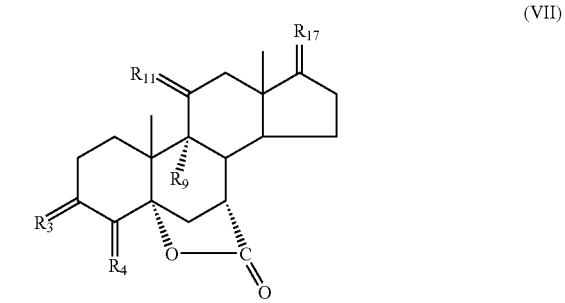

where $R_4$ is —H:—H and where $R_3$, $R_9$, $R_{11}$ and $R_{17}$ are defined above, with base, and
(2) contacting the reaction mixture of step (1) with a methylating agent. The base needs to be strong enough to open the 5,7-lactone (VII) but of the type that will not react with the methylating agent, a weak nucleophile. Useful bases include those selected from the group consisting of bicarbonate, carbonate, hydroxide and $R_{base}O^-$ where $R_{base}$ is $C_1$–$C_4$ alkyl. It is preferred that the base is bicarbonate. The amount of base required is from about 1 to about 1.5 equivalents. Useful methylating agents include those selected from the group consisting of dimethylsulfate, methyl iodide, methyl bromide, trimethylphosphate, dimethylcarbonate and methyl chloroformate; preferred is dimethylsulfate. The amount of methylating agent used should be the same as the number of equivalents of base used or a very slight excess over that. The preferred method of the process is to react it in a sequential manner in a two-step reaction with base first and then the methylating agent. If the reaction is performed all in one step, the base reacts with the methylating reagent necessitating the need for more base and more methylating agent. The more efficient way is to first react the 5,7-lactone (VII) with at least one equivalent of base, preferably from about 1 to about 1.5 equivalents and then to react the salt of the carboxylate acid (VI) which is formed with the methylating agent. The solvent used will depend on the nature of the base used. If it is water soluble, such as bicarbonate or hydroxide, then a mixture of water and a water miscible organic solvent is preferred. These water miscible organic solvents include, methanol, ethanol, isopropanol, acetone, THF and DMF. If the base is water soluble and the solvent is a mixture of water and a water immiscible solvent, then a phase transfer catalyst, such as tetrabutylammonium bisulfate or tributylmethylammonium chloride is used. If the base is soluble in a water immiscible organic solvent, one that will also dissolve the 5,7-lactone (VII), then a water-immiscible organic solvent is suitable. The reaction temperature is dependent on the reactivity of the methylating agent. If an agent such as dimethylcarbonate is used the reaction will go slow and heat up to about 150° may be necessary. On the other hand, if a more reactive agent such as dimethylsulfate is used the reaction goes in about 1 hour at 40°. While in theory one equivalent of base and one equivalent of methylating agent should be sufficient, in practice more than one equivalent is needed for the optimum reaction conditions.

The 5,7-lactone (VII) can be transformed to the (salt of the) corresponding carboxylic acid (VI) by contacting the 5,7-lactone of formula (VII), with a reaction medium which as a pH>7. The reaction is similar to the transformation of the 5,7-lactone (VI) to the methyl ester (VIII) except that no methylating agent is used. Since only base is used, the product produced is the salt of the carboxylic acid (VI). Further, since no methylating agent is present, the amount of base used is not critical. If the acid form of the carboxylic acid (VI), is desired the salt form can be acidified to produced the corresponding acid form of the carboxylic acid (VI) as is known to those skilled in the art.

There are numerous alternative routes using the present invention as set forth in CHART A as will be explained below and is known to those skilled in the art. For example, the steroid A-ring can be protected, as compound (I-P), see CHART B and the explanation below, during the transformation of (I) to (II) or used in the unprotected form (I). Further, the C- and D-rings can have a variety of functionality during the various steps of the process. The C-ring functionality includes, for example, 9α-hydroxy, 9α-O-(HYDROXY PROTECTING GROUP), 9α-F, 11-keto, 11-saturated, 11α-hydroxy, 11α-O-(HYDROXY PROTECTING GROUP), 11β-hydroxy, 11β-O-(HYDROXY PROTECTING GROUP), $\Delta^{9(11)}$- and 9α,11α-epoxy. The D-ring functionality includes, for example, 17-keto, 17β-hydroxy, 17α-ethynyl-17β-hydroxy, 17α-cyano-17β-hydroxy, 17α-C≡C—CH$_2$—O—(—H or substitutedsilyl)-17β-OH, 17α-C≡C—CH$_2$—O-(HYDROXY PROTECTING GROUP)-17β-OH, 17α-CH$_2$—CH$_2$—CH$_2$—OH-17, —OH, 17α-CH$_2$—CH$_2$—CH$_2$—O-(HYDROXY PROTECTING GROUP)-17β-OH, 17α-hydroxy-17β-CO—CH$_3$, 17β-CO—CH$_2$—OH, 17β-CO—CH$_2$—O—CO—(CH$_2$)$_{0-3}$—CH$_3$; 17β-O—CH$_2$-17α resulting in a three member epoxide, γ-lactone and —O—CH(OR$_{17-9}$)—CH$_2$—CH$_2$ . . . where the bond from the oxygen (—O) is one of the four bonds at C-17 in the β-configuration and the bond from the methylene group (CH$_2$ . . . ) is another of the four bonds at C-17 in the α-configuration to form a 5 member heterocycle containing one oxygen atom, where $R_{17-9}$ is —H or $C_1$–$C_3$ alkyl. However, the D-ring functionality for the compounds of the processes of claims 539, 548 and 556 does not include $R_{17-2}$ being hydroxyl. HYDROXY PROTECTING GROUPs are well known to those skilled in the art. The same HYDROXY PROTECTING GROUPs are operable at C-9, C-11 and C-17 and are selected from the group consisting of: —Si(—CH$_3$)$_3$, —Si(—CH$_2$—CH$_3$)$_3$, —CO—CH$_3$, —CO—H and —SiH(CH$_3$)$_2$.

At some point the A-ring, if it is not already the required $\Delta^4$-3-keto functionality, must be transformed to the $\Delta^4$-3-keto functionality. Likewise, with the C-ring, if it is not already the required 9α,11α-epoxide functionality, it must be transformed to the 9α,11α-epoxide. Similarly, if the D-ring is not already the required γ-lactone, it must be transformed to the γ-lactone. However, those transformations can take place either before, during or after various other processes and/or steps of CHART A. It is preferred to start with the A-ring with $\Delta^4$-3-keto functionality, the C-ring with $\Delta^{9(11)}$-functionality and the D-ring as the γ-lactone. With regard to the C-ring, it is preferred to maintain the $\Delta^{9(11)}$-functionality throughout the process of the invention until the —CO—O—CH$_3$ group is fully synthesized at the 7α-position and then transform the $\Delta^{9(11)}$-functionality to the corresponding 9α,11α-epoxide. With regard to the C-ring one could start with a 11-keto functionality and at some point in the process reduce it to the 11α-hydroxy functionality and then at some later point dehydrate the 11α-hydroxy functionality to the corresponding $\Delta^{9(11)}$-olefin functionality by either the processes of EXAMPLEs 18–20 using PCl$_5$ or by the process of EXAMPLE 31 using N-(1,1,2,2,3,3,3) hexafluoropropyldiethyl-amine which is known as Ishikawa reagent. There is a thorough discussion below as to how the dehydration of an 11α-hydroxy steroid should be performed using the Ishakawa reagent to produce the corresponding $\Delta^{9(11)}$-olefin. If the dehydration of the 11α-hydroxy to the corresponding $\Delta^{9(11)}$-olefin takes place with a 5'-methyl-2'-furyl substituent at C-7α, with a formula (II) compound, it appears PCl$_5$ is preferred, but if the dehydration takes place on the methyl ester (VII), then the Ishikawa reagent is preferred. The $\Delta^{9(11)}$-olefin is then converted to the desired 9α,11α-epoxide functionality by means well known to those skilled in the art. Likewise, with regard to the D-ring, one need not start with the γ-lactone in the $\Delta^{4,6}$-3-keto steroid or ketal thereof (I) starting material. One could start with 17-keto or 17β-hydroxy, etc and then at a desired point covert the starting D-ring 17-functionality to the desired γ-lactone. The preferred process including what functionality is desired to start with, and where the conversions are made, is set forth in CHART E. In short, it is desired to start with the same functionality as is desired in the end product for the A-ring and D-rings. It is preferred to start with the C-ring having the $\Delta^{9(11)}$-olefin functionality which is transformed to the desired 9α,11α-epoxide functionality after the 7α-substitutent is finalized as —CO—O—CH₃. However, as explained above and is known to those skilled in the art, there are numerous alternative ways of preparing eplerenone by the process of CHART A starting with different functionality in the A-, C- and D-rings.

CHART B discloses a process to produce the protected Δ⁴,⁶-ketal steroid (I-P), from the corresponding Δ³,⁵-3-alkyl enol ethers which are readily available from the corresponding Δ⁴-3-keto steroids by processes known to those skilled in the art. It is preferred use the unprotected Δ⁴,⁶-3-keto steroid (I) as the starting material in the process of CHART A. However, steroidal Δ⁴,⁶-3-ketals (I-P) can also be used as the starting material of the process of CHART A. In the process of CHART B, the Δ⁴,⁶-3-ketal steroid (I-P)

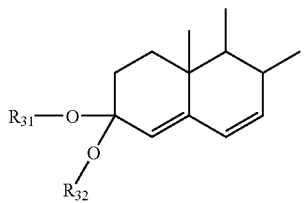

(I-P)

where R₃₁ and R₃₂
(1) the same or different and are C₁–C₃ alkyl, and
(2) taken with the attached —O—C—O— to form a cyclic ketal of 5 or 6 atoms of the formula

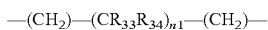

—(CH₂)—(CR₃₃R₃₄)$_{n1}$—(CH₂)— where n₁ is 0 or 1;
where R₃₃ and R₃₄ are the same or different and are
—H,
C₁–C₃ alkyl,
is produced from the corresponding Δ³,⁵-3-alkyl enol ether

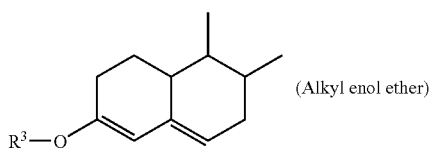

(Alkyl enol ether)

where R³ is
C₁–C₃ alkyl,
CH₃—CO—,
Φ-CO— or
R$_{Si-1}$R$_{Si-2}$R$_{Si-3}$Si— where R$_{Si-1}$, R$_{Si-2}$ and R$_{Si-3}$ are the same or different and are C₁–C₄ alkyl; by contacting the Δ³,⁵-3-alkyl enol ether (Alkyl enol ether) with a hydride abstractor and an alcohol selected from the group consisting of alcohols of the formula:
(a) R₃₁—OH, where R₃₁ is as defined above,
(b) R₃₂—OH, where R₃₂ is as defined above,
(c) HO—(CH₂)—(CR₃₃R₃₄)$_{n1}$—(CH₂)—OH where n₁, R₃₃ and R₃₄ are as defined above,
(d) HO—CH₂—CH₂—OH, by (1) contacting the Δ³,⁵-3-enol ether (3-alkyl enol ether).

Useful hydride abstractors include those selected from the group consisting of
DDQ,
p-chloranil,
o-chloranil,
Mn⁺³, Mn⁺⁷, Pb⁺⁴, Pd⁺², Ru⁺⁸, Cr⁺⁶,
o-iodoxybenzoic acid,
o-iodoxybenzoic acid complex with DMSO,
o-iodoxybenzoic acid complex with 4-methoxypyridine-N-oxide,
N-methylmorpholine-N-oxide,
trimethylamine-N-oxide,
iodic acid (HIO₃),
iodine pentoxide (I₂O₅),
ceric ammonium nitrate,
iodosobenzene,
iodobenzenebistrifluoroacetate,
iodobenzenediacetate,
tritylfluoroborate, and by electrochemical oxidation with a catalytic amount of a hydride abstractor. It is preferred that the hydride abstractor is p-chloranil or DDQ, more preferably DDQ. One equivalent of the hydride abstractor is required; more is not harmful, just wasteful. It is preferred that the alcohol is neopentylglycol also known as dimethylpropyleneglycol or 2,2-dimethyl-1,3-propanediol. The solvent needs to dissolve the 3-alkyl enol ether (3-alkyl enol ether) starting material. Suitable solvents include methylene chloride, acetonitrile, THF, and the alike. The reaction is operable in the temperature range of about −78° to about 40°, preferred is about −15°. The reaction is very rapid and is complete in a few minutes at −15°. The entire process is preferably performed under essentially anhydrous conditions. The term "hydride abstractor" as used herein means the reagent effects the net removal of one of the hydrogen atoms at C-7 of the 3-dienol ether, and does not imply any mechanism by which this removal occurs. It is preferred that the a Δ⁴,⁶-ketal (I-P) is selected from the group consisting of 17β-hydroxypregna-4,6,9(11)-trien-3-one-21-carboxylic acid, γ-lactone, cyclic 3-(2',2'-dimethyl-1',3'-propanediyl ketal), 17β-hydroxypregna-4,6,9(11)-trien-3-one-21-carboxylic acid, γ-lactone, cyclic 3-ethanediyl ketal.

CHART C discloses that the 7α-substituted steroid (II) can also be transformed to the corresponding cis-oxyenedione (X-cis) by (1) contacting the 7α-substituted steroid (II) with ozone in the presence of a C₁–C₄ alcohol and (2) contacting the mixture of step (1) with a hydroperoxy-deoxygenating agent. The preferences for R₇₋₁, X₁ R$_b$, R$_c$, R$_d$ and the other variable substituents are as set forth above as previously stated. The 7α-substituted steroid (II) is dissolved in a suitable C₁–C₄ alcohol, or mixture thereof. It is preferred that the C₁–C₄ alcohol is a C₁ and C₃ alcohols; it is more preferred the alcohol is a C₁ alcohol. Cosolvents such as methylene chloride can also be used if necessary. The nature of the solvent/co-solvent is not critical as long as it will dissolve the reactants at the cold temperature at which the process is performed. The nature of the alcohol is not critical as it is eventually lost from the steroid molecule. The reaction temperatures can be as low as about −100° up to about 40°. It is preferred that the temperature be from about −78' to about −20°; it is more preferred that the temperature be about −50°. Ozone is passed thru the reaction mixture as is known to those skilled in the art until the process of step (1) is complete. The course of the reaction is monitored as is known those skilled in the art. When the reaction of step (1) is complete, the reaction mixture of step (1) is contacted with a hydroperoxy-deoxygenating agent. It is preferred that the hydroperoxy-deoxygenating agent is trimethylphosphite. It is realized that for other processes of this invention the preferred hydroperoxy-deoxygenating agent was dimethylsulfide, but here the preferred agent is trimethylphosphite. The reaction mixture is then slowly permitted to warm to 20–25°. The reaction will proceed rapidly when it reaches the correct temperature for the particular 7α-substituted steroid (I). The cis-oxyenedione (X-cis) product can be carried along without isolation and purification if desired.

CHART C further discloses that the cis-oxyenedione (X-cis) can be transformed to the corresponding trans-oxyenedione (X-trans). The process is performed in the same manner and same way that the cis-enedione (III-cis), of CHART A, was transformed to the corresponding trans-enedione (III-trans).

The cis-oxyenedione (X-cis) or the trans-oxyenedione (X-trans), or a mixture thereof, can be transformed to the corresponding hydroperoxy compound (IV-OOH), and/or hydroxy compound (IV-OH), and/or biscarbonyl compound (V) and/or carboxylic acid (VI) or mixture thereof in the same manner and same way as the cis-enedione (III-cis) or the trans-enedione (III-trans), or a mixture thereof, was transformed to the corresponding hydroperoxy compound (IV-OOH), and/or hydroxy compound (IV-OH), and/or biscarbonyl compound (V) and/or carboxylic acid (X) or mixture thereof. The hydroperoxy compound (IV-OOH), and/or hydroxy compound (IV-OH), and/or biscarbonyl compound (V) and/or carboxylic acid (X) or mixture thereof are then transformed to eplerenone (IX) in the same manner and same was as previously discussed for the process of CHART A.

The cis-oxyenedione (X-cis) or the trans-oxyenedione (X-trans), or a mixture thereof, can be transformed to the corresponding carboxylic acid (VI) by reaction with an oxidatively cleaving agent in the same manner and same way as the hydroxy compound (IV-OH), and/or biscarbonyl compound (V) are transformed to the corresponding carboxylic acid (VI).

CHART D sets forth the preferred process of the invention (when $R_{7-1}$ is -A1) with regard to the steroid A-/B-ring, that the steroid A-ring is not protected. However, given the different variable substituents of the steroid C- and D-rings and combinations of variable substituents possible, in some cases it may be preferred to protect the steroid A-ring as would be apparent to one skilled in the art. But in general, it is preferred that the steroid A-ring not be protected and the preferred process be that of CHART D.

CHART E sets forth the preferred process of the invention with the preferred variable substituents for each intermediate for the conversion of the $\Delta^{4,6}$-3-keto steroid (1) to eplerenone (IX).

CHART F discloses the reversible nature of the conversion of the carboxylic acid (VI) with the 5,7-lactone (VII).

CHART G discloses the general process of the invention when the adduct —$R_{7-1}$ is the cyclic adduct (-A2). The 7α-substituted steroid (II) is formed in the same manner as discussed above for CHART A when the adduct is (-A1). Then the 7α-substituted steroid (II) where $R_{7-1}$ is (-A2) is reacted in the same way, with the same reagents as used in CHART A for (-A1) to give intermediates of the same type as the intermediates of CHART A for adduct (-A1). The processes of CHARTs A and G are analogous, the reactants are the same and used in the same order. The intermediates produced are either isomers or homologs of each other.

CHART H discloses the general process of the invention when the adduct $R_{7-1}$ is (-B), (-C), (-D1), (-D2) and (-D3). The process of CHART H is a two step process. The first step of the process is to transform the $\Delta^{4,6}$-3-keto steroid or ketal thereof (I) starting material to the corresponding 7α-substituted steroid (II) where $R_{7-1}$ is a substituent selected from the group consisting of

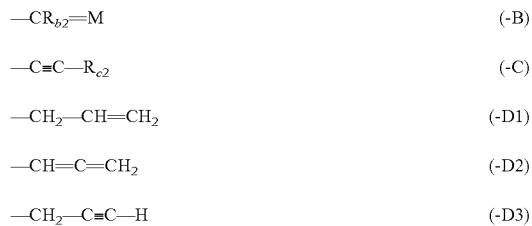

The second step is oxidative cleavage of the 7α-substitutent to give a carboxylic acid functionality, —CO—OH of the carboxylic acid (VI). In the olefinic substituent (-B), "M" is a group which forms a double bond with carbon and is restricted to carbon, nitrogen and oxygen. The substituent $R_{b2}$ is a group that can be transformed into a hydroxyl group by either oxidation or hydrolysis. With the acetylenic substituent (-C), the group $R_{c2}$ can be virtually any group since it is ultimately lost when the triple bond is cleaved to a carboxylic acid (VI). Likewise with the three-carbon unsaturated substituents (-D1), (-D2) and (-D3), two of the three carbon atoms are cleaved oxidatively, leaving a carboxylic acid group. In transforming the $\Delta^{4,6}$-3-keto steroid or ketal thereof (I) starting material to the corresponding 7α-substituted steroid (II), the $\Delta^{4,6}$-3-keto steroid or ketal thereof (I) starting material is reacted with the nucleophile selected from the group consisting of (d) of the formula (B)

(e) of the formula (C)

(f) of the formulas (D1, D2 and D3)

where $R_a$, $E_1$, $E_2$, M are as defined above, in the presence of:
(1) a Lewis Acid,
(2) a proton acid with a $pK_a$ of < about 5 or
(3) a salt of a secondary amine of the formula

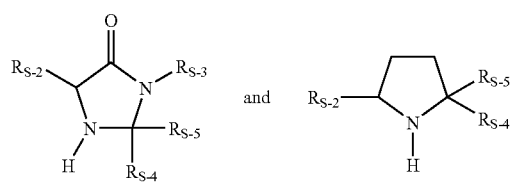

with an acid of $pK_a$ of < about 2. The Lewis acid both accelerates the conjugate addition and favors formation of the 7α-stereochemistry.

Adducts (-B) and (-C) are transformed into —CO—OH of carboxylic acid (VI) by treatment with one or more oxidizing agents. The oxidizing agent(s) must be capable of cleaving the C=M double bond to a carbon-oxygen double bond, cleaving the C—$R_{b2}$ single bond to a carbon-oxygen single bond, and cleaving the carbon-carbon triple bond to carboxylic acid. The choice of oxidizing agent(s) depends on the inherent difficulty of oxidation of the substituent —$CR_{b2}$=M or —C≡C—$R_{c2}$. The greater the difficulty of oxidation, the stronger the oxidizing agent that will be required. Suitable oxidizing agents include ozone, singlet oxygen, triplet oxygen, hydrogen peroxide, hydroperoxides, percarboxylic acids, hypohalites, and the like. In the case of 2-methylfuran adduct (II), transformation into carboxylic acid (VI) is preferably accomplished by treatment with potassium hypobromite followed by ozone followed by dimethylsulfide followed by hydrogen peroxide.

The allyl adduct (-D1) is transformed into —CO—OH of the carboxylic acid (VI) by double bond isomerization to —CH═CH—$CH_3$ followed by ozonization with an oxidative work-up (such as sodium chlorite). The double bond isomerization can be accomplished by any of the following reagents, rhodium trichloride in ethanol at reflux, HRuCl[P(-Φ)$_3$]$_3$ at about 90°, LiNH(CH$_2$)$_3$NH$_2$ (lithium 1,3-diaminopropane) at 20–25°, PdCl$_2$(Φ-CN)$_2$ in toluene at about 80°, HRh(CO)[P(-Φ)$_3$]$_3$ at 20–25°, ClRh[P(-Φ)$_3$]$_3$ in toluene at reflux, Cl$_2$Ru[P(-Φ)$_3$]$_3$ at 100° and cobalt chloride/sodium borohydride/P(-Φ))$_3$ at about −18°.

The propargyl adduct (-D2) is transformed into the —CO—OH functionality of the carboxylic acid (VI) by base or transition metal-catalyzed isomerization to adduct (-C) when $R_{c2}$ is $C_1$ alkyl, which is cleaved by the method discussed above. Suitable bases for isomerization of (-D2) to (-C) include sodium amide in ammonia or THF, potassium 3-aminopropylaminde (known as "KAPA") in THF, potassium hydroxide in ethylene glycol at about 150°, potassium t-butoxide in DMSO or t-butanol, or sodium or potassium hydride in DMF or THF. Suitable transition metal catalysts include Yb[Φ$_2$C═N-Φ](HMPA)$_4$ and HCo(N$_2$)[P(-Φ)$_3$]$_3$.

The allenyl adduct (-D3) is transformed into the —CO—OH functionality of the carboxylic acid (VI) by ozonization with an oxidative work-up (such as sodium chlorite).

The present invention includes a four-step process for the transformation of a 7α-substituted steroid (II) to the corresponding carboxylic acid (VI) product. The four steps are (1) ring opening, (2) ozonolysis, (3) reaction with a hydroperoxy deoxygenating agent and (4) reaction with an oxidatively cleaving agent. The four-step process of the invention produces better yields of the carboxylic acid (VI) than expected based on prior art process steps. The carboxylic acid (VI) is obtained by:

(1) contacting the 7α-substituted steroid of formula (II) with an agent selected from the group consisting of:
  (a) a halogenating agent in the presence of water and a base whose conjugate acid has a pK$_a$ of > about 8,
  (b) an oxygen donating agent,
  (c) electrochemical oxidation,
  (d) a quinone in the presence of water or
  (e) nonquinone oxidants; and
(2) contacting the reaction mixture of step (1) with ozone in the presence of an alcohol of the formula $R_{7-2}$—OH;
(3) contacting the reaction mixture of step (2) with a hydroperoxy deoxygenating agent and
(4) contacting the reaction mixture of step (3) with an oxidatively cleaving agent. Each of these steps was thoroughly discussed above when the steps of the process were discussed individually. This process combines those same steps and they are practiced in the same manner and same way as discussed above.

The present invention includes a three-step process for the transformation of a 7α-substituted steroid (II) to the corresponding carboxylic acid (VI) product, see EXAMPLE 34, Step (1). The three steps are (1) ozonolysis, (2) reaction with a hydroperoxy deoxygenating agent and (3) reaction with an oxidatively cleaving agent. The three-step process of the invention is a process to prepare the carboxylic acid (VI) which comprises:

(1) contacting a 7α-substituted steroid (II) with ozone in the presence of an alcohol of the formula $R_{7-2}$—OH;
(2) contacting the reaction mixture of step (1) with a hydroperoxy deoxygenating agent and
(3) contacting the reaction mixture of step (2) with an oxidatively cleaving agent. Each of these steps was thoroughly discussed above when the steps of the process were discussed individually. This process combines those same steps and they are practiced in the same manner and same way as discussed above. The carboxylic acid (VI) can be readily transformed to its tautomer-like the bislactone (VII) by contacting with an acid, see EXAMPLE 34, Step (2). In the process of the invention it is the carboxylic acid (VI) which is transformed to the methyl ester (VIII) and ultimately to eplerenone (IX). It is possible to isolate and purify this carboxylic acid (VI) by crystallization. However, one runs the risk that it will isomerize to the bislactone (VII) which is more thermodynamically stable. Therefore, as a practical matter it is preferable not to stop at the end of EXAMPLE 34, Step (1) but carry on thru the reaction mixture and isolate and crystallize the bislactone (VII). Hence, it is easier and preferable to carry the process exemplified in EXAMPLE 34 on thru Step (2), purify the bislactone (VII) obtained and then convert the bislactone (VI) back to the carboxylic acid (VI) for transformation to the methyl ester (VIII).

Eplerenone (IX) is a pharmaceutical agent useful for the treatment of hyperaldosteronism, edema, hypertension and congestive heart failure, see U.S. Pat. No. 4,559,332.

The present invention also includes a novel process to transform 11α-hydroxy steroids to the corresponding $\Delta^{9(11)}$-steroids. The $\Delta^{9(11)}$-functionality is very useful in producing eplerenone (IX) because it is readily transformed to the corresponding 9α,11α-epoxide functionality of eplerenone (IX).

The 11α-hydroxy steroid (CIV) starting materials are known to those skilled in the art. More particularly, the 11α-hydroxy-17-lactone (CI), 11α,17β-dihydroxypregn-4-en-3-one-7α,21-dicarboxylic acid, γ-lactone, methyl ester, is known, see, *Drugs of the Future*, 24(5), 488–501 (1999), compound (VI).

For the 11α-hydroxy steroids (CIV) it is preferred that the steroid A-ring is:

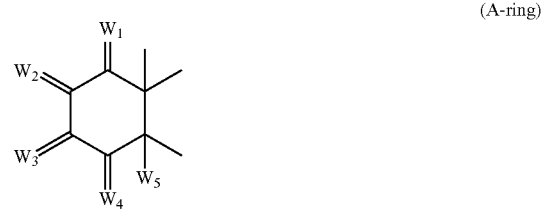

(A-ring)

(1) $W_1$ is —H:—H and $W_2$ is —H:—H or $W_1$ is $W_{1-1}$:$W_{1-2}$ and $W_2$ is $W_{2-1}$:$W_{2-2}$ where one of $W_{1-1}$ or $W_{1-2}$ is taken together with one of $W_{2-1}$ or $W_{2-2}$ to form a second bond between the carbon atoms to which they are attached and the other or $W_{1-1}$ or $W_{1-2}$ and $W_{2-1}$ or $W_{2-2}$ is —H; $W_3$ is ═O, $W_4$ is $W_{4-1}$:$W_{4-2}$ where one of $W_{4-1}$ and $W_{4-2}$ is taken together with $W_5$ to form a second bond between the carbon atoms to which they are attached and the other of $W_{4-1}$ and $W_{4-2}$ is —H;

(2) $W_3$ is =O, $W_4$ is —H:—H and $W_5$ is in the α-orientation and is . . . O—CO— (attached at $C_7$ to form a 5,7-lactone) and where $W_1$ and $W_2$ are as defined above;

(3) $W_3$ is —O—$W_{3-3}$:—O—$W_{3-4}$; $W_4$ is $W_{4-3}$:$W_{4-4}$, where one of $W_{4-3}$ and $W_{4-4}$ is taken together with $W_5$ to form a second bond between the atoms to which they are attached and the other of $W_{4-3}$ and $W_{4-4}$ is —H; $W_{3-3}$ and $W_{3-4}$ are:
(a) the same or different and are $C_1$–$C_5$ alkyl,
(b) taken together to form a cyclic moiety selected from the group consisting of:
(i) —$CH_2$—$CH_2$—,
(ii) —$CH_2$—$CH_2$—$CH_2$—,
(iii) $CH_2$—$C(CH_3)_2$—$CH_2$—; and where $W_1$ and $W_2$ are as defined above;

(4) $W_3$ is —O—$W_{3-3}$:—O—$W_{3-4}$; $W_4$ is —H:—H; $W_5$ forms a second bond between $C_5$ and $C_6$; $W_{3-3}$ and $W_{3-4}$ are as defined above:

(5) $W_3$ is $W_{3-5}$:$W_{3-6}$; where
(a) one of $W_{3-5}$ and $W_{3-6}$ is —H and the other of $W_{3-5}$ and $W_{3-6}$ is:
(i) —O—$W_{3-5A}$ where $W_{3-5A}$ is $C_1$–$C_3$ alkyl,
(ii) —O—CO—$W_{3-5A}$ where $W_{3-5A}$ is as defined above,
(iii) —N($W_{3-5A}$)$_2$ where $W_{3-5A}$ is as defined above,
(iv) piperazinyl,
(v) morpholinyl,
(vi) piperidinyl,
(b) $W_{3-5}$ and $W_{3-6}$ are taken together with the carbon atom to which they are attached to form a cyclic moiety including:
(i) —O—$CH_2$—$CH_2$—O—,
(ii) —O—$CH_2$—$CH_2$—$CH_2$—O—,
(iii) —O—$CH_2$—$C(CH_3)_2$—$CH_2$—O— and where $W_4$ is —H:—H; $W_5$ forms a second bond between $C_5$ and $C_6$;

(6) $W_3$ is $W_{3-7}$:$W_{3-8}$ and where $W_4$ is $W_{4-7}$:$W_{4-8}$ where
(a) one of $W_{3-7}$ and $W_{3-8}$ is:
(i) —O—$W_{3-7A}$ where $W_{3-7A}$ is $C_1$–$C_3$ alkyl,
(ii) —O—CO—$W_{3-7A}$ where $W_{3-7A}$ is as defined above,
(iii) —N($W_{3-7A}$)$_2$ where $W_{3-7A}$ is as defined above,
(iv) piperazinyl,
(v) morpholinyl,
(vi) piperidinyl, and where the other of $W_{3-7}$ and $W_{3-8}$ is taken together with one of $W_{4-7}$ and $W_{4-8}$ to form a second bond between the carbon atoms to which they are attached and the other of $W_{4-7}$ and $W_{4-8}$ is —H; $W_5$ forms a second bond between $C_5$ and $C_6$;

(7) $W_3$ is α-$W_{3-9}$:β-$W_{3-10}$; where $W_{3-9}$ is —H and $W_{3-10}$ is:
(a) —O—CO—$W_{3-10A}$ where $W_{3-10A}$ is $C_1$–$C_3$ alkyl,
(b) —O—CO—O—$W_{3-10B}$ where $W_{3-10A}$ is
(i) $C_1$–$C_4$ alkyl,
(ii) -Φ optionally substituted with one thru three $C_1$–$C_3$ alkyl, g-F, —Cl, —Br, —I, $C_1$–$C_3$ alkoxy,
(iii) —$CH_2$-Φ where Φ is optionally substituted with one thru three $C_1$–$C_3$ alkyl, —F, —Cl, —Br, —I, $C_1$–$C_3$ alkoxy; where $WR_4$ is —H:—H; and $W_5$ forms a second bond between the carbon atoms at $C_5$ and $C_6$; and where $W_1$ and $W_2$ are as defined above;

(8) $W_3$ is α-$W_{3-9}$:β-$W_{3-10}$; where $W_4$ is $W_{4-9}$:$W_{4-10}$ where $W_{3-9}$ and $W_{3-10}$ are as defined above; where one of $W_{4-9}$ and $W_{4-10}$ taken together with $W_5$ forms a second bond between the atoms to which they are attached and the other of $W_{4-9}$ and $W_{4-10}$ is —H; and where $W_1$ and $W_2$ are as defined above.

It is more preferred that the steroid A-ring functionality be:

(1) $W_1$ is —H:—H and $W_2$ is —H:—H or $W_1$ is $W_{1-1}$:$W_{1-2}$ and $W_2$ is $W_{2-1}$:$W_{2-2}$ where one of $W_{1-1}$ or $W_{1-2}$ is taken together with one of $W_{2-1}$ or $W_{2-2}$ to form a second bond between the carbon atoms to which they are attached and the other or $W_{1-1}$ or $W_{1-2}$ and $W_{2-1}$ or $W_{2-2}$ is —H; $W_3$ is =O, $W_4$ is $W_{4-1}$:$W_{4-2}$ where one of $W_{4-1}$ and $W_{4-2}$ is taken together with $W_5$ to form a second bond between the carbon atoms to which they are attached and the other of $W_{4-1}$ and $W_{4-2}$ is —H;

(7) $W_3$ is α-$W_{3-9}$:β-$W_{3-10}$; where $W_{3-9}$ is —H and $W_{3-10}$ is:
(b) —CO—$W_{3-10A}$ where $W_{3-10A}$ is $C_1$–$C_3$ alkyl,
(c) —CO—O—$W_{3-10A}$ where $W_{3-10A}$ is
(i) $C_1$–$C_4$ alkyl,
(ii) -Φ optionally substituted with one thru three $C_1$–$C_3$ alkyl, —F, —Cl, —Br, —I, $C_1$–$C_3$ alkoxy,
(iii) —$CH_2$-Φ where Φ is optionally substituted with one thru three $C_1$–$C_3$ alkyl, —F, —Cl, —Br, —I, $C_1$–$C_3$ alkoxy; where $WR_4$ is —H:—H; and $W_5$ forms a second bond between the carbon atoms at $C_5$ and $C_6$; and where $W_1$ and $W_2$ are as defined above.

It is even more preferred that the steroid A-ring functionality be:

(1) $W_1$ is —H:—H and $W_2$ is —H:—H or $W_1$ is $W_{1-1}$:$W_{1-2}$ and $W_2$ is $W_{2-1}$:$W_{2-2}$ where one of $W_{1-1}$ or $W_{1-2}$ is taken together with one of $W_{2-1}$ or $W_{2-2}$ to form a second bond between the carbon atoms to which they are attached and the other or $W_{1-1}$ or $W_{1-2}$ and $W_{2-1}$ or $W_{2-2}$ is —H; $W_3$ is =O, $W_4$ is $W_{4-1}$:$W_{4-2}$ where one of $W_{4-1}$ and $W_{4-2}$ is taken together with $W_5$ to form a second bond between the carbon atoms to which they are attached and the other of $W_{4-1}$ and $W_{4-2}$ is —H;

For the 11α-hydroxy steroids (CIV), it is preferred that the steroid D-ring is:

(D-ring)

where $W_{17}$ is:
(1) =O,
(2) α-$W_{17-1}$:β-$W_{17-2}$ where:
(a) $W_{17-1}$ and $W_{17-2}$ are taken together with the attached carbon atom to form an epoxide of the formula . . . $CH_2$—O—,
(b) $W_{17-1}$ and $W_{17-2}$ are taken together with the attached carbon atom to form a lactone of the formula . . . $CH_2$—$CH_2$—CO—O—;

(3) α-$W_{17-3}$:β-$W_{17-4}$ where
  (a) $W_{17-3}$ is:
    (i) —H,
    (ii) —O—CO—$W_{17-3A}$ where $W_{17-3A}$ is —H or —CO—$W_{17-3B}$ where $W_{17-3B}$ is $C_1$–$C_4$ alkyl or -Φ and
  (b) $W_{17-4}$ is —CO—$CH_3$;
(4) α-$W_{17-5:0}$-$W_{17-6}$ where
  (a) $W_{17-5}$ is:
    (i) —O—CO—$W_{17-5A}$ where $W_{17-5A}$ is $C_1$–$C_4$ alkyl or -Φ,
  (b) $W_{17-6}$ is:
    (i) —CO—$CH_2$—O—$W_{17-6A}$ where $W_{17-6A}$ is $C_1$–$C_4$ alkyl or -Φ.

For the eplerenone-type compounds, it is preferred that $W_{17}$ is:
(1) =O,
(2) α-$W_{17-1}$:β-$W_{17-2}$ where:
  (a) $W_{17-1}$ and $W_{17-2}$ are taken together with the attached carbon atom to form an epoxide of the formula . . . $CH_2$—,
  (b) $W_{17-1}$ and $W_{17-2}$ are taken together with the attached carbon atom to form a lactone of the formula . . . $CH_2$—$CH_2$—CO—O—.

It is more preferred that for the eplerenone-type compounds that $W_{17}$ is:
(1) =O,
(2) α-$W_{17-1}$:β-$W_{17-2}$ where:
  (b) $W_{17-1}$ and $W_{17-2}$ are taken together with the attached carbon atom to form a lactone of the formula . . . $CH_2$—$CH_2$—CO—O—.

For the progesterones and hydroxyprotesterones it is preferred that that $W_{17}$ is:
(3) α-$W_{17-3}$:β-$W_{17-4}$ where
  (a) $W_{17-3}$ is:
    (i) —H,
    (ii) —O—CO—$W_{17-3A}$ where $W_{17-3A}$ is —H or —CO—$W_{17-3B}$ where $W_{17-3B}$ is $C_1$–$C_4$ alkyl or -Φ and
  (b) $W_{17-4}$ is —CO—$CH_3$.

For the corticoids it is preferred that $W_{17}$ is:
(4) α-$W_{17-5}$:β-$W_{17-6}$ where
  (a) $W_{17-5}$ is:
    (i) —O—CO—$W_{17-5A}$ where $W_{17-5A}$ is $C_1$–$C_4$ alkyl or -Φ,
  (b) $W_{17-6}$ is:
    (i) —O—$CH_2$—O—$W_{17-6A}$ where $W_{17-6A}$ is $C_1$–$C_4$ alkyl or -Φ.

The preferred combinations of steroid A-, B- and D-rings, especially for the eplerenone-type compounds, includes the ring systems set forth in CHART C. The 11α-hydroxy steroids (CIV) of CHART C are known to those skilled in the art or can be readily prepared by known methods from known compounds.

In the process of the present invention the 11α-hydroxy-17-lactones (CI) or 11α-hydroxy steroids (CIV) starting material is contacted with a N-fluoroalkylamine reagent of the formula (CVI)

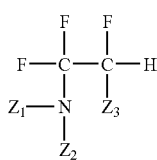

(CVI)

where:
$Z_1$ is $C_1$–$C_4$ alkyl;
$Z_2$ is $C_1$–$C_4$ alkyl and where $Z_1$ and $Z_2$ together with the attached nitrogen atom form a 5- or 6-member heterocycle selected from the group consisting of pyrrolidinyl, piperazinyl, piperidinyl and morpholinyl;
$Z_3$ is —F or —$CF_3$. It is preferred that $Z_1$ and $Z_2$ are $C_1$–$C_3$ alkyl. It is more preferred that $Z_1$ and $Z_2$ are $C_1$ alkyl or $C_2$ alkyl. It is preferred that the N-fluoroalkylamine (CVI) is N-(1,1,2,3,3,3-hexafluoropropyl)diethylamine, which is known as Ishikawa reagent, or 1,1,2,2-tetrafluoroethyl-N,N-dimethylamine.

The process of the invention is preferably performed by use of about 1 equivalent of 11α-hydroxy-17-lactone (CI) or 11α-hydroxy steroid (CIV) and from about 1 to about 1.5 equivalents of Ishikawa reagent; more preferred is about 1.2 equivalents of Ishikawa reagent. It is preferable to perform the process of the invention in a temperature range of from about 20 to about 82°; more preferably from about 40 to about 70°. The reaction usually takes from about 1 hr to about 24 to complete depending on reaction conditions especially temperature and concentration. For example at about 60° and 0.8 molar, the reaction takes about 3 hours.

The 11α-hydroxy-17-lactone (CI) or 11α-hydroxy steroid (CIV) can be added to the N-fluoroalkylamine reagent (CVI) or the N-fluoroalkylamine reagent (CVI) can be added to the 11α-hydroxy-17-lactone (CI) or 11α-hydroxy steroid (CIV); it is more practical to add the N-fluoroalkylamine reagent (CVI) to the 11α-hydroxy-17-lactone (CI) or 11α-hydroxy steroid (CIV).

It is preferred to perform the process of the present invention in a solvent that is dry (KF is <0.5%), such as acetonitrile.

The $\Delta^{9(11)}$-17-lactone of formula (CII), 17β-hydroxypregna-4,9(11)-dien-3-one-7α,21-dicarboxylic acid, γ-lactone, methyl ester, is known, see U.S. Pat. No. 4,559,332, Example 1(d) and International Publication WO98/25948, page 284. It is useful in the preparation of a pharmaceutical agent, 9α,11α-epoxy-17β-hydroxypregn-4-en-3-one-7α,21-dicarboxylic acid, γ-lactone, methyl ester, known as eplerenone (CIII).

The steroid C-ring functionality $\Delta^{9(11)}$- of compounds (CII) and (CV) is a very useful functionality to chemists skilled in the art of steroids. It can be readily transformed to the corresponding 9α,11α-epoxy functionality and the 9α-fluoro-11β-hydroxy functionality as well as 11-keto and others as is well known to those skilled in the art. These compounds are useful pharmaceutical agents. Hence, the process of the invention as it pertains to the transformation of the 11α-hydroxy steroid (CIV) to the corresponding $\Delta^{9(11)}$-steroid (CV) is a very useful process and is operable with a wide variety of 11α-hydroxy steroids (CIV) as is apparent to those skilled in the art. This includes progesterones, 17α-hydroxyprogesterones, corticoids as well as the usual common derivatives and analogs thereof such as esters, etc. Therefore, the process produces $\Delta^{9(11)}$-steroids (CV) which are useful intermediates in the preparation of pharmaceutically useful steroids. One skilled in the art with a given $\Delta^{9(11)}$-steroid (CV) would know how to transform it to a pharmaceutically useful product.

The present invention also includes a number of processes for transforming 11α-hydroxy compounds to the corresponding $\Delta^{9(11)}$-compounds by one or more processes described above. For example, described are processes for the transformation of (1) a 11α-hydroxy-7α-substituted steroid (II) to the corresponding $\Delta^{9(11)}$-7α-substituted steroid (II), (2) a process for transforming a 11α-hydroxy cis enedione (III-cis) or 11α-hydroxy trans enedione (III-trans) to the corresponding $\Delta^{9(11)}$-trans enedione (III-trans) and (3) for transforming a 11α-hydroxy-hydroxy compound (IV-OH) or a 11α-hydroxy-hydroperoxy compound (IV-OOH) or a 11α-hydroxy biscarbonyl compound (V) or mixture thereof to the corresponding $\Delta^{9(11)}$-carboxylic acid (VI).

Definitions and Conventions

The definitions and explanations below are for the terms as used throughout this entire document including both the specification and the claims.

I. Conventions for Formulas and Definitions of Variables

The chemical formulas representing various compounds or molecular fragments in the specification and claims may contain variable substituents in addition to expressly defined structural features. These variable substituents are identified by a letter or a letter followed by a numerical subscript, for example, "$Z_1$" or "$R_i$" where "i" is an integer. These variable substituents are either monovalent or bivalent, that is, they represent a group attached to the formula by one or two chemical bonds. For example, a group $Z_1$ would represent a bivalent variable if attached to the formula $CH_3$—$C(=Z_1)$H. Groups $R_i$ and $R_j$ would represent monovalent variable substituents if attached to the formula $CH_3$—$CH_2$—$C(R_i)$($R_j$)$H_2$. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parentheses. Thus, in the formula above, both $R_i$ and $R_j$ are bonded to the preceding carbon atom. Also, for any molecule with an established system of carbon atom numbering, such as steroids, these carbon atoms are designated as $C_i$, where "i" is the integer corresponding to the carbon atom number. For example, $C_6$ represents the 6 position or carbon atom number in the steroid nucleus as traditionally designated by those skilled in the art of steroid chemistry. Likewise the term "$R_6$" represents a variable substituent (either monovalent or bivalent) at the $C_6$ position.

Chemical formulas or portions thereof drawn in a linear fashion represent atoms in a linear chain. The symbol "–" in general represents a bond between two atoms in the chain. Thus $CH_3$—O—$CH_2$—$CH(R_i)$—$CH_3$ represents a 2-substituted-1-methoxypropane compound. In a similar fashion, the symbol "=" represents a double bond, e.g., $CH_2$=C($R_i$)—O—$CH_3$, and the symbol "≡" represents a triple bond, e.g., HC≡C—$CH(R_i)$—$CH_2$—$CH_3$. Carbonyl groups are represented in either one of two ways: —CO— or —C(=O)—, with the former being preferred for simplicity.

Chemical formulas of cyclic (ring) compounds or molecular fragments can be represented in a linear fashion. Thus, the compound 4-chloro-2-methylpyridine can be represented in linear fashion by N*=C(CH_3)—CH=CCl—CH=C*H with the convention that the atoms marked with an asterisk (*) are bonded to each other resulting in the formation of a ring. Likewise, the cyclic molecular fragment, 4-(ethyl)-1-piperazinyl can be represented by —N*—(CH_2)_2—N(C_2H_5)—CH_2—C*H_2.

A rigid cyclic (ring) structure for any compounds herein defines an orientation with respect to the plane of the ring for substituents attached to each carbon atom of the rigid cyclic compound. For saturated compounds which have two substituents attached to a carbon atom which is part of a cyclic system, —C($X_1$)($X_2$)— the two substituents may be in either an axial or equatorial position relative to the ring and may change between axial/equatorial. However, the position of the two substituents relative to the ring and each other remains fixed. While either substituent at times may lie in the plane of the ring (equatorial) rather than above or below the plane (axial), one substituent is always above the other. In chemical structural formulas depicting such compounds, a substituent ($X_1$) which is "below" another substituent ($X_2$) will be identified as being in the alpha (α) configuration and is identified by a broken, dashed or dotted line attachment to the carbon atom, i.e., by the symbol "- - -" or ". . .". The corresponding substituent attached "above" ($X_2$) the other ($X_1$) is identified as being in the beta (β) configuration and is indicated by an unbroken line attachment to the carbon atom.

When a variable substituent is bivalent, the valences may be taken together or separately or both in the definition of the variable. For example, a variable $R_i$ attached to a carbon atom as —C(=$R_i$)— might be bivalent and be defined as oxo or keto (thus forming a carbonyl group (—CO—) or as two separately attached monovalent variable substituents α-$R_{i-j}$ and β-$R_{i-k}$. When a bivalent variable, $R_i$, is defined to consist of two monovalent variable substituents, the convention used to define the bivalent variable is of the form "α-$R_{i-j}$:β-$R_{i-k}$" or some variant thereof. In such a case both α-$R_{i-j}$ and β-$R_{i-k}$ are attached to the carbon atom to give —C(α-$R_{i-j}$)(β-$R_{i-k}$)—. For example, when the bivalent variable $R_6$, —C(=$R_6$)— is defined to consist of two monovalent variable substituents, the two monovalent variable substituents are α-$R_{6-1}$:β-$R_{6-2}$, . . . α-$R_{6-9}$:β-$R_{6-10}$, etc, giving —C(α-$R_{6-1}$)(β-$R_{6-2}$)—, . . . —C(α-$R_{6-9}$)(β-$R_{6-10}$)—, etc. Likewise, for the bivalent variable $R_{11}$, —C(=$R_{11}$)—, two monovalent variable substituents are α-$R_{11-1}$:β-$R_{11-2}$. For a ring substituent for which separate α and β orientations do not exist (e.g. due to the presence of a carbon carbon double bond in the ring), and for a substituent bonded to a carbon atom which is not part of a ring the above convention is still used, but the α and β designations are omitted.

Just as a bivalent variable may be defined as two separate monovalent variable substituents, two separate monovalent variable substituents may be defined to be taken together to form a bivalent variable. For example, in the formula —$C_1(R_i)$H—$C_2(R_j)$H— ($C_1$ and $C_2$ define arbitrarily a first and second carbon atom, respectively) $R_i$ and $R_j$ may be defined to be taken together to form (1) a second bond between $C_1$ and $C_2$ or (2) a bivalent group such as oxa (—O—) and the formula thereby describes an epoxide. When $R_i$ and $R_j$ are taken together to form a more complex entity, such as the group —X—Y—, then the orientation of the entity is such that $C_1$ in the above formula is bonded to X and $C_2$ is bonded to Y. Thus, by convention the designation ". . . $R_i$ and $R_j$ are taken together to form —$CH_2$—$CH_2$—O—CO— . . . " means a lactone in which the carbonyl is bonded to $C_2$. However, when designated ". . . $R_j$ and $R_i$ are taken together to form —CO—O—$CH_2$—$CH_2$— the convention means a lactone in which the carbonyl is bonded to $C_1$.

The carbon atom content of variable substituents is indicated in one of two ways. The first method uses a prefix to the entire name of the variable such as "$C_1$–$C_4$", where both "1" and "4" are integers representing the minimum and maximum number of carbon atoms in the variable. The prefix is separated from the variable by a space. For example, "$C_1$–$C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus $C_2$–$C_4$ alkoxy-carbonyl describes a group $CH_3$—$(CH_2)_n$—O—CO— where n is zero, one or two. By the second method the carbon atom content of only each portion of the definition is indicated separately by enclosing the "$C_i$–$C_j$" designation in parentheses and placing it immediately (no intervening space) before the portion of the definition being defined. By this optional convention ($C_1$–$C_3$)alkoxycarbonyl has the same meaning as $C_2$–$C_4$ alkoxycarbonyl because the "$C_1$–$C_3$" refers only to the carbon atom content of the alkoxy group. Similarly while both $C_2$–$C_6$ alkoxyalkyl and ($C_1$–$C_3$)alkoxy($C_1$–$C_3$)alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

When the claims contain a fairly complex (cyclic) substituent, at the end of the phrase naming/designating that particular substituent will be a notation in (parentheses) which will correspond to the same name/designation in one of the CHARTS which will also set forth the chemical structural formula of that particular substituent.

II. Definitions

All temperatures-are in degrees Celsius.

TLC refers to thin-layer chromatography.

LC refers to liquid chromatography.

ESTDLC refers to external standard liquid chromatography.

THF refers to tetrahydrofuran.

DMAP refers to p-dimethylaminopyridine.

DDQ refers to 2,3-dichloro-5,6-dicyano-1,4-benzoquinone.

DBU refers to 1,8-diazabicyclo[5.4.0]undec-7-ene.

DBN refers to 1,5-diazabicyclo[4.3.0]non-5-ene.

DABCO refers 1,4-diazabicyclo[2.2.2]octane.

Chromatography (column and flash chromatography) refers to purification/separation of compounds expressed as (support, eluent). It is understood that the appropriate fractions are pooled and concentrated to give the desired compound(s).

Carboxylic acid (VI) refers to and includes the pharmaceutically acceptable salts thereof.

CMR refers to C-13 magnetic resonance spectroscopy, chemical shifts are reported in ppm ($\delta$) downfield from TMS.

NMR refers to nuclear (proton) magnetic resonance spectroscopy, chemical shifts are reported in ppm (d) downfield from TMS.

In the present invention the terms conversion/transformation or convert/transform are used interchangeable and mean the same thing, the reaction of one compound to form a different compound by the process described.

TMS refers to trimethylsilyl.

Oxone refers to $KHSO_5$.

-$\phi$ refers to phenyl ($C_6H_5$).

MS refers to mass spectrometry expressed as m/e, m/z or mass/charge unit. $[M+H]^+$ refers to the positive ion of a parent plus a hydrogen atom. EI refers to electron impact. CI refers to chemical ionization. FAB refers to fast atom bombardment.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When solvent pairs are used, the ratios of solvents used are volume/volume (v/v).

When the solubility of a solid in a solvent is used the ratio of the solid to the solvent is weight/volume (wt/v).

$\Delta^9$-Canrenone refers to 17$\beta$-hydroxypregna-4,6,9-trien-3-one-21-carboxylic acid, $\gamma$-lactone.

Eplerenone refers to 9$\alpha$,11$\alpha$-epoxy-17$\beta$-hydroxypregn-4-en-3-one-7$\alpha$,21-dicarboxylic acid, $\gamma$-lactone, methyl ester.

Neopentylglycol refers to HO—$CH_2$—$C(CH_3)_2$—$CH_2$—OH.

Iodosobenzene refers to $\phi$I=O.

Iodobenzenebistrifluoroacetate refers to $\phi$I(O—CO—$CF_3)_2$.

Iodobenzenediacetate refers to $\phi$I(O—CO—$CH_3)_2$.

Tritylfluoroborate is also known as triphenylcarbenium fluoroborate and refers to $\phi_3C^+BF_4^-$.

acac refers to acetylacetonate.

dppb refers to diphenylphosphino butane.

Tf refers to trifluoromethanesulfonate.

Dimethylsulfide refers to $CH_3SCH_3$.

Ishikawa reagent refers to N-(1,1,2,2,3,3,3)hexafluoropropyldiethylamine.

An "oxidatively cleaving agent" is a reagent that oxidizes the biscarbonyl compound (V) or hydroxy compound (IV-OH) to the carboxylic acid (VI).

A "hydroperoxy-deoxygenating agent" is a reagent that removes an oxygen atom from a hydroperoxide compound (IV-OOH) to give the corresponding hydroxy compound (IV-OH).

A "deoxygenating agent" is a reagent that removes one oxygen atom from a molecule. The "hydroperoxy-deoxygenating agent" is thus a particular type of deoxygenating agent.

A "carboxylic acid forming agent" is a reagent that induces a hydroperoxide compound (IV-OOH) to rearrange to a carboxylic acid (VI).

An "oxygen donating agent" is a reagent that provides an oxygen atom to a 7$\alpha$-substituted steroid (II) to transform it into a cis enedione (III-cis).

PXRD refers to powder X-ray diffraction.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Example 1

17β-Hydroxypregna-4,6,9(11)-trien-3-one-21-carboxylic acid, γ-lactone, Cyclic 3-(2',2'-dimethyl-1', 3'-propanediyl Ketal) (I-P)

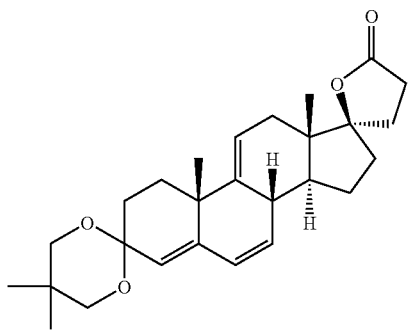

17β-hydroxypregna-4,6,9(11)-trien-3-one-21-carboxylic acid, γ-lactone 3-methyl enol ether (I, 3.00 g, 8.4629 mmoles) and lithium perchlorate (199.6 mg, 1.8761 mmoles, 0.22 equivalents) are slurried in acetonitrile (20 ml) and methylene chloride (10) are cooled to −15°, treated with 2,2-dimethyl-1,3-propyleneglycol (2.19 g, 21.027 mmoles, 2.48 equivalents), then treated drop wise over 73 min. with a solution of DDQ (2.29 g, 10.088 mmoles, 1.19 equivalents) in ethyl acetate. After stirring for 40 min, the reaction mixture is quenched with ammonium hydroxide (28%, 5 ml), diluted with ethyl acetate, concentrated, diluted with methylene chloride, and filtered. The filtrate is diluted with ethyl acetate, washed with aqueous sodium bicarbonate/sodium chloride followed by water, then filtered through magnesol, eluting with methylene chloride. The eluate is concentrated to give solids which are triturated with toluene, dried by a stream of nitrogen to give the title compound, CMR (CDCl$_3$) 14.44, 22.53, 22.78, 23.02, 24.89, 28.85, 29.22, 30.07, 30.18, 31.31, 32.92, 35.37, 38.56, 39.03, 44.35, 44.43, 70.54, 70.65, 95.17, 95.43, 116.80, 120.23, 127.82, 130.27, 141.83, 145.08 and 176.61δ; NMR (CDCl$_3$) 0.95, 0.97, 1.03, 1.18, 1.3–2.8, 3.5–3.7, 5.44, 5.71, 5.80 and 6.02δ.

Example 2

17β-Hydroxypregna-4,6,9(11)-trien-3-one-21-carboxylic acid, γ-lactone, Cyclic 3-ethanediyl Ketal (I-P)

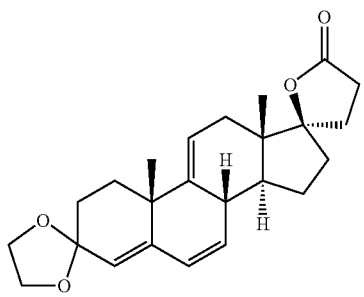

17β-hydroxypregna-4,6,9(11)-trien-3-one-21-carboxylic acid, γ-lactone 3-methyl enol ether (I, 300 mg, 0.8463 mmoles) in methylene chloride (5 ml) is cooled to −15° then treated with ethylene glycol (220 mg, 3.544 mmoles, 4.19 equivalents). To this mixture is added drop wise over 30 min. a solution of DDQ (230 mg, 1.0132 mmoles, 1.20 equivalents). After the addition is complete, the reaction is stirred at −15° for 5 min., at which time TLC analysis (ethyl acetate/cyclohexane, 66/34) shows conversion of the starting methyl enol ether (R$_f$=0.69) into the corresponding ethylene ketal (R$_f$=0.54) was nearly complete. The reaction is then quenched with concentrated ammonium hydroxide (0.5 ml), and filtered. The filtrate is then filtered through 1.0 g cartridge grade magnesol and concentrated to give the title compound, by comparison with an authentic sample, CMR (CDCl$_3$) 14.37, 22.95, 24.54, 29.15, 30.28, 31.23, 32.87, 35.30, 38.17, 38.45, 44.27, 44.37, 64.15, 64.70, 95.07, 105.94, 116.85, 122.39, 127.41, 130.24, 141.71, 145.76 and 176.51δ; NMR (CDCl$_3$) 0.97, 1.18, 1.3–2.9, 3.8–4.1, 5.29, 5.45, 5.70 and 5.99δ.

Example 3

17β-Hydroxy-7α-(5'-methyl-2'-furyl)-pregna-4,9(11)-dien-3-one-21-carboxylic acid, γ-lactone (II)

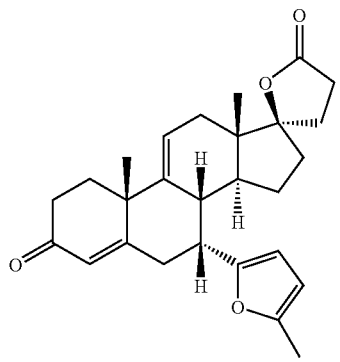

Δ$^9$-canrenone (I, 90.0 g, 0.2659 moles) is mixed with nitromethane (730–735 ml). Then 2-methylfuran (49.5 ml, 45.04 g, 0.5487 moles, 2.06 equivalents) is added. The resulting mixture is cooled to −20° then treated with absolute ethanol (15.8 ml, 12.55 g, 0.2723 moles, 1.02 equivalents) followed by boron trifluoride etherate, (d=1.120; 37.2 ml, 41.66 g, 0.2936 moles, 1.10 equivalents). The mixture is recooled to −18.40 and stirred for 17 hrs., at which time the reaction was complete by LC. The reaction mixture is quenched with ammonia (15% aqueous, 225 ml). The mixture is warmed to above 0°, water (200 ml) is added, the organic phase is separated, and the aqueous phase is extracted with methylene chloride (2×200 ml). The organic extracts are dried over magnesium sulfate (100 g) then filtered through magnesol (100 g cartridge grade), washing the cake with methylene chloride (5×200 ml). The eluate is then concentrated under reduced pressure to a foam, slurried with ethyl acetate (200 ml) and reconcentrated, then dissolved in ethyl acetate (950 ml) at 50° to 60°. The mixture is concentrated to about 500 ml volume, then diluted with cyclohexane (250 ml). The product begins to crystallize slowly. The slurry is reconcentrated to about 500 ml volume, cooled to 20–25°, further concentrated to about 400 ml volume, then cooled to 0°. After overnight at 0°, the slurry is filtered and the cake washed with cyclohexane followed by heptane and dried in a vacuum oven at 50° to give the title compound, TLC=0.37 (ethyl acetate/cyclohexane, 66/34), CMR (CDCl$_3$) 13.38, 14.12, 23.18, 26.83, 29.14, 31.26, 32.93, 33.93, 34.18, 35.39, 37.57, 38.52, 40.78, 41.90, 42.39, 44.08, 95.19, 105.89, 107.12, 119.73, 126.24, 149.99, 152.74, 167.45, 76.53 and 198.56; NMR (CDCl₃) 0.95, 1.43, 1.4–2.6, 2.16, 2.93, 3.30, 5.68 and 5.74δ.

The filtrate is concentrated to a foam which is dissolved in ethyl acetate (40 ml), concentrated to about 20 ml, seeded, diluted with cyclohexane (20 ml), concentrated to about 30 ml, cooled to 0° over the weekend, then filtered, washed with ethyl acetate/cyclohexane (1/2) and dried to give additional title compound.

Example 4

17β-Hydroxy-7α-(trans-1',4'-dioxopent-2'-en-1'yl) pregna-4,9(11)-dien-3-one-21-carboxylic acid, γ-lactone (III-trans)

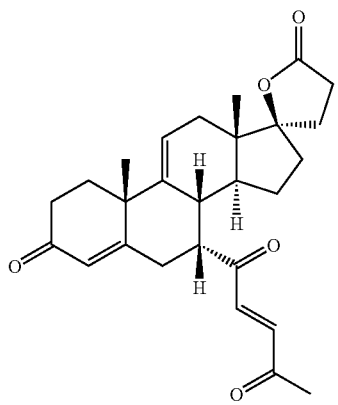

Step A: 17β-Hydroxy-7α-(cis-1',4'-dioxopent-2'-en-1'yl)pregna-4,9(11)-dien-3-one-21-carboxylic acid, γ-lactone (III-cis)

A mixture of 17β-hydroxy-7α-(5'-methyl-2'-furyl)-pregna-4,9(11)-dien-3-one-21-carboxylic acid, γ-lactone (II, EXAMPLE 3, 5.04 g, 11.9843 mmoles) and potassium acetate (1.7 g, 17.32 mmoles, 1.45 equivalents) in THF (40 ml) and water (12.5 ml) at 23.8° is treated with dibromantin (2.0 g, 6.995 mmoles, 0.58 equivalents) followed by isobutyl vinyl ether (500 W, 384 mg, 3.834 mmoles, 0.32 equivalents). The reaction mixture is stirred at 20–25° for 1 hr., at which time conversion of the starting material (II, R_f=0.50) into cis- and trans-enedione (R_f=0.11) is complete by TLC (ethyl acetate/cyclohexane, 66/34). The reaction mixture is diluted with water (200 ml) and extracted with methylene chloride (2×100 ml). The extracts are combined, washed with water (50 ml), dried over magnesium sulfate, filtered and concentrated to give the cis-enedione (III-cis).

Step B: 17β-Hydroxy-7α-(trans-1',4'-dioxopent-2'-en-1'yl)pregna-4,9(11)-dien-3-one-21-carboxylic acid, γ-lactone (III-trans)

The concentrate (Step A) is taken up in chloroform (100 ml) and the mixture is stirred at 20–25° for 20 hrs., at which time conversion of cis-enedione into trans-enedione is judged to be complete as measured by TLC and LC (cis/trans=1.1/98.9). The mixture is then concentrated and the concentrate is taken up in ethyl acetate (20 ml) at 20–25° and diluted with cyclohexane (80 ml), which induces crystallization. The slurry is cooled, filtered, and the cake washed with cyclohexane and dried under reduced pressure at 50° to give the title compound, CMR (CDCl₃) 13.98, 23.28, 27.08, 28.66, 29.01, 31.26, 32.77, 33.61, 34.01, 35.22, 35.28, 40.48, 40.51, 42.41, 44.43, 48.13, 94.77, 118.81, 126.03, 135.89, 137.04, 142.16, 165.21, 176.32, 197.81, 198.26 and 200.18; NMR(CDCl₃) 1.04, 1.30, 1.51, 1.5–3.6, 2.45, 5.71, 5.78 and 6.89δ; MS (electrospray) m/e=435 (p⁺−1) negative ion mode;

Example 5

17β-Hydroxypregna-4,9(11)-dien-3-one-7α,21-dicarboxylic acid, γ-lactone (VI)

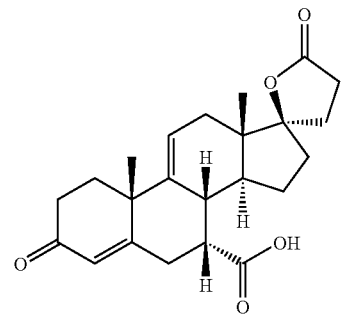

Step A: 17β-hydroxy-7α-(1'-oxo-2'-isopropoxy-2'-hydroxy-ethyl)pregna-4,9(11)-dien-3-one-21-carboxylic acid, γ-lactone (IV-OH); 17β-hydroxy-7α-(1'-oxo-2'-isopropoxy-2'-hydrohydroperoxyethyl) pregna-4,9(11)-dien-3-one-21-carboxylic acid, γ-lactone (IV-OOH) and 17β-hydroxy-7α-(2'-oxo-acetyl)-pregna-4,9(11)-dien-3-one-21-carboxylic acid, γ-lactone (V)

A mixture of 17β-hydroxy-7α-(trans-1',4'-dioxo-pent-2'-en-1'yl)pregna-4,9(11)-dien-3-one-21-carboxylic acid, γ-lactone (III-trans, EXAMPLE 4, 551.8 mg, 1.2640 mmoles) in isopropanol (11 ml) and methylene chloride (5 ml) is cooled to −55°. Ozone on oxygen is bubbled through this mixture until 0.4 area % (by LC) trans-enedione (III) remained. The mixture is purged of ozone by sparging with nitrogen for 7 minutes to give a mixture of the title compounds.

Step B: 17β-hydroxy-7α-(1'-oxo-2'-isopropoxy-2'-hydroxy-ethyl)pregna-4,9(11)-dien-3-one-21-carboxylic acid, γ-lactone (IV-OH), 17β-hydroxy-7α-(1',2'-dioxo-ethyl)pregna-4,9(11)-dien-3-one-21-carboxylic Acid, γ-lactone (V) and 17β-Hydroxy-7α-(2'-oxo-acetyl)-pregna-4,9(11)-dien-3-one-21-carboxylic acid, γ-lactone (V)

The mixture of Step A is then quenched with dimethylsulfide (340 μl, 288 mg, 4.630 mmoles, 3.66 equivalents), warmed to 20–25°, stirred at 20–25° for 50 min. to give a mixture of the title compounds.

Step C: 17β-Hydroxypregna-4,9(11)-dien-3-one-7α, 21-dicarboxylic acid, γ-lactone (VI)

The mixture of Step B is then treated with hydrogen peroxide (70% aqueous, 430 μl, 560 mg, containing 392 mg (11.52 mmoles, 9.12 equivalents) of hydrogen peroxide) and a solution of potassium bicarbonate (637.7 mg, 6.369 mmoles, 5.04 equivalents) in water (8 ml). The resulting two-phase mixture is diluted with enough methanol to produce a one-phase mixture (5 ml), which is then stirred at 20–25° for 16 hrs., then diluted to a volume of 500 ml with methanol for purpose of LC analysis. LC analysis indicates the title compound is obtained by comparison with a known compound.

A 20.0 ml portion of the 500 ml solution was withdrawn and further diluted with methanol to a volume of 50 ml. This solution (containing 17.3 mg [0.0450 mmoles] carboxylic acid by LC) is concentrated to a low volume, diluted with water, acidified with hydrochloric acid (1N), and extracted with methylene chloride (2×). The two extracts are each washed in sequence with water, then combined and concentrated. The concentrate is taken up in methanol/toluene (1/1; 2 ml) and treated with a mixture of trimethylsilyldiazomethane, $(CH_3)_3SiCHN_2$, in hexane (2.0 M, 0.25 ml, 0.50 mmoles, 11.1 equivalents). TLC analysis (ethyl acetate/cyclohexane; 66/34) indicates the title compound is obtained, $R_f$=0.23; LC analysis (210 nm detection) indicates the same retention time as a known standard and that the title compound is obtained.

Example 6

17β-Hydroxypregna-4,9(11)-dien-3-one-7α,21-dicarboxylic acid, γ-lactone, methyl ester (VIII)

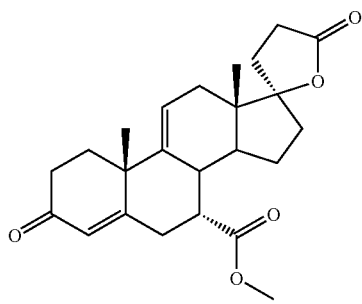

The remainder of the 500 ml mixture of Step C of EXAMPLE 5 (479 ml, containing 414.4 mg [1.0777 mmoles] 17β-hydroxypregna-4,9(11)-dien-3-one 7α,21-dicarboxylic acid, γ-lactone (VI, EXAMPLE 5C) is concentrated partially, diluted with water (20 ml), concentrated to a volume of about 20 ml, treated with hydrochloric acid (18 ml) and extracted with methylene chloride (25 ml, then 2×15 ml). The extracts are washed with water (30 ml), combined, and concentrated to a volume of 50.0 ml. Half of this mixture is concentrated to a low volume, diluted with ethyl acetate, and extracted with potassium bicarbonate (25% aqueous, 20 ml, then 10 ml). The extracts are combined, acidified to pH 3 with hydrochloric acid (1N) and extracted with methylene chloride (40 ml, then 2×15 ml). The extracts are then combined, washed with water, concentrated to a volume of <1 ml, and treated with a solution of sodium carbonate (349.6 mg, 3.298 mmoles, 6.12 equivalents based on carboxylic acid) in water (1.0 ml) followed by tetra-n-butylammonium bisulfate, $(n-butyl)_4NHSO_4$, (20.4 mg, 0.0601 mmoles, 0.11 equivalents) followed by dimethylsulfate (108 μl, 144.0 mg, 1.14 mmoles, 2.11 equivalents). The mixture is diluted with methylene chloride (0.1 ml), stirred at 20–25° for 11.5 hrs., treated with hydrochloric acid (1 N, 10 ml) and extracted with methylene chloride (10 ml, then 2×5 ml). The extracts are combined, washed with water, and concentrated to give the title compound, consistent with a known standard.

Example 7

17β-Hydroxy-7α-(cis-3'-acetoxyacryloyl)-pregna-4,9(11)-dien-3-one-21-carboxylic acid, γ-lactone
(X-cis)

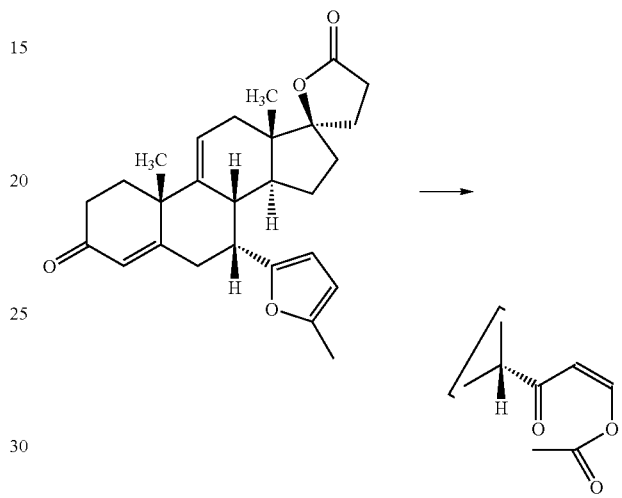

A stream of $O_3/O_2$ (ozone/oxygen) is passed through a cold (–78°) mixture of 17β-hydroxy-7α-(5'-methyl-2'-furyl)-pregna-4,9(11)-dien-3-one-21-carboxylic acid, γ-lactone (II, EXAMPLE 3, 3.0138 g, 7.1663 mmoles) in methylene chloride (40 ml) and methanol (10 ml) until the starting material had been consumed (LC, 25 min), then the mixture is purged with $O_2$ followed by nitrogen, quenched with trimethylphosphite (3.0 ml, 3.16 g, 25.435 mmoles, 3.55 equivalents), and warmed to 20–25°. After stirring for 1 hr., LC analysis indicates the title compound is obtained, CMR (100 MHz, $CDCl_3$) 198.49, 198.23, 176.43, 166.63, 166.10, 142.74, 142.44, 125.87, 118.12, 110.39, 94.99, 49.30, 44.47, 42.30, 40.59, 40, 35.46, 35.33, 34.11, 33.63, 32.83, 31.37, 29.11, 27.26, 23.31, 20.67 and 14.06 δ; NMR (400 MHz, $CDCl_3$) 0.94, 1.40, 1.5–2.9, 2.29, 5.38, 5.63 and 7.48 δ.

Example 8

17β-Hydroxy-7α-(trans-3'-acetoxyacryloyl)-pregna-4,9(11)-dien-3-one-21-carboxylic acid, γ-lactone
(X-trans)

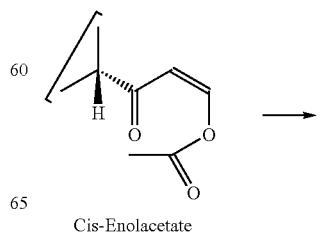

Cis-Enolacetate

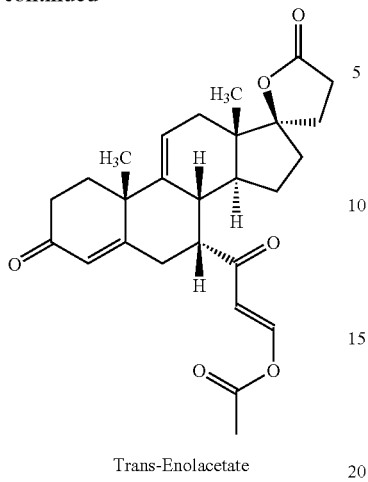

Trans-Enolacetate

After stirring the reaction mixture of EXAMPLE 7, 17β-hydroxy-7α-(cis-3'-acetoxyacryloyl)-pregna-4,9(11)-dien-3-one-21-carboxylic acid, γ-lactone (X-cis, EXAMPLE 7) for 1 hr., the reaction mixture is quenched with hydrochloric acid (5% aqueous, 25 ml) and stirred at 20–25° for 20 min., at which time isomerization to trans is complete. The organic phase is then separated, concentrated, and flash chromatographed (silica gel, 150 g; gradient elution, 40%→70% ethyl acetate/cyclohexane) to give the title compound. This material is then crystallized from ethyl acetate/heptane (70/30) to give the title compound in pure form, CMR (100 MHz, CDCl₃) 199.25, 198.39, 176.41, 166.79, 166.39, 149.00, 142.57, 125.67, 118.20, 113.11, 94.90, 47.75, 44.40, 42.40, 40.45, ~40, 35.63, 35.25, 34.01, 33.56, 32.73, 31.29, 29.04, 27.14, 23.32, 20.47 and 13.98 δ; NMR (400 MHz, CDCl₃) 1.14, 1.4–4.1, 1.61, 2.44, 5.75, 6.14 and 8.41 δ.

Example 9

17β-Hydroxy-7α-(2'-hydroperoxy-2'-methoxyacetyl) pregna-4,9(11)-dien-3-one-21-carboxylic acid, γ-lactone (IV-OOH)

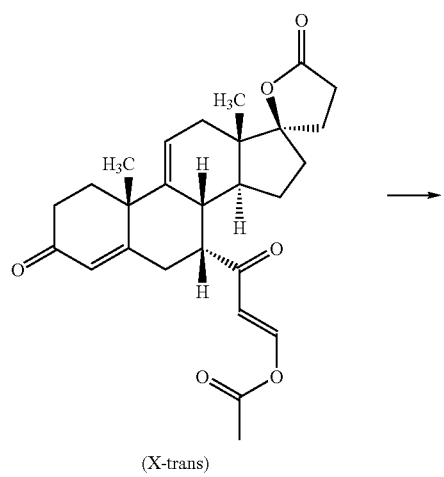

(X-trans)

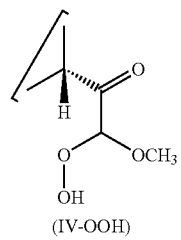

(IV-OOH)

A stream of ozone/oxygen is passed through a cooled (−78°) mixture of 17β-hydroxy-7α-(trans-3'-acetoxyacryloyl)-pregna-4,9(11)-dien-3-one-21-carboxylic acid, γ-lactone (X-trans, EXAMPLE 8, 311.0 mg, 0.6872 mmoles) in methylene/methanol (2/1, 6 ml) until a blue color persisted (3 min.). The excess ozone is purged with oxygen followed by nitrogen, then the reaction mixture is warmed to 20–25° and diluted with methylene chloride to 10 ml. A portion of this mixture (3.5 ml, from 0.2405 mmoles trans-enolacetate) is concentrated to dryness to give the title compound.

Example 10

5α,17β-Dihydroxypregn-9(11)-ene-3-one 7α,21-dicarboxylic acid, bis-γ-lactone (VII)

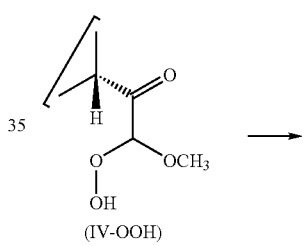

(IV-OOH)

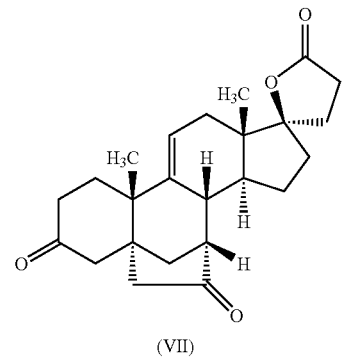

(VII)

17β-Hydroxy-7α-(2'-hydroperoxy-2'-methoxyacetyl)pregna-4,9(11)-dien-3-one-21carboxylic acid, γ-lactone (IV-OOH, EXAMPLE 9, 3.5 ml, from 0.2405 mmoles trans-enolacetate) is concentrated to dryness and the residue dissolved in trifluoroacetic acid (1.0 ml), stirred at 20–25° for 20 min., then diluted with ethyl acetate (1.0 ml), washed with aqueous sodium bicarbonate, diluted with methylene chloride (2.0 ml), washed with diluted aqueous hydrochloric acid and concentrated. The concentrate is taken up in methylene chloride (1.0 ml), stirred with aqueous hydrochloric acid (6N) for 30 min, then concentrated to give the title compound, CMR (100 MHz, CDCl₃) 206.39, 176.80, 175.59, 139.66, 124.11, 95.12, 91.11, 47.14, 43.99, 42.45, 41.66, 41.63, 41.15, 39.01, 37.04, 35.23, 33.08, 32.50, 31.42, 29.21, 23.16, 23.06 and 14.30 δ; NMR (400 MHz, CDCl$_3$) 0.94, 1.40, 1.5–2.6, 2.80, 5.70 δ; MS (CI, NH$_3$) m/e=402 (100%, P+NH$_4$).

Example 11

17β-Hydroxy-7α-(2'-oxo-acetyl)-pregna-4,9(11)-dien-3-one-21-carboxylic acid, γ-lactone (V)

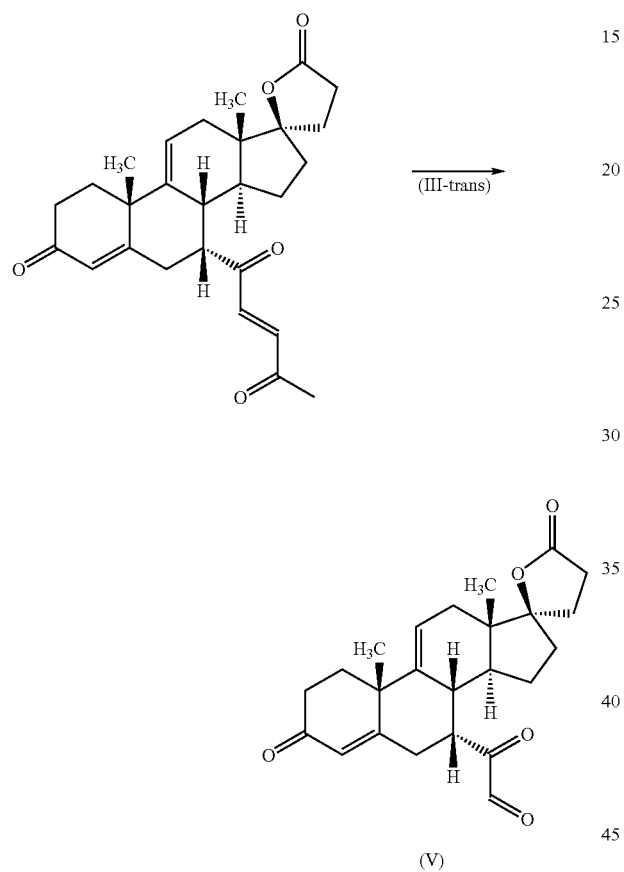

A stream of ozone/oxygen is passed through a cooled (−79°) mixture of 17β-hydroxy-7α-(trans-1',4'-dioxopent-2'-en-1'yl)pregna-4,9-dien-3-one-21-carboxylic acid, γ-lactone (III-trans, EXAMPLE 4B, 503.4 mg, 1.1531 mmoles) in methylene chloride/methanol (1/1, 4.0 ml) until TLC analysis (acetone/methylene chloride, 3/7) indicates that conversion of starting material (R$_f$=0.70) to a more polar product (R$_f$=0.45) is complete (10 min.). The reaction mixture is then quenched with dimethylsulfide (0.20 ml, 169 mg, 2.72 mmoles, 2.34 equivalents), stirred at 20–25° for 1 hr., and then concentrated. The concentrate is flash chromatographed (silica gel, 60 g; gradient elution, acetone/methylene chloride 5%→25%) to give the title compound, CMR (100 MHz, CD$_3$CN) 198.68, 197.54, 187.93, 176.09, 166.40, 142.33, 125.02, 118.56, 94.44, ~44, 42.49, 40.34, ~40, 39.87, 34.60, 33.83, 33.56, 33.32, 32.39, 30.53, 28.39, 26.16, 22.43 and 13.22 δ; NMR (400 MHz, CD$_3$CN) 0.87, 1.37, 1.2–2.9, 5.49, 5.63 and 8.93 δ; MS (CI, NH$_3$) m/e=397 (P+H, 100%).

Example 12

11α,17β-Dihydroxy-7α-5'-methyl-2'-furyl)-pregn-4-en-3-one-21-carboxylic acid, γ-lactone (II)

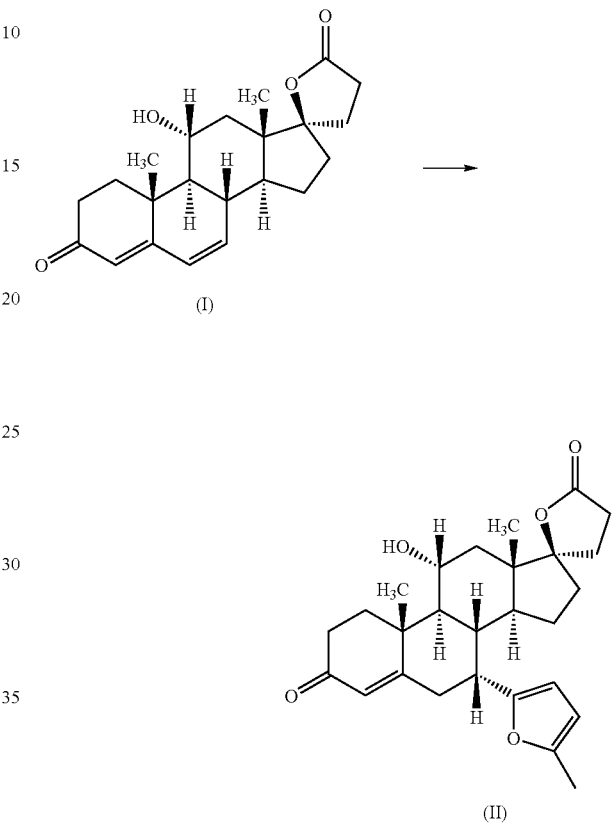

A mixture of 11α-hydroxycanrenone (I, 30.00 g, 84.1586 mmoles) in nitromethane (240 ml) and methylene chloride (60 ml) is cooled to −20° then treated with 2-methylfuran (15.6 ml, 14.20 g, 0.1729 moles, 2.05 equivalents) followed by ethanol (5.1 ml, 4.03 g, 87.454 mmoles, 1.04 equivalents) followed by boron trifluoride diethyl etherate (BF$_3$.OEt$_2$, 12.0 ml, 13.44 g, 94.695 mmoles, 1.13 equivalents). The reaction mixture is stirred at −17° for 20 hrs., then quenched with ammonia (15% aqueous, 60 ml), extracted with methylene chloride (120 ml), dried over sodium sulfate (40 g) and concentrated. The concentrate is dissolved in methylene chloride/ethyl acetate (1/1, 300 ml) concentrated to a volume of 75 ml, diluted with 150 ml cyclohexane, concentrated to a volume of 200 ml, and filtered to give the title compound, CMR (75 MHz, CDCl$_3$) 199.59, 176.67, 170.11, 152.92, 150.28, 126.20, 108.67, 105.90, 95.18, 68.55, 52.05, 45.84, 45.58, 43.08, 39.73, 38.62, 38.42, 37.47, 36.54, 35.26, 34.17, 30.91, 29.05, 22.62, 18.40, 15.58 and 13.44 δ; NMR (300 MHz, CDCl$_3$) 1.01, 1.1–3.2, 1.41, 2.20, 4.12, 5.73, 5.83 and 5.93 δ.

The filtrate is concentrated. The concentrate is taken up in ethyl acetate (30 ml warm), cooled to 10°, and filtered to give a second crop of crystal of the title compound.

Example 13

17β-Hydroxy-7α-(5'-methyl-2'-furyl)-pregna-4,9 (11)-dien-3-one-21-carboxylic acid, γ-lactone (II)

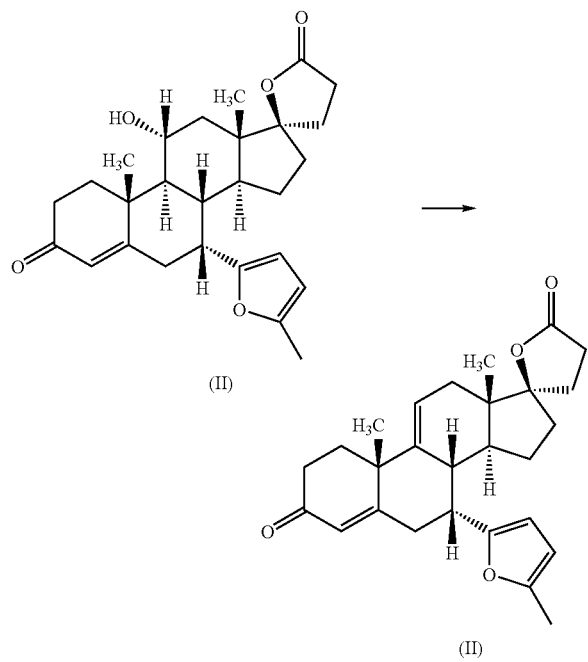

A mixture of 11α,17β-dihydroxy-7α-(5'-methyl-2'-furyl)-pregn-4-en-3-one-21-carboxylic acid, γ-lactone (II, EXAMPLE 12, 438.3 mg, 0.9994 mmoles) in THF (7.3 ml) is cooled to −50°, then treated all at once with solid phosphorous pentachloride, ($PCl_5$, 287.5 mg, 1.381 mmoles, 1.38 equivalents). After stirring for 42 min., analysis by LC indicates that conversion to the title compound is complete. After another 21 min., the mixture is quenched with water (22 ml) and warmed to 20–25°. After 20 min., the mixture is extracted with methylene chloride (2×15 ml), dried over magnesium sulfate, and concentrated to give the title compound, identified by LC retention time comparison with a sample from EXAMPLE 3.

Example 14

9α,11α-Epoxy-17β-hydroxy-7α-(5'-methyl-2'-furyl)-pregn-4-en-3-one-21-carboxylic acid, γ-lactone (II)

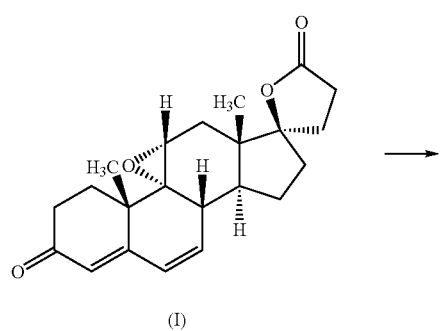

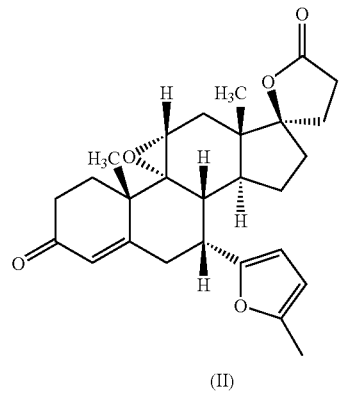

A mixture of 9α,11α-epoxycanrenone (I, *J. Med. Chem.*, 6, 732 (1963) and *Helv. Chim. Acta* 80, 566 (1997), 10.0135 g, 28.2508 mmoles) in nitromethane (80 ml) and methylene chloride (20 ml) is cooled to −20° then treated with 2-methylfuran (5.10 ml, 4.64 g, 56.529 mmoles, 2.00 equivalents) followed by ethanol (1.7 ml, 1.343 g, 29.151 mmoles, 1.03 equivalents) followed by boron trifluoride diethyl etherate ($BF_3.OEt_2$, 3.6 ml, 4.03 g, 28.408 mmoles, 1.01 equivalents). The reaction mixture is stirred at −20° for 24 hrs., at which time conversion to the product is complete as determined by LC, so the reaction is quenched with aqueous ammonia (15%, 10 ml), extracted with methylene chloride (2×100 ml), and concentrated to a residue which is flash chromatographed (560 g silica gel; gradient elution, 50%→90% ethyl acetate/cyclohexane). The material obtained by chromatography is triturated with cyclohexane (100 ml) at reflux for two hrs., then cooled to 0° and filtered to give the title compound, CMR (75 MHz, $CDCl_3$) 198.10, 176.26, 165.67, 153.19, 149.96, 127.56, 107.92, 106.14, 94.66, 65.45, 49.92, 43.82, 40.00, 39.18, 37.43, 37.37, 35.54, 35.00, 33.24, 31.00, 30.81, 28.91, 26.98, 22.26, 22.00, 16.61 and 13.47 δ; NMR (300 MHz, $CDCl_3$) 1.02, 1.3–3.0, 1.52, 2.20, 3.28, 5.85, 5.92 and 6.01 δ. The assigned structure is confirmed by X-ray crystallography.

Example 15

17β-Hydroxypregna-4,9(11)-dien-3-one-7α,21-dicarboxylic acid, γ-lactone (VI) via direct ozonization of 17β-hydroxy-7α-(cis-4'-oxo-pent-2'-enoyl)-3-oxo-pregna-4,9(11)-diene-21-carboxylic acid, γ-lactone (III-cis)

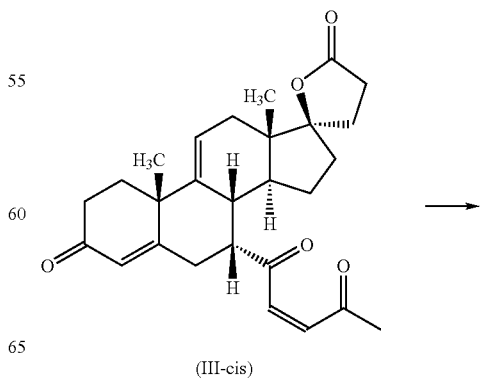

-continued

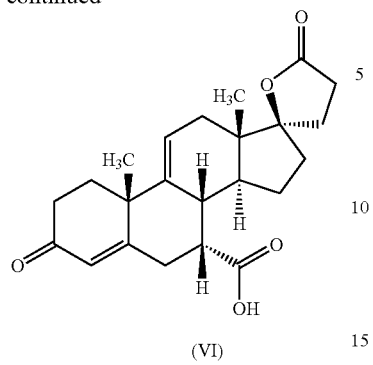

(VI)

A stream of ozone/oxygen is passed through a cooled (−55°) mixture of 17β-hydroxy-7α-(cis-4'-oxo-pent-2'-enoyl)-pregna-4,9(11)-dien-3-one-21-carboxylic acid, γ-lactone (III-cis, EXAMPLE 4 Step A, 52.4 mg, 0.1200 mmoles) in methylene chloride/isopropyl alcohol (1/1, 3.0 ml) containing water (50 mg, 2.77 mmoles, 23.1 equivalents) until disappearance of starting material is complete by LC (126 secs.). The reaction mixture is then quenched with dimethylsulfide (0.033 ml, 27.9 mg, 0.449 mmoles, 3.74 equivalents), stirred at 20–25° for 45 min., then diluted with methanol (5 ml), treated with aqueous hydrogen peroxide (70%, 50 μl, containing 45.6 mg [1.34 mmoles, 11.2 equivalents] of hydrogen peroxide, treated with a mixture of potassium bicarbonate (62.4 mg, 0.623 mmoles, 5.19 equivalents) in water (2 ml) and the resulting mixture stirred at 20–25°. After 15 hrs, analysis by LC indicates formation of the title compound.

Example 16

17β-Hydroxypregna-4,9(11)-dien-3-one-7α,21-dicarboxylic acid, γ-lactone (VI) via direct ozonization of 17β-hydroxy-7α-(trans-4'-oxo-pent-2'-enoyl)-pregna-4,9(11)-dien-3-one-21-carboxylic acid, γ-lactone (III-trans)

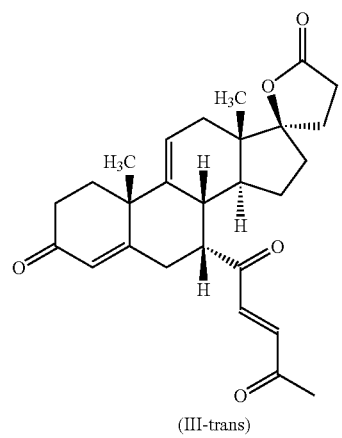

(III-trans)

→

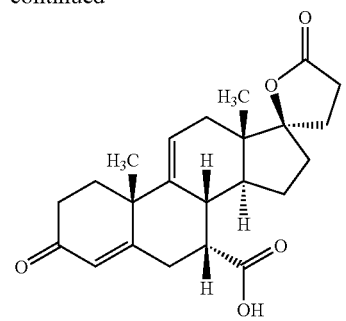

(VI)

A stream of ozone/oxygen is passed through a cooled (−55°) mixture of 17β-hydroxy-7α-(trans-4'-oxo-pent-2'-enoyl)-pregna-4,9(11)-dien-3-one-21-carboxylic acid, γ-lactone (III-trans, EXAMPLE 4 Step B, 103.5 mg, 0.2371 mmoles) in methylene chloride/isopropyl alcohol (1/1, 3 ml) containing water (50 mg, 2.77 mmoles, 11.7 equivalents) until disappearance of starting material is complete by LC (100 secs.). The reaction mixture is then quenched with dimethylsulfide ($CH_3SCH_3$, 65 μl, 55.0 mg, 0.885 mmoles, 3.73 equivalents), stirred at 20–25° for 45 min., then diluted to a volume of 10.0 ml with methanol. A 5.0 ml portion of this mixture is treated with aqueous hydrogen peroxide (70%, 50 μl, containing 45.6 mg [1.34 mmoles, 11.3 equivalents] of hydrogen peroxide, treated with a mixture of potassium bicarbonate (59 mg, 0.589 mmoles, 4.97 equivalents) in water (2.1 ml), and the resulting mixture stirred at 20–25°. After 15 hrs., analysis by LC (ESTD) indicates formation of the title compound, CMR (100 MHz, $CDCl_3$) 199.96, 177.42, 174.28, 169.06, 142.10, 124.86, 118.60, 95.60, 44.23, 43.48, 42.61, 40.38, 39.79, 35.59, 35.08, 33.73, 33.30, 32.57, 31.05, 28.98, 26.80, 22.92 and 13.68 δ; NMR (400 MHz, $CDCl_3$) 0.96, 1.42, 1.5–3.0, 4.28, 5.64 and 5.74 δ; MS (CI, $NH_3$; m/e)=402 (P+$NH_4^+$).

Example 17

5α,17β-Dihydroxypregn-9(11)-ene-3-one 7α, 21-dicarboxylic acid, bis-γ-lactone, 3-dimethyl Ketal (VII-Ketal)

5α,17β-Dihydroxypregn-9(11)-ene-3-one 7α,21-dicarboxylic acid, bis-γ-lactone (VII, EXAMPLE 10) is treated with at least one equivalent of trimethyl ortho formate in the presence of a catalytic amount of p-toluenesulfonic acid by the procedure of International Publication WO98/25948, to give the title compound.

Example 18

17β-hydroxypregna-4,9(11)-dien-3-one-7α,21-dicarboxylic acid, γ-lactone, methyl ester (VIII)

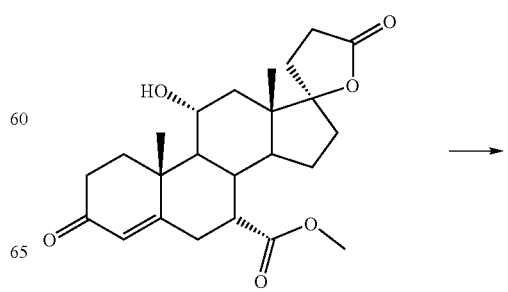

→

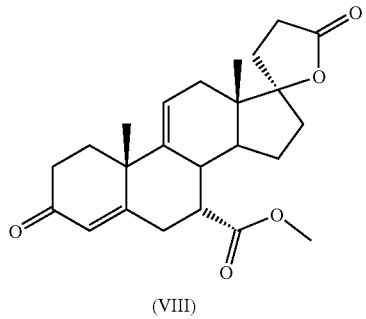

(VIII)

11α,17β-dihydroxypregn-4-en-3-one-7α,21-dicarboxylic acid, γ-lactone, methyl ester (VIII, Drugs of the Future, 24(5), 488–501 (1999), compound (VI)), 5.00 g, 12.0 mmol) is mixed with acetonitrile (15 ml). N-(1,1,2,3,3,3)hexafluoropropyl)-diethylamine (V, 2.55 ml, 14.4 mmol) is added to this the steroid mixture and heated to 600 for 2.5 hours. The resulting mixture is cooled to 20–25° and the reaction is quenched with methanol (100 μL). A saturated aqueous solution of potassium bicarbonate (15 ml) is added. The acetonitrile is then removed under reduced pressure. The resulting mixture is extracted with methylene chloride (3×10 ml). The combined organic phases are washed with a aqueous solution of sodium chloride (10%, 20 ml). The solvent is dried with magnesium sulfate. The solvent is exchanged from methylene chloride to methyl t-butyl ether (MTBE). The mixture is concentrated to a final volume of 25 ml. The resulting slurry is stirred overnight and the final product, the title compound, is collected by filtration.

Example 19

17β-hydroxypregna-4,9(11)-dien-3-one-7α,21-dicarboxylic acid, γ-lactone, methyl ester (VIII)

11α,17β-dihydroxypregn-4-en-3-one-7α,21-dicarboxylic acid, γ-lactone, methyl ester (VIII, 5.00 g, 12.0 mmol) is placed in a flask with acetonitrile (15 ml). To this mixture N-(1,1,2,3,3,3)hexafluoropropyl)-diethylamine (2.55 ml, 14.4 mmol) is added and heated to 60° for 2 hrs. The mixture is cooled to 20–25° and the reaction is quenched with aqueous potassium bicarbonate (20% solution, 18 ml). The acetonitrile is removed under reduced pressure, the aqueous layer is extracted with methylene chloride (3×5 ml). The combined organic phases are washed with sodium chloride solution (10%, 10 ml). The solvent is exchanged from methylene chloride to methyl isobutyl ketone/heptane to crystallize the title compound, mp=198.6–199.5°; MS (m/z) calculated for $C_{24}H_{30}O_5$=398.5 (M+), found 398.9(M+); NMR (CDCl$_3$) 5.69, 5.64, 3.62, 2.97, 2.84–1.47, 1.38 and 0.93 δ; CMR (CDCl$_3$) 98.5, 176.4, 172.5, 166.5, 142.3, 125.6, 118.9, 95.0, 51.3, 43.0, 40.3, 35.6, 35.2, 34.1, 33.7, 32.8, 31.2, 29.0, 27.1, 23.2 and 14.0 δ.

Example 20

17β-hydroxypregna-4,9(11)-dien-3-one-7α,21-dicarboxylic acid, γ-lactone, methyl ester (VIII)

11α,17β-dihydroxypregn-4-en-3-one-7α,21-dicarboxylic acid, γ-lactone, methyl ester (VIII, 80.00 g, 192.1 mmol) is placed in a flask with acetonitrile (80 ml). To this mixture N-(1,1,2,3,3,3)hexafluoropropyl)-diethylamine (40.8 ml, 224.8 mmol) is added and heated slowly to 45 to 50°, then held for 1–2 hours. The mixture is cooled to 20–25° and the reaction is quenched with aqueous potassium bicarbonate (72 g in 288 ml). Methylene chloride (240 ml) is added and after mixing the layers are separated. The aqueous phase is extracted with methylene chloride (100 ml). The combined organic phases are washed with water (240 ml). The solvent is exchanged from methylene chloride to methyl tert-butyl ether, and branched octane is added drop wise to crystallize the product which is the title compound.

Example 21

17β-Hydroxy-7α-(5'-methyl-2'-furyl)-pregna-4,9-dien-3-one-21-carboxylic acid, γ-lactone (II)

Following the general procedure of EXAMPLE 3, using the same reactants and making non-critical variations, the title compound is obtained, CMR (100 MHz, CDCl$_3$) 198.56, 176.53, 167.45, 152.74, 149.99, 142.84, 126.24, 119.73, 107.12, 105.89, 95.19, 44.08, 42.39, 41.90, 40.78, 38.52, 37.57, 35.39, 34.18, 33.93, 32.93, 31.26, 29.14, 26.83, 23.18, 14.12 and 13.38 δ; NMR (400 MHz, CDCl$_3$) 0.95, 1.43, 1.4–2.6, 2.16, 2.93 and 5.7 δ.

Example 22

17β-Hydroxy-7α-(cis-1',4'-dioxopent-2'-en-1'yl) pregna-4,9-dien-3-one-21-carboxylic acid, γ-lactone (III-cis)

Following the general procedure of EXAMPLE 4, Step A, using the same reactants and making non-critical variations, the title compound is obtained, CMR (100 MHz, CDCl$_3$) 202.28, ~200, 199.05, 177.19, 166.56, 142.34, 138.49, 134.39, 126.37, 119.90, 95.57, 49.63, 44.90, 42.39, 41.08, 41.04, 35.82, 35.75, 34.49, 34.07, 33.25, 31.71, 30.12, 29.64, 27.49, 23.76 and 14.34 δ; NMR (400 MHz, CDCl$_3$) 0.93, 1.40, 1.4–2.9, 2.24, 5.66, 5.72, 6.15 and 6.28 δ.

Example 23

17β-Hydroxy-7α-(2'-hydroperoxy-2'-methoxyacetyl) pregna-4,9(11)-dien-3-one-21-carboxylic acid, γ-lactone (IV-OOH)

Following the general procedure of EXAMPLE 9, using the same reactants and making non-critical variations, the title compound is obtained, CMR (100 MHz, CDCl$_3$) 203.54, 199.91, 177.51, 168.98, 142.42, 125.05, 117.89, 105.90, 95.58, 55.82, 44.21, 44.21, 42.17, 41.21, 40.37, 35.33, 34.84, 33.62, 33.16, 32.38, 30.79, 28.84, 26.72, 23.02 and 13.55δ; NMR (400 MHz, CDCl$_3$) 0.94, 1.42, 1.4–2.8, 3.57, 4.34, 4.75 and 5.63 δ.

Example 24

17β-Hydroxy-7α-(5'-methyl-2'-furyl)-pregna-4,9 (11)-dien-3-one-21-carboxylic acid, γ-lactone (II)

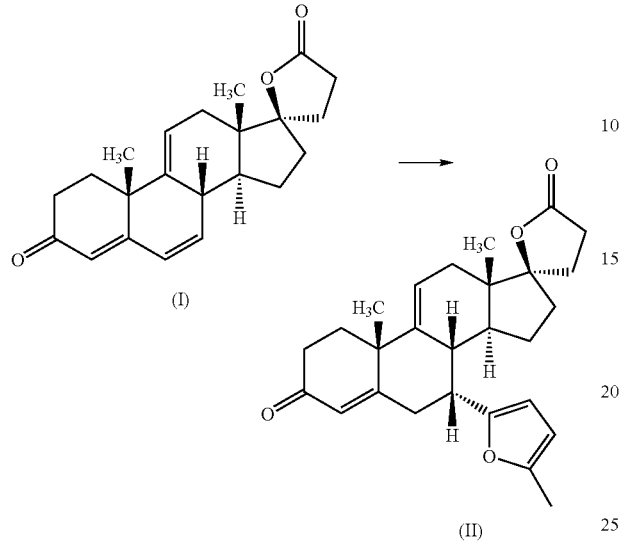

A mixture of Δ⁹-canrenone (I, 105 g, 0.31024 moles) in acetonitrile (450 ml) is treated with ethanol (21.0 g, 0.4558 moles, 1.47 equivalents), isopropanol (1.5 ml, 1.177 g, 19.592 mmoles, 0.063 equivalents), and 2-methylfuran (48.5 g, 0.5907 moles, 1.90 equivalents), then cooled to −18° and treated with boron trifluoride diethyl etherate (63.0 g, 0.4439 moles, 1.43 equivalents) over 4 hours. After stirring at −18° for 24 hrs., the mixture is quenched with triethylamine (38.0 g, 0.3755 moles, 1.21 equivalents) and concentrated to a thick slurry, which is diluted with water (350 ml), extracted with methylene chloride (400 ml), washed with water (350 ml), then concentrated, n-propyl acetate added, and further concentrated to give a slurry, which is cooled to 0°, filtered, and the cake washed with n-propyl acetate/methyl-t-butyl ether (1/1) followed by methyl-t-butyl ether to give the title compound, identified by LC retention time comparison with a sample from EXAMPLE 3.

Example 25

5α,17β-Dihydroxypregn-9(11)-ene-3-one, 7α,21-dicarboxylic acid, bis-γ-lactone (VII)

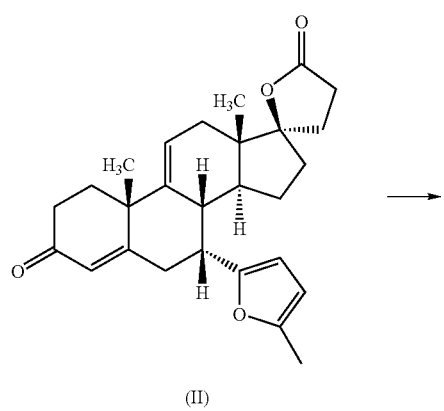

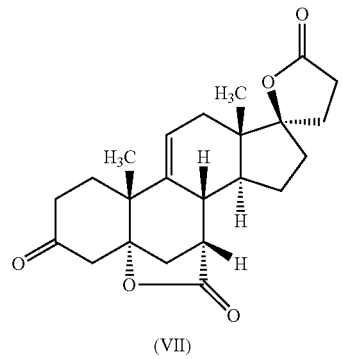

A mixture of 17β-hydroxy-7α-(5'-methyl-2'-furyl)-pregna-4,9(11)-dien-3-one-21-carboxylic acid, γ-lactone (II, EXAMPLE 24, 100 g, 0.23778 moles) and potassium acetate (50.0 g, 0.5094 moles, 2.14 equivalents) in acetone (500 ml) and water (150 ml) is cooled to −10° and treated with a slurry of dibromantin (34.0 g, 0.1189 moles, 0.50 molar equivalents) in water (100 ml) until a rise in the redox potential occurred. At this point, LC analysis indicated complete conversion into enedione (III-cis). The reaction mixture containing the enedione (III-cis) is then quenched with isobutyl vinyl ether (1.0 ml, 0.768 g, 7.668 mmoles, 0.032 equivalents), concentrated to a thick slurry, diluted with methylene chloride (200 ml), and treated with 20° concentrated hydrochloric acid (50.0 ml, 0.50 moles, 2.10 equivalents). The mixture is stirred at 20–25° for 2 hrs., at which time LC analysis indicated complete conversion to enedione (III-trans). The organic phase containing the enedione (III-trans) is separated, diluted with methylene chloride (80 ml) and methanol (300 ml), and cooled to −48°. A stream of $O_3/O_2$ is bubbled through this mixture until LC analysis indicated complete disappearance of the enedione (III-trans), then the mixture is quenched with dimethylsulfide (30.0 ml, 25.38 g, 0.4085 moles, 1.72 equivalents), stirred at −20° for 16 hrs., concentrated to a volume of about 300 ml, diluted with methanol (350 ml), concentrated to a volume of about 300 ml, diluted with isopropanol (40 ml) and methanol (80 ml), then treated with a warm (55–600) solution of potassium bicarbonate (120 g, 1.1986 moles, 5.04 equivalents) in water (240 ml). This slurry is cooled to 5–10°, then hydrogen peroxide (50%, 66.0 g, containing 33.0 g (0.9703 moles, 4.08 equivalents) hydrogen peroxide) is added over 3 hrs. The mixture is stirred for four hrs. and quenched with dimethylsulfide (40 ml, 33.84 g, 0.5447 moles, 2.29 equivalents). After stirring at 20–25° for 23 hrs., the mixture is diluted with methylene chloride (100 ml) and water (80 ml), and acidified to pH=3.0 with concentrated hydrochloric acid. The two-phase mixture is heated to 36°, then the phases are separated and the aqueous phase extracted with methylene chloride (100 ml). The organic phases are combined, washed with water (75 ml), and the aqueous phase is back-extracted with methylene chloride (25 ml). The organic phases are combined, concentrated to a volume of 150 ml, then treated with benzenesulfonic acid (1.0 g of 90% pure material, containing 0.90 g (5.690 mmoles, 0.0239 equivalents) benzenesulfonic acid) and acetone (50 ml). The mixture is then concentrated atmospherically to a volume of 160 ml, then diluted with acetone (250 ml), concentrated to a volume of 200 ml, cooled to 12°, and filtered. The filter cake is washed with cold acetone (2×25 ml) and dried by nitrogen stream to give the title compound, CMR (100 MHz, CDCl$_3$) 206.08, 176.47, 175.41, 139.63, 124.00, 94.89, 90.97, 47.08, 43.90, 42.36, 41.58, 41.07, 38.93, 36.97, 35.16, 33.01, 32.42, 32.42, 31.35, 29.10, 23.08, 22.98 and 14.23 δ; NMR (400 MHz, CDCl$_3$) 0.94, 1.40, 1.4–2.8 and 5.70; MS (CI, NH$_3$) m/e=385 (P+H, 100%).

Example 26

17β-Hydroxy-7α-carbomethoxypregna-4,9(11)-dien-3-one-21-carboxylic acid, γ-lactone (VIII)

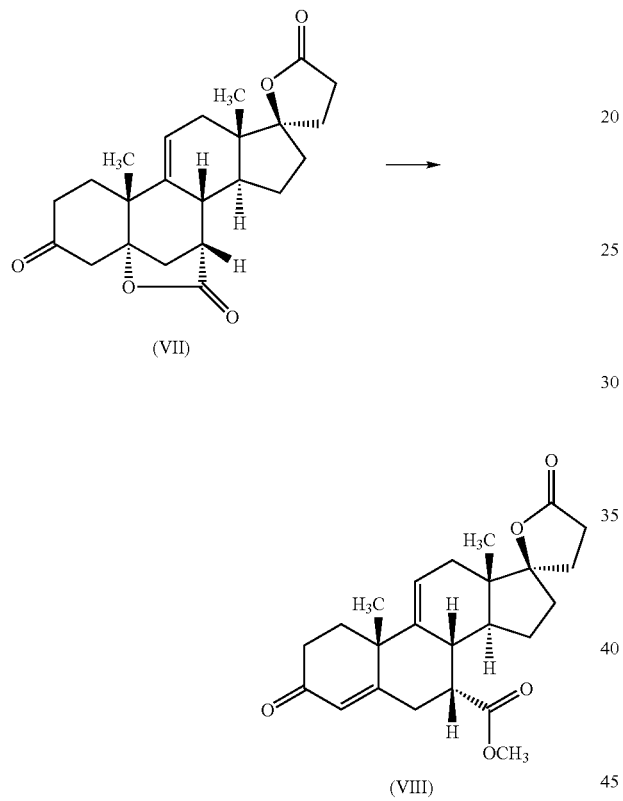

A mixture of 5α,17β-dihydroxypregn-9(11)-ene-3-one, 7α,21-dicarboxylic acid, bis-γ-lactone (VII, EXAMPLE 25, 50.0 g, 0.13005 moles) and potassium bicarbonate (16.92 g, 0.1690 moles, 1.30 equivalents) in acetone (200 ml) and water (100 ml) is stirred at 45° for 2 hrs., at which time conversion of the 5,7-lactone (VIE) into the carboxylic acid (VI) is complete by LC. The resulting mixture is then treated with dimethylsulfate (22.92 g, 0.1817 moles, 1.40 equivalents), stirred at 45° for 3 hrs., then treated with a solution of potassium bicarbonate (1.3 g, 0.0130 moles, 0.100 equivalents) in water (10 ml) followed by neat triethylamine (1.81 ml, 1.314 g, 0.0130 moles, 0.100 equivalents). The mixture is stirred at 45° for 1 hr., quenched with concentrated hydrochloric acid (1.92 ml, 2.304 g, containing 0.852 g (0.0234 moles, 0.180 equivalents) hydrochloric acid), cooled to 00, concentrated under reduced pressure to a volume of 150 ml (pot temperature 13°), then filtered and the filter cake is washed with water (2×25 ml) and dried to give the title compound, by comparison with an authentic sample by LC.

Example 27

17β-Hydroxy-7α-(5'-t-butyl-2'-furyl)-pregna-4,9 (11)-dien-3-one-21-carboxylic acid, γ-lactone (II)

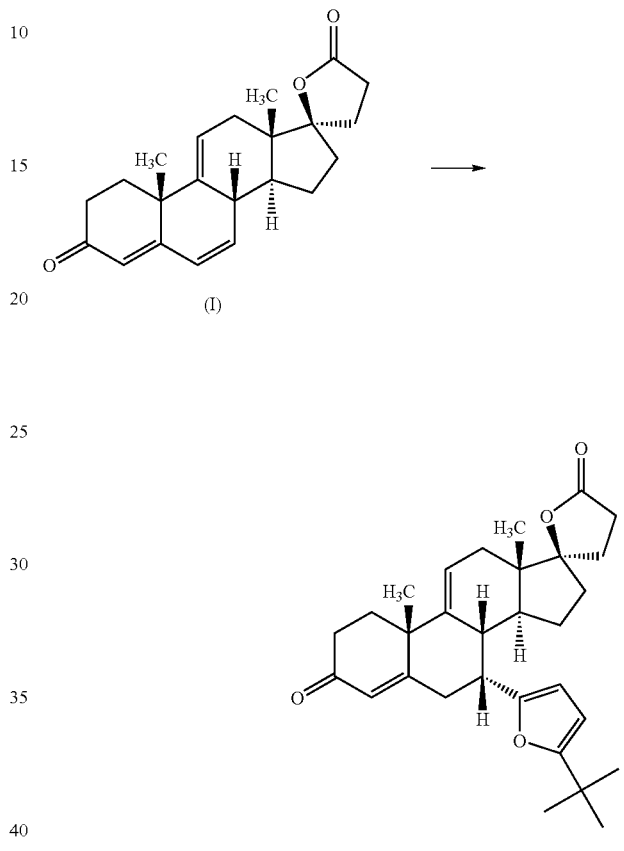

A mixture of Δ$^9$-canrenone (I, 3.0002 g, 8.8645 mmoles) and 2-t-butylfuran (2.53 ml, 2.204 g, 17.745 mmoles, 2.00 equivalents) in nitromethane (12.0 ml) is treated with ethanol (0.52 ml, 413 mg, 8.96 mmoles, 1.01 equivalents), cooled to −20°, and treated with boron trifluoride diethyl etherate (1.24 ml, 1.389 g, 9.785 mmoles, 1.10 equivalents). The resulting mixture is stirred at −20° for 24 hrs., then at −5° for 12 hrs., then at 0° for 4 hrs., at which time the reaction appeared about 90% complete by TLC. The reaction is quenched with ammonium hydroxide (7%, 30 ml) extracted with methylene chloride (3×50 ml), dried over magnesium sulfate, and concentrated. The concentrate is flash chromatographed on (silica gel, 150 g; gradient elution, 10%→50% ethyl acetate/cyclohexane). The fractions containing pure product are combined and concentrated to give the title compound, CMR (100 MHz, CDCl$_3$) 198.56, 176.53, 167.87, 162.48, 153.02, 142.91, 125.84, 119.42, 106.70, 101.88, 95.21, 44.05, 42.87, 41.90, 40.84, 38.17, 37.80, 35.52, 34.20, 34.02, 32.97, 32.40, 31.33, 29.18, 28.71, 26.79, 23.17 and 14.14 δ; NMR (400 MHz, CDCl$_3$) 0.95, 1.16, 1.45, 1.5–2.6, 2.94, 3.30, 5.64, 5.72 and 5.76 δ.

Example 28

11α,17β-Dihydroxy-7α-(5'-t-butyl-2'-furyl)-pregn-4-en-3-one-21-carboxylic acid, γ-lactone (II)

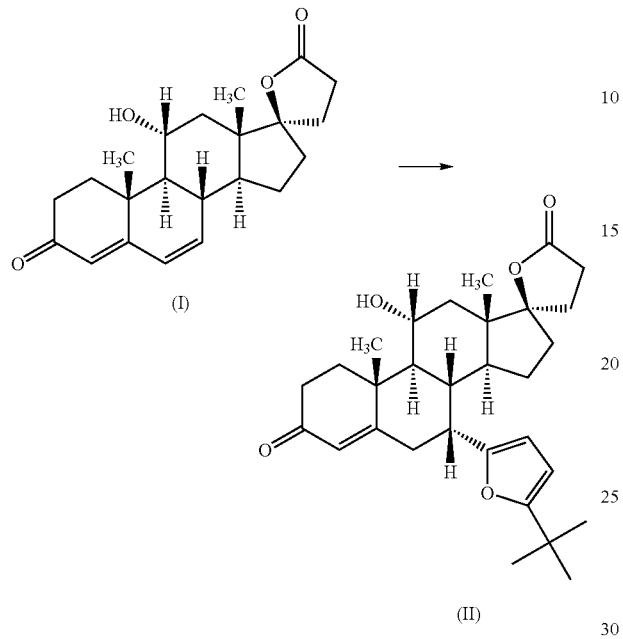

A mixture of 11α-hydroxycanrenone (I, 2.03 g, 5.6947 mmoles) and 2-t-butylfuran (1.70 ml, 1.481 g, 11.924 mmoles, 2.09 equivalents) in nitromethane (16 ml) is cooled to −20°, treated with ethanol (0.35 ml, 0.276 g, 5.99 mmoles, 1.05 equivalents) and boron trifluoride diethyl etherate (0.83 ml, 0.930 g, 6.550 mmoles, 1.15 equivalents), and stirred at −20° for 21 hrs., at which time LC analysis indicates that the reaction is complete. The reaction mixture is then quenched with ammonium hydroxide (15%, 5.5 ml), diluted with water, extracted with methylene chloride (2×25 ml), dried over magnesium sulfate, filtered through 5.0 g magnesol, and concentrated to a foam, which is flash chromatographed (silica gel, 200 g; gradient elution 20%→70% ethyl acetate/cyclohexane). The fractions containing the product are combined and concentrated to give the title compound, UV $\lambda_{max}$=238 mμ.

Example 29

11α,17β-Dihydroxy-7α-(4'-bromo-2'-furyl)-pregn-4-en-3-one-21-carboxylic acid, γ-lactone (II)

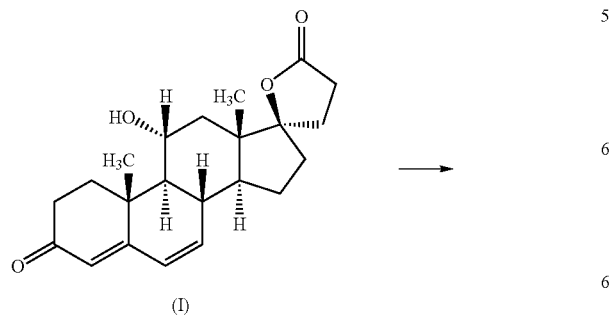

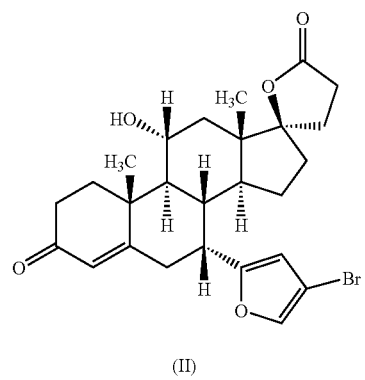

A mixture of 11α-hydroxycanrenone (I, 2.0 g, 5.6425 mmoles), ethylene glycol (0.84 ml, 0.935 g, 15.06 mmoles, 2.67 equivalents), and 3-bromofuran (3.0 ml, 4.905 g, 33.372 mmoles, 5.91 equivalents) in nitromethane (32 ml) at 20–25° is treated with boron trifluoride diethyl etherate (1.4 ml, 1.568 g, 11.048 mmoles, 1.96 equivalents) and stirred at 20–25° for 20 hrs., at which time the reaction is >80% complete by LC. The reaction is then quenched with water, extracted with ethyl acetate, and concentrated to give a foam, which is dissolved in methylene chloride (10 ml) and flash chromatographed (silica gel, 150 g; gradient elution 0→6% isopropanol/methylene chloride). The product-containing fractions are then combined and rechromatographed (silica gel, 100 g silica gel; gradient elution 0→5% isopropanol/methylene chloride). The product-containing fractions are combined and crystallized from ethyl acetate/cyclohexane (1/2) to give the title compound, CMR (100 MHz, CDCl$_3$) 199.77, 176.54, 168.67, 152.83, 142.43, 126.05, 113.41, 98.03, 95.02, 69.19, 53.51, 46.26, 46.19, 43.40, 39.57, 38.72, 38.05, 37.48, 35.39, 34.77, 34.24, 31.09, 29.11, 22.68, 18.46 and 15.84 δ; NMR (400 MHz, CDCl$_3$) 0.9–2.9, 1.03, 1.42, 3.35, 4.11, 6.36 and 7.26 δ; MS (CI, NH$_3$) m/e=503, 505 (100%, P+H).

Example 30

11α,17β-Dihydroxy-7α-(4'-methyl-2'-furyl)-pregn-4-en-3-one-21-carboxylic acid, γ-lactone (II)

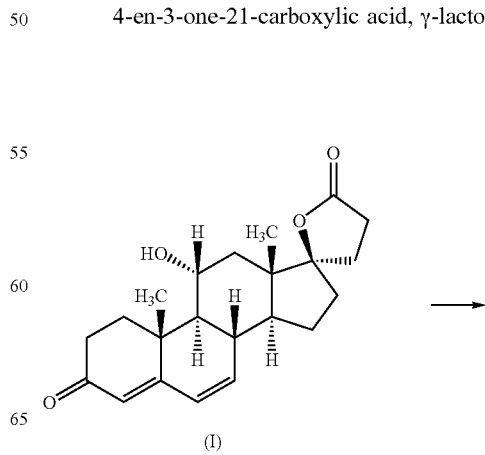

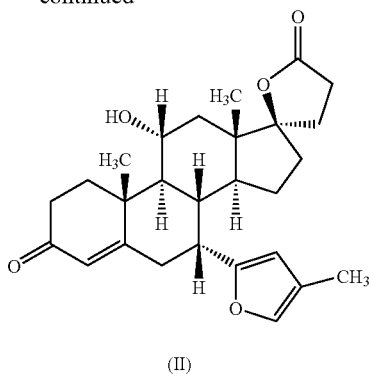

(II)

A mixture of 11α-hydroxycanrenone (1,816 mg, 2.2891 mmoles) and 3-methylfuran (4.0 ml of 1.218 M solution in nitromethane, 4.87 mmoles, 2.13 equivalents) in nitromethane (4.0 ml) is cooled to −20° and treated with ethylene glycol (0.168 ml, 187 mg, 3.01 mmoles, 1.32 equivalents) followed by boron trifluoride diethyl etherate (0.284 ml, 318 mg, 2.241 mmoles, 0.98 equivalents). The resulting mixture is stirred at −20° for 20 hrs., at which time the reaction is 86% complete by LC. The reaction mixture is quenched with aqueous ammonium hydroxide (15%, 4 ml) diluted with water (10 ml), extracted with methylene chloride (2×20 ml), dried over magnesium sulfate, and concentrated. The concentrate is flash chromatographed (silica gel, 60 g; gradient elution 50%→100% ethyl acetate/cyclohexane). The product-containing fractions are combined and concentrated. The concentrate is crystallized from cyclohexane/ethyl acetate (4/1) to give the title compound, CMR (100 MHz, CDCl$_3$) 199.91, 176.62, 170.02, 150.94, 140.81, 125.57, 115.27, 112.29, 95.07, 69.16, 53.50, 46.13, 45.99, 43.24, 39.52, 39.46, 38.14, 37.35, 35.32, 34.18, 31.05, 29.07, 22.28, 18.46, 15.79 and 10.21 δ; NMR (400 MHz, CDCl$_3$) 1.04, 1.0–2.9, 1.42, 1.96, 3.14, 4.12, 5.34, 6.12 and 7.15 δ; MS (C$_1$, NH$_3$) m/e=439 (100%, P+H).

Example 31

17β-Hydroxy-7α-(5'-methyl-2'-furyl)-pregna-4,9 (11)-dien-3-one-21-carboxylic acid, γ-lactone (II)

Ishikawa reagent (2.4 mK, 13.7 mmol) is added to a mixture of 11α,17β-dihydroxy-7α-(5'-methyl-2'-furyl)-pregn-4-en-3-one-21-carboxylic acid, γ-lactone (II, EXAMPLE 12, 5 g, 11.4 mmol) in acetonitrile (25 mL). The mixture is heated to 60° and is determined complete in 1 hr by HPLC. The resulting mixture is cooled to 22° and quenched with saturated aqueous sodium bicarbonate (15 mL). The organic solvent is removed under reduced pressure and replaced with methylene chloride (50 mL). The organic phase is separated, washed with water (30 mL) and concentrated to a volume of 20 mL. Water (30 mL) is added and the mixture is concentrated to a volume of 20 mL. This water distillation is repeated twice to remove the N,N-diethyl-2,3,3,3-tetrafluoropriopionamide by-product. Then, methylene chloride (30 mL) is added to the resulting slurry to dissolve all solids. The organic layer is separated and the solvent is exchanged to n-propyl acetate to a final volume of 17–18 mL. The resulting slurry is cooled to −20° for 12 hours. The product was collected by filtration and dried under ambient nitrogen to give the title compound, mp=198–203°; NMR (400 MHz, CDCl$_3$) 5.737, 5.690, 3.300, 2.904, 2.164, 1.431, 0.952 and 2.569–1.358 δ; CMR (100 MHz, CDCl$_3$) 198.5, 176.5, 167.4, 152.7, 150.0, 142.8, 126.2, 119.7, 107.1, 105.9, 95.2, 44.1, 42.4, 41.9, 38.5, 37.6, 35.4, 33.9, 32.9, 31.3, 29.1, 26.8, 23.2, 14.1 and 13.4 δ; MS calculated for C$_{27}$H$_{33}$O$_4$=421.238 (M+H$^+$), found=421.2 m/z.

Example 32

9α,11α-Epoxy-17β-hydroxypregn-4-en-3-one-7α,21-dicarboxylic acid, γ-lactone (VI)

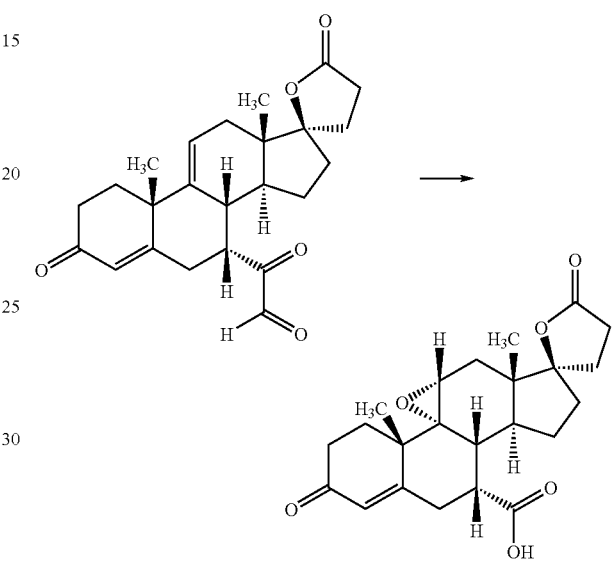

A mixture of 17β-hydroxy-7α-(2'-oxoacetyl)-pregna-4,9 (11)-dien-3-one-21-carboxylic acid, γ-lactone (V, EXAMPLE 11, 6.7 mg, 0.0169 mmoles) in methylene chloride (0.5 ml) is treated with peracetic acid (35%, 4 μl, containing 1.58 mg, 0.0208 mmoles, 1.23 equivalents of peracetic acid), stirred at 20–25° for 25 hours, then treated with more peracetic acid (35%, 2 μl, containing 79 mg, 0.0104 mmoles, 0.62 equivalents of peracetic acid), then stirred at 20–25° for 49 hrs., at which time LC analysis indicated conversion to the title compound, LC-UV (λ$_{max}$=244 nm); LC-MS (m/e 400).

Example 33

7α-Allyl-17β-hydroxypregna-4,9(11)-dien-3-one, 21-carboxylic acid, γ-lactone (II)

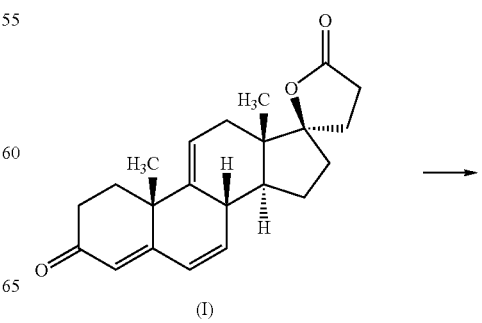

(I)

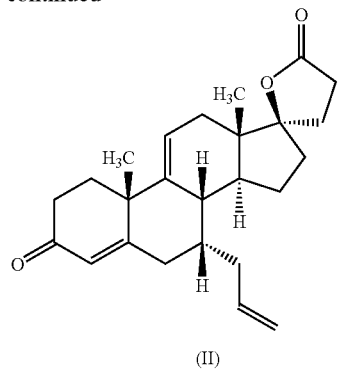

(II)

A mixture of 17β-hydroxypregna-4,6,9(11)-trien-3-one-21-carboxylic acid, γ-lactone (I, 1.0171 g, 3.0052 mmoles) in methylene chloride (62 ml) is cooled to −30° and treated with titanium tetrachloride in methylene chloride (1.0 M, 15.0 ml, 15.0 mmoles, 4.99 equivalents). The resulting mixture is treated with allyltrimethylsilane (3.0 ml, 2.16 g, 18.876 mmoles, 6.28 equivalents) and stirred at −30° for 4 hrs., at which time conversion of the starting material into the product ($R_f$=0.27) is nearly complete by TLC (ethyl acetate/cyclohexane, 35/65). The reaction mixture is quenched with water (25 ml), extracted with methylene chloride (3×25 ml), and concentrated. The concentrate (weight=1.6262 g) is flash chromatographed (silica silica gel, 150 g; gradient elution with ethyl acetate/cyclohexane, 15%→55%). The fractions containing the more polar product ($R_f$=0.27) are combined and concentrated to give the title compound, UV $\lambda_{max}$=241 nm; CMR (100 MHz, $CDCl_3$) 198.65, 176.46, 167.31, 143.22, 136.36, 126.51, 119.84, 116.80, 95.22, 44.15, 42.50, 41.13, 40.73, 37.33, 35.56, 35.43, 34.13, 33.78, 33.05, 31.65, 31.37, 29.14, 26.86, 23.04, and 13.78 δ; NMR (400 MHz, $CDCl_3$) 0.94, 1.37, 1.4–2.6, 4.95, 5.01, 5.65 and 5.74 δ; MS (CI, $NH_3$), m/e=381 (P+H, 100%);

The product is rechromatographed (silica gel, 60 g; gradient elution with ethyl acetate/cyclohexane, 15%→45%) to remove a more polar impurity ($R_f$=0.06). The product-containing fractions are combined and concentrated. A portion of the residue (96.8 mg) is taken up in methylene chloride (1 ml), diluted with ethyl acetate (2 ml), concentrated to a volume of less than 1 ml, and cooled to 0°. The supernatant is decanted and the crystals recrystallized from ethyl acetate at 0°. An X-ray crystallographic study confirmed the assignment as 7α-allyl-17β-hydroxypregna-4,9(11)-dien-3-one, 21-carboxylic acid, γ-lactone.

Example 34

5α,17β-Dihydroxypregn-9(11)-ene-3-one, 7α,21-dicarboxylic acid, bis-γ-lactone (VII)

Step (1)-17β-Hydroxypregna-4,9(11)-dien-3-one-7α,21-dicarboxylic acid, γ-lactone (VI)

A mixture of 17β-hydroxy-7α-(5'-methyl-2'-furyl)-pregna-4,9(1 I)-dien-3-one-21-carboxylic acid, γ-lactone (II, EXAMPLE 3, 20 g, 47.5568 mmoles) in methanol (60 ml) and methylene chloride (60 ml) is cooled to −55°. Ozone in oxygen is bubbled through this mixture until 0.8 area % (by LC) of starting material (II) remains. The mixture is purged of ozone by sparging with nitrogen and then quenched with dimethylsulfide (16 ml, 13.5 g, 217.9 mmoles, 4.58 equivalents), warmed to 20–25°, stirred at 20–25° for 50 min. The resulting mixture is concentrated to 80 ml, methanol (25 ml) is added, and concentrated to 80 ml again. The mixture is then treated, at 5°, with a solution of potassium bicarbonate (21.6 g; 215.7 mmoles; 4.54 equivalents) in water (44 ml) followed by hydrogen peroxide (50% aqueous, 23.5 g, containing 11.75 g (345.5 mmoles, 7.27 equivalents) of hydrogen peroxide). After warming to 20–30° for one hour the mixture is quenched with dimethylsulfide (8 ml, 6.75 g, 108.95 mmoles, 2.29 equivalents). Methylene chloride (20 ml) is added, and the pH adjusted to 3 with hydrogen chloride (31.5% aqueous, 26.0 g containing 8.19 g (224.4 mmoles; 4.72 equivalents) of hydrogen chloride. The mixture is warmed to dissolve and the phases separated. The upper aqueous phase is extracted with methylene chloride (10 ml) and the combined organic phases are extracted with water (10 ml.). LC was performed on the methylene chloride mixture (after aqueous workup) under the following conditions:

| | |
|---|---|
| Column: | Supelco Discovery RP Amide C16; 5 μ; 250 mm × 4 mm |
| Flow: | 1 ml/min |
| Detection: | UV; 240 nm |
| Mobile Phase: | A: 950 g Water; 39 g Acetonitrile; 1.0 g Trifluoroacetic acid B: 754 g Acetonitrile; 39 g Water; 1.0 g Trifluoroacetic acid |
| Gradient: | $T_0$: 80% A/20% B $T_{15}$: 20% A/80% B $T_{15.1}$: 80% A/20% B $T_{20}$: 80% A/20% B |
| Run Time: | 20 minutes |
| Flow: | 1 ml/min |
| Injection Volume: | 5 λ |
| Sample Prep: | 5 λ or reaction mixture into 1 ml of 1/1 Acetonitrile: phosphate buffer (1 ml phosphoric acid in 1 1 water; pH to 2.4 with sodium hydroxide) |

The reaction LC major peak (72 area %) was at 10.52 minutes; retention time of a known standard of the carboxylic acid (VI) is 10.52 minutes.

Step (2)-5α,17β-Dihydroxypregn-9(11)-ene-3-one, 7α,21-dicarboxylic acid, bis-γ-lactone (VII)

The resulting organic phase containing 17β-hydroxypregna-4,9(11)-dien-3-one-7α,21-dicarboxylic acid, γ-lactone (VI) is concentrated to 40 ml and para-toluene sulfonic acid monohydrate (10 mg; 0.042 mmoles; 0.001 equivalents) dissolved in acetone (15 ml) is added. Crystallization is observed after 30 minutes at reflux. The resulting slurry is concentrated to 50 ml and concentration continued while maintaining a constant volume by the addition of fresh acetone. After 80 ml of acetone has been added the slurry is cooled to 0° and the solids collected by filtration to give the title compound, CMR (100 MHz, $CDCl_3$) 206.07, 176.44, 175.41, 139.66, 123.98, 94.88, 90.99, 47.09, 43.91, 42.36, 41.57, 41.08, 38.93, 36.98, 35.17, 33.01, 32.44, 31.36, 29.10, 23.08, 22.99 and 14.24 δ; NMR (400 MHz, $CDCl_3$) 0.94, 1.41, 1.5–2.6, 2.80 and 5.70 δ.

Example 35

17β-hydroxypregna-4,9(11)-dien-3-one-7α,21-dicarboxylic acid, γ-lactone, methyl ester (CII)

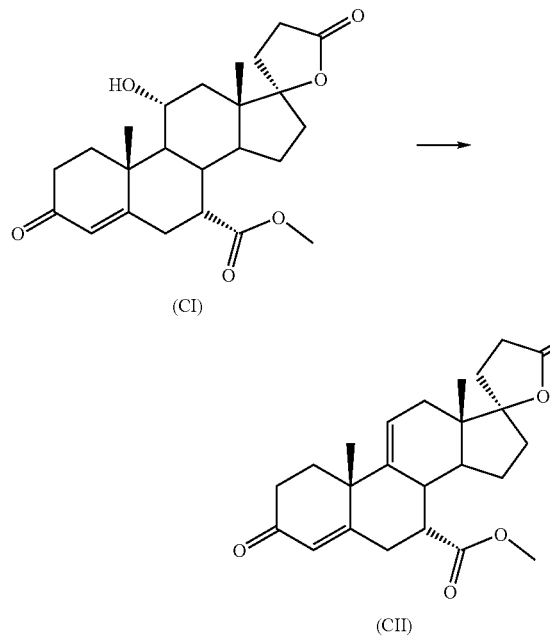

11α,17β-dihydroxypregn-4-en-3-one-7α,21-dicarboxylic acid, γ-lactone, methyl ester (CI, *Drugs of the Future*, 24(5), 488–501 (1999), compound (VI) and International Publication WO98/25948, pages 76 and 280; 5.00 g, 12.0 mmol) is mixed with acetonitrile (15 ml). N-(1,1,2,3,3,3)hexafluoropropyl)-diethylamine (CVI, 2.55 ml, 14.4 mmol) is added to this the steroid mixture and heated to 60° for 2.5 hours. The resulting mixture is cooled to 20–25° and the reaction is quenched with methanol (100 µL). A saturated aqueous solution of potassium bicarbonate (15 ml) is added. The acetonitrile is then removed under reduced pressure. The resulting mixture is extracted with methylene chloride (3×10 ml). The combined organic phases are washed with a aqueous solution of sodium chloride (10%, 20 ml). The solvent is dried with magnesium sulfate. The solvent is exchanged from methylene chloride to methyl t-butyl ether (MTBE). The mixture is concentrated to a final volume of 25 ml. The resulting slurry is stirred overnight and the final product, the title compound, is collected by filtration.

Example 36

17β-hydroxypregna-4,9(11)-dien-3-one-7α,21-dicarboxylic acid, γ-lactone, Methyl Ester (CII)

11α,17β-dihydroxypregn-4-en-3-one-7α,21-dicarboxylic acid, γ-lactone, methyl ester (CI, 5.00 g, 12.0 mmol) is placed in a flask with acetonitrile (15 ml). To this mixture the Ishikawa reagent (2.55 ml, 14.4 mmol) is added and heated to 60° for 2 hrs. The mixture is cooled to 20–25° and the reaction is quenched with aqueous potassium bicarbonate (20% solution, 18 ml). The acetonitrile is removed under reduced pressure, the aqueous layer is extracted with methylene chloride (3×5 ml). The combined organic phases are washed with sodium chloride solution (10%, 10 ml). The solvent is exchanged from methylene chloride to methyl isobutyl ketone/heptane to crystallize the title compound, mp=198.6–199.5°; MS (m/z) calculated for $C_{24}H_{30}O_5$=398.5 (M+), found 398.9(M+); NMR (CDCl$_3$) 5.69, 5.64, 3.62, 2.97, 2.84–1.47, 1.38 and 0.93 δ; CMR (CDCl$_3$) 98.5, 176.4, 172.5, 166.5, 142.3, 125.6, 118.9, 95.0, 51.3, 43.0, 40.3, 35.6, 35.2, 34.1, 33.7, 32.8, 31.2, 29.0, 27.1, 23.2 and 14.0 δ.

Example 37

17β-hydroxypregna-4,9(11)-dien-3-one-7α,21-dicarboxylic acid, γ-lactone, methyl ester (CII)

11α,17β-dihydroxypregn-4-en-3-one-7α,21-dicarboxylic acid, γ-lactone, methyl ester (CI, 80.00 g, 192.1 mmol) is placed in a flask with acetonitrile (80 ml). To this mixture the Ishikawa reagent (40.8 ml, 224.8 mmol) is added and heated slowly to 45 to 50°, then held for 1–2 hours. The mixture is cooled to 20–25° and the reaction is quenched with aqueous potassium bicarbonate (72 g in 288 ml). Methylene chloride (240 ml) is added and after mixing the layers are separated. The aqueous phase is extracted with methylene chloride (100 ml). The combined organic phases are washed with water (240 ml). The solvent is exchanged from methylene chloride to methyl tert-butyl ether, and branched octane is added drop wise to crystallize the product which is the title compound.

Example 38

17β-hydroxypregna-4,9(11)-dien-3-one-7α,21-dicarboxylic acid, γ-lactone, methyl ester (CII)

11α,17β-dihydroxypregn-4-en-3-one-7α,21-dicarboxylic acid, γ-lactone, methyl ester (CI, 80.00 g, 192.1 mmol) is placed in a flask with acetonitrile (80 ml). To this mixture the Ishikawa reagent (40.8 ml, 224.8 mmol) is added and heated slowly to 55 to 50°, then held for 1–2 hours. The mixture is cooled to 20–25° and the reaction is quenched with aqueous potassium bicarbonate (37.3 g in 288 ml). Methylene chloride (240 ml) is added and after mixing the layers are separated. The aqueous phase is extracted with methylene chloride (100 ml). The combined organic phases are washed with water (80 ml). The solvent is exchanged from methylene chloride to methyl iso-butyl ketone, and branched octane is added drop wise to crystallize the product which is the title compound.

Example 39

Crystalline 17β-hydroxy-7α-(5'-methyl-2'-furyl)-pregna-4,9(11)-dien-3-one-21-carboxylic acid, γ-lactone (II)

A sample of 17β-hydroxy-7α-(5'-methyl-2'-furyl)-pregna-4,9(11)-dien-3-one-21-carboxylic acid, γ-lactone (II) produced by the process of one of EXAMPLEs 3, 13, 21, 24, 31 or 34, or following the general procedure of these EXAMPLEs and making non-critical variations, is obtained in crystalline form and tested by powder X-ray diffraction (PXRD) as follows. 17β-Hydroxy-7α-(5'-methyl-2'-furyl)-pregna-4,9(11)-dien-3-one-21-carboxylic acid, γ-lactone (II) is ground for 30 seconds using a mortar and pestle. The ground sample is placed on zero-background sample holders containing a thin layer of Vaseline™. The sample is examined by PXRD using the Rigaku Miniflex X-ray diffractometer. The diffraction pattern is collected with the sample spinning.

Experimental Conditions for Powder X-Ray Diffraction (XRD):

A Rigaku Miniflex+X-ray diffractometer was used for the acquisition of the powder XRD patterns. The instrument operates using the Cu Kai emission with a nickel filter at 1.50451. The major instrumental parameters are set or fixed at:

| X-ray: | Cu/30 kV (fixed)/15 mA (fixed) |
|---|---|
| Divergence Slit: | Variable |
| Scattering Slit: | 4.2° (fixed) |
| Receiving Slit: | 0.3 mm (fixed) |
| Scan Mode: | FT |
| Preset Time: | 2.0 sec. |
| Scan Width: | 0.050° |
| Scan Axis: | 2Theta/Theta |
| Scan Range: | 3.000° to 40.000° |

The results of the PXRD are as follows:

| Two-Theta Angle (°) | d-spacing (Å) | Relative Intensity (%) |
|---|---|---|
| 6.503 | 13.5812 | 1.1 |
| 10.589 | 8.3479 | 58.3 |
| 11.557 | 7.6505 | 18.2 |
| 12.686 | 6.9721 | 4.0 |
| 14.248 | 6.2111 | 100.0 |
| 15.144 | 5.8455 | 28.3 |
| 16.608 | 5.3334 | 50.6 |
| 17.851 | 4.9647 | 84.5 |
| 18.353 | 4.8300 | 28.2 |
| 19.537 | 4.5399 | 8.3 |
| 20.148 | 4.4037 | 22.6 |
| 21.147 | 4.1977 | 28.0 |
| 21.695 | 4.0930 | 18.6 |
| 23.199 | 3.8309 | 35.1 |
| 24.757 | 3.5933 | 13.5 |
| 25.241 | 3.5255 | 6.0 |
| 25.905 | 3.4365 | 25.7 |
| 27.400 | 3.2523 | 18.1 |
| 28.262 | 3.1551 | 2.5 |
| 28.750 | 3.1026 | 8.4 |
| 29.955 | 2.9805 | 2.9 |
| 30.959 | 2.8861 | 8.2 |
| 31.950 | 2.7988 | 3.6 |
| 32.685 | 2.7375 | 2.3 |
| 33.207 | 2.6957 | 3.2 |
| 33.888 | 2.6431 | 4.0 |
| 34.356 | 2.6081 | 1.7 |
| 35.607 | 2.5193 | 2.7 |
| 36.144 | 2.4831 | 25.6 |
| 37.061 | 2.4237 | 4.5 |
| 37.797 | 2.3782 | 1.4 |
| 38.496 | 2.3366 | 2.4 | where
Two-Theta Angle is measured in degrees;
d-Spacing is measured in angstroms; and
Relative Intensity is the intensity percentage of each peak relative to the strongest peak at 14.248 degrees.

Example 40

Crystalline 17β-hydroxy-7α-(5'-methyl-2'-furyl)-pregna-4,9(11)-dien-3-one-21-carboxylic acid, γ-lactone (II)

Following the general procedure of EXAMPLE 39 and making non-critical variations another sample of crystalline 17β-hydroxy-7α-(5'-methyl-2'-furyl)-pregna-4,9(11)-dien-3-one-21-carboxylic acid, γ-lactone (11) is subjected to PXRD with with spin with the following results:

| Two-Theta Angle (°) | d-spacing (Å) | Relative Intensity (%) |
|---|---|---|
| 6.506 | 13.5742 | 1.1 |
| 10.603 | 8.3366 | 49 |
| 11.600 | 7.6220 | 17.7 |
| 12.699 | 6.9648 | 2.4 |
| 14.297 | 6.1900 | 100 |
| 15.159 | 5.8398 | 18.8 |
| 16.206 | 5.4648 | 7.2 |
| 16.650 | 5.3202 | 39.6 |
| 17.900 | 4.9512 | 59.4 |
| 18.397 | 4.8186 | 27 |
| 19.593 | 4.5270 | 8.5 |
| 20.155 | 4.4022 | 27.5 |
| 21.194 | 4.1886 | 22.4 |
| 21.702 | 4.0916 | 15.7 |
| 23.247 | 3.8231 | 24.5 |
| 24.805 | 3.5865 | 13.1 |
| 25.256 | 3.5234 | 6.2 |
| 25.948 | 3.4310 | 29.2 |
| 27.452 | 3.2464 | 14.8 |
| 28.353 | 3.1452 | 3 |
| 28.800 | 3.0974 | 7.3 |
| 29.952 | 2.9808 | 2.2 |
| 31.003 | 2.8821 | 7.2 |
| 31.988 | 2.7956 | 3.3 |
| 32.666 | 2.7391 | 1.3 |
| 33.245 | 2.6926 | 3.4 |
| 33.902 | 2.6420 | 2 |
| 34.392 | 2.6055 | 1.4 |
| 35.651 | 2.5163 | 1.9 |
| 36.192 | 2.4799 | 14.9 |
| 37.105 | 2.4209 | 4.4 |
| 37.817 | 2.3770 | 1.6 |
| 38.547 | 2.3336 | 2.4 |
| 39.394 | 2.2854 | 1.6 |

Example 41

Crystalline 17β-hydroxy-7α-(5'-methyl-2'-furyl)-pregna-4,9(11)-dien-3-one-21-carboxylic acid, γ-lactone (II)

Following the general procedure of EXAMPLE 39 and making non-critical variations another sample of crystalline 17β-hydroxy-7α-(5'-methyl-2'-furyl)-pregna-4,9(11)-dien-3-one-21-carboxylic acid, γ-lactone (II) is subjected to PXRD with spin with the following results:

| Two-Theta Angle (°) | d-spacing (Å) | Relative Intensity (%) |
|---|---|---|
| 6.536 | 13.5120 | 1.2 |
| 10.505 | 8.4141 | 43.6 |
| 11.548 | 7.6564 | 15.7 |
| 12.613 | 7.0121 | 3.6 |
| 14.251 | 6.2099 | 100 |
| 15.142 | 5.8463 | 29.2 |
| 16.598 | 5.3368 | 31.6 |
| 17.848 | 4.9655 | 59.3 |
| 18.349 | 4.8310 | 34.5 |
| 19.543 | 4.5386 | 11.7 |
| 20.140 | 4.4054 | 24.3 |
| 21.002 | 4.2264 | 29.1 |
| 21.653 | 4.1008 | 15 |
| 23.197 | 3.8312 | 48 |
| 24.754 | 3.5936 | 14 |
| 25.945 | 3.4314 | 25 |
| 27.403 | 3.2520 | 21.4 |

-continued

| Two-Theta Angle (°) | d-spacing (Å) | Relative Intensity (%) |
|---|---|---|
| 28.749 | 3.1027 | 11.1 |
| 29.991 | 2.9770 | 2.2 |
| 30.953 | 2.8867 | 8.1 |
| 31.857 | 2.8067 | 3 |
| 32.683 | 2.7376 | 1.4 |
| 33.667 | 2.6599 | 3.3 |
| 36.106 | 2.4856 | 13.5 |
| 37.054 | 2.4242 | 5.5 |
| 37.795 | 2.3783 | 2.2 |
| 38.460 | 2.3387 | 2.7 |

Example 42

Crystalline 17β-hydroxy-7α-(5'-methyl-2'-furyl)-pregna-4,9(11)-dien-3-one-21-carboxylic acid, γ-lactone (II)

Following the general procedure of EXAMPLE 39 and making non-critical variations another sample of crystalline 17β-hydroxy-7α-(5'-methyl-2'-furyl)-pregna-4,9(11)-dien-3-one-21-carboxylic acid, γ-lactone (II) is subjected to PXRD with spin with the following results:

| Two-Theta Angle (°) | d-spacing (Å) | Relative Intensity (%) |
|---|---|---|
| 6.508 | 13.5698 | 1.4 |
| 10.590 | 8.3470 | 51.6 |
| 11.549 | 7.6557 | 16.7 |
| 12.614 | 7.0118 | 2.5 |
| 14.247 | 6.2116 | 100 |
| 15.147 | 5.8443 | 25.2 |
| 16.156 | 5.4815 | 8.5 |
| 16.637 | 5.3241 | 42.4 |
| 17.854 | 4.9638 | 66.6 |
| 18.345 | 4.8320 | 27.2 |
| 19.547 | 4.5376 | 9.5 |
| 20.143 | 4.4048 | 26.2 |
| 21.051 | 4.2167 | 28.1 |
| 21.691 | 4.0937 | 17.4 |
| 23.240 | 3.8243 | 34.5 |
| 24.797 | 3.5875 | 13.2 |
| 25.207 | 3.5301 | 7.1 |
| 25.903 | 3.4368 | 25.8 |
| 27.404 | 3.2519 | 16.1 |
| 28.261 | 3.1552 | 2.1 |
| 28.752 | 3.1024 | 7.4 |
| 29.994 | 2.9767 | 2.3 |
| 30.955 | 2.8865 | 9.7 |
| 31.938 | 2.7999 | 2.9 |
| 32.586 | 2.7456 | 2 |
| 33.196 | 2.6965 | 3.2 |
| 33.711 | 2.6565 | 2.3 |
| 34.315 | 2.6111 | 1.4 |
| 35.642 | 2.5169 | 3.2 |
| 36.147 | 2.4829 | 16.2 |
| 37.092 | 2.4218 | 4.1 |
| 37.798 | 2.3781 | 2.1 |
| 38.469 | 2.3382 | 2.1 |

Example 43

Crystalline 17β-hydroxy-7α-(5'-methyl-2'-furyl)-pregna-4,9(11)-dien-3-one-21-carboxylic acid, γ-lactone (II)

Following the general procedure of EXAMPLE 39 and making non-critical variations another sample of crystalline 17β-hydroxy-7α-(5'-methyl-2'-furyl)-pregna-4,9(11)-dien-3-one-21-carboxylic acid, γ-lactone (II) is subjected to PXRD with spin with the following results:

| Two-Theta Angle (°) | d-spacing (Å) | Relative Intensity (%) |
|---|---|---|
| 10.596 | 8.3424 | 29.9 |
| 11.597 | 7.6245 | 16.6 |
| 12.658 | 6.9877 | 2.6 |
| 14.296 | 6.1904 | 100 |
| 15.192 | 5.8272 | 23.4 |
| 16.652 | 5.3193 | 30.3 |
| 17.899 | 4.9514 | 46.1 |
| 18.401 | 4.8176 | 29.1 |
| 19.557 | 4.5352 | 8.5 |
| 20.158 | 4.4015 | 24.5 |
| 21.000 | 4.2269 | 21.8 |
| 21.706 | 4.0909 | 14.4 |
| 23.246 | 3.8232 | 32 |
| 24.846 | 3.5805 | 13.6 |
| 25.953 | 3.4303 | 17.7 |
| 27.447 | 3.2469 | 15 |
| 28.798 | 3.0976 | 7.5 |
| 30.002 | 2.9760 | 2.7 |
| 31.003 | 2.8821 | 7.5 |
| 31.955 | 2.7984 | 1.2 |
| 32.697 | 2.7366 | 1.5 |
| 33.247 | 2.6925 | 4.2 |
| 33.708 | 2.6567 | 1.7 |
| 34.372 | 2.6069 | 1.6 |
| 35.645 | 2.5167 | 1.9 |
| 36.154 | 2.4824 | 11.1 |
| 37.145 | 2.4184 | 4.4 |
| 37.843 | 2.3754 | 1.3 |
| 38.537 | 2.3342 | 2.5 |

Example 44

Crystalline 17β-hydroxy-7α-(5'-methyl-2'-furyl)-pregna-4,9(11)-dien-3-one-21-carboxylic acid, γ-lactone (II)

Following the general procedure of EXAMPLE 39 and making non-critical variations another sample of crystalline 17β-hydroxy-7α-(5'-methyl-2'-furyl)-pregna-4,9(11)-dien-3-one-21-carboxylic acid, γ-lactone (II) is subjected to PXRD with spin with the following results:

| Two-Theta Angle (°) | d-spacing (Å) | Relative Intensity (%) |
|---|---|---|
| 10.647 | 8.3025 | 40.1 |
| 11.602 | 7.6207 | 16.1 |
| 12.747 | 6.9388 | 3.3 |
| 14.300 | 6.1887 | 100 |
| 15.194 | 5.8263 | 25.7 |
| 16.692 | 5.3068 | 40.3 |
| 17.945 | 4.9389 | 68.4 |
| 18.401 | 4.8176 | 31.3 |
| 19.591 | 4.5275 | 8.5 |
| 20.154 | 4.4023 | 28.1 |
| 21.003 | 4.2262 | 26.5 |
| 21.707 | 4.0908 | 15.6 |
| 23.247 | 3.8231 | 34.4 |
| 24.847 | 3.5804 | 19 |
| 25.956 | 3.4300 | 30.3 |
| 27.451 | 3.2464 | 18.5 |
| 28.845 | 3.0926 | 9.8 |
| 29.958 | 2.9802 | 3.5 |
| 31.044 | 2.8784 | 9.7 |
| 32.039 | 2.7912 | 1.6 |
| 32.716 | 2.7350 | 2 |
| 33.256 | 2.6918 | 4.5 |

-continued

| Two-Theta Angle (°) | d-spacing (Å) | Relative Intensity (%) |
|---|---|---|
| 33.713 | 2.6564 | 2.8 |
| 34.330 | 2.6100 | 2.2 |
| 35.652 | 2.5162 | 3.2 |
| 36.196 | 2.4796 | 17 |
| 37.146 | 2.4184 | 5.9 |
| 37.804 | 2.3778 | 2.2 |
| 38.544 | 2.3338 | 2.7 |

Example 45

Crystalline 17β-hydroxy-7α-(5'-methyl-2'-furyl)-pregna-4,9(11)-dien-3-one-21-carboxylic acid, γ-lactone (II)

Following the general procedure of EXAMPLE 39 and making non-critical variations another sample of crystalline 17β-hydroxy-7α-(5'-methyl-2'-furyl)-pregna-4,9(11)-dien-3-one-21-carboxylic acid, γ-lactone (II) is subjected to PXRD with the following results:

| Two-Theta Angle (°) | d-spacing (Å) | Relative Intensity (%) |
|---|---|---|
| 6.594 | 13.3929 | 1 |
| 10.604 | 8.3359 | 42.2 |
| 11.602 | 7.6212 | 16.6 |
| 12.699 | 6.9652 | 2.8 |
| 14.305 | 6.1866 | 100 |
| 15.200 | 5.8242 | 29.4 |
| 16.654 | 5.3188 | 50.3 |
| 17.943 | 4.9395 | 74.3 |
| 18.442 | 4.8069 | 27 |
| 19.607 | 4.5239 | 10 |
| 20.200 | 4.3925 | 23.9 |
| 21.051 | 4.2166 | 28.2 |
| 21.746 | 4.0834 | 16.8 |
| 23.291 | 3.8161 | 32.9 |
| 24.851 | 3.5798 | 13.5 |
| 25.299 | 3.5175 | 8.1 |
| 25.994 | 3.4250 | 27.2 |
| 27.456 | 3.2458 | 18.3 |
| 28.352 | 3.1453 | 3.1 |
| 28.845 | 3.0926 | 8 |
| 30.053 | 2.9710 | 2.9 |
| 31.005 | 2.8819 | 7.5 |
| 31.949 | 2.7989 | 2.3 |
| 33.254 | 2.6920 | 3.5 |
| 33.949 | 2.6384 | 2.6 |
| 34.400 | 2.6049 | 1.9 |
| 35.653 | 2.5162 | 3.2 |
| 36.196 | 2.4796 | 16.2 |
| 37.190 | 2.4156 | 5.1 |
| 37.840 | 2.3756 | 1.9 |
| 38.554 | 2.3332 | 2.9 |

Example 46

Crystalline 17β-hydroxy-7α-(5'-methyl-2'-furyl)-pregna-4,9(11)-dien-3-one-21-carboxylic acid, γ-lactone (II)

Following the general procedure of EXAMPLE 39 and making non-critical variations another sample of crystalline 17β-hydroxy-7α-(5'-methyl-2'-furyl)-pregna-4,9(11)-dien-3-one-21-carboxylic acid, γ-lactone (II) is subjected to PXRD with spin with the following results:

| Two-Theta Angle (°) | d-spacing (Å) | Relative Intensity (%) |
|---|---|---|
| 10.699 | 8.2622 | 53.4 |
| 11.702 | 7.5562 | 11.8 |
| 12.790 | 6.9156 | 2.2 |
| 14.356 | 6.1644 | 73.4 |
| 15.298 | 5.7872 | 21.2 |
| 16.743 | 5.2908 | 66.4 |
| 18.005 | 4.9225 | 100 |
| 18.456 | 4.8034 | 23.1 |
| 19.698 | 4.5031 | 6.6 |
| 20.297 | 4.3716 | 23 |
| 21.252 | 4.1772 | 29 |
| 21.800 | 4.0735 | 10.8 |
| 23.348 | 3.8068 | 29.8 |
| 24.949 | 3.5661 | 12 |
| 25.346 | 3.5111 | 4.4 |
| 26.003 | 3.4238 | 28.7 |
| 27.547 | 3.2353 | 17.1 |
| 28.494 | 3.1300 | 4.4 |
| 28.854 | 3.0917 | 6.6 |
| 30.140 | 2.9626 | 1.9 |
| 31.103 | 2.8731 | 7.1 |
| 32.054 | 2.7900 | 3.7 |
| 33.316 | 2.6871 | 1.6 |
| 33.999 | 2.6347 | 4.9 |
| 35.751 | 2.5095 | 2.5 |
| 36.297 | 2.4730 | 27 |
| 37.206 | 2.4146 | 3.9 |
| 37.908 | 2.3715 | 1.5 |
| 38.643 | 2.3281 | 2.3 |

Example 47

Crystalline 17β-hydroxy-7α-(5'-methyl-2'-furyl)-pregna-4,9(11)-dien-3-one-21-carboxylic acid, γ-lactone (II)

Following the general procedure of EXAMPLE 39 and making non-critical variations another sample of crystalline 17β-hydroxy-7α-(5'-methyl-2'-furyl)-pregna-4,9(11)-dien-3-one-21-carboxylic acid, γ-lactone (II) is subjected to PXRD with spin with the following results:

| Two-Theta Angle (°) | d-spacing (Å) | Relative Intensity (%) |
|---|---|---|
| 6.557 | 13.4698 | 1.2 |
| 10.641 | 8.3067 | 49.6 |
| 11.608 | 7.6171 | 12.6 |
| 12.708 | 6.9603 | 2.5 |
| 14.340 | 6.1713 | 100 |
| 15.205 | 5.8221 | 27.9 |
| 16.698 | 5.3048 | 54.7 |
| 17.947 | 4.9383 | 84 |
| 18.446 | 4.8060 | 29.1 |
| 19.606 | 4.5242 | 12.6 |
| 20.202 | 4.3921 | 25.9 |
| 21.053 | 4.2162 | 32.2 |
| 21.752 | 4.0824 | 19.1 |
| 23.295 | 3.8153 | 43.7 |
| 24.855 | 3.5793 | 14.8 |
| 25.300 | 3.5173 | 7 |
| 25.998 | 3.4245 | 31.2 |
| 27.498 | 3.2410 | 21.1 |
| 28.358 | 3.1447 | 3.3 |
| 28.846 | 3.0925 | 9.9 |
| 30.084 | 2.9680 | 2.6 |
| 31.053 | 2.8776 | 9.9 |
| 31.962 | 2.7978 | 2.7 |
| 32.779 | 2.7299 | 1.5 |
| 33.288 | 2.6893 | 3.3 |

-continued

| Two-Theta Angle (°) | d-spacing (Å) | Relative Intensity (%) |
|---|---|---|
| 33.762 | 2.6527 | 3.5 |
| 34.384 | 2.6060 | 1.8 |
| 35.701 | 2.5129 | 3.9 |
| 36.200 | 2.4794 | 18.6 |
| 37.155 | 2.4178 | 5 |
| 37.896 | 2.3722 | 1.8 |
| 38.557 | 2.3330 | 2.8 |

Example 48

Crystalline 17β-hydroxy-7α-(5'-methyl-2'-furyl)-pregna-4,9(11)-dien-3-one-21-carboxylic acid, γ-lactone (II)

Following the general procedure of EXAMPLE 39 and making non-critical variations another sample of crystalline 17β-hydroxy-7α-(5'-methyl-2'-furyl)-pregna-4,9(11)-dien-3-one-21-carboxylic acid, γ-lactone (II) is subjected to PXRD with spin with the following results:

| Two-Theta Angle (°) | d-spacing (Å) | Relative Intensity (%) |
|---|---|---|
| 6.534 | 13.5158 | 1.4 |
| 10.545 | 8.3820 | 53 |
| 11.547 | 7.6569 | 13 |
| 12.644 | 6.9952 | 2.6 |
| 14.248 | 6.2112 | 100 |
| 15.146 | 5.8447 | 27.4 |
| 16.597 | 5.3369 | 55.8 |
| 17.851 | 4.9648 | 84.3 |
| 18.349 | 4.8312 | 28.9 |
| 19.542 | 4.5388 | 12.4 |
| 20.144 | 4.4045 | 23.5 |
| 21.001 | 4.2267 | 36.3 |
| 21.692 | 4.0936 | 20 |
| 23.200 | 3.8308 | 45.9 |
| 24.797 | 3.5876 | 12.9 |
| 25.239 | 3.5256 | 6.1 |
| 25.902 | 3.4369 | 31.2 |
| 27.403 | 3.2520 | 22.7 |
| 28.259 | 3.1554 | 3.8 |
| 28.751 | 3.1025 | 9.9 |
| 29.990 | 2.9771 | 2.4 |
| 30.995 | 2.8828 | 10.4 |
| 31.863 | 2.8063 | 3.2 |
| 32.683 | 2.7377 | 1.7 |
| 33.889 | 2.6430 | 3.7 |
| 35.642 | 2.5169 | 3 |
| 36.143 | 2.4831 | 19.1 |
| 37.098 | 2.4214 | 5 |
| 37.801 | 2.3780 | 1.9 |
| 38.503 | 2.3362 | 2.4 |

Example 49

Crystalline 17β-hydroxy-7α-(5'-methyl-2'-furyl)-pregna-4,9(11)-dien-3-one-21-carboxylic acid, γ-lactone (II)

Following the general procedure of EXAMPLE 39 and making non-critical variations another sample of crystalline 17β-hydroxy-7α-(5'-methyl-2'-furyl)-pregna-4,9(11)-dien-3-one-21-carboxylic acid, γ-lactone (II) is subjected to PXRD with the following results:

| Two-Theta Angle (°) | d-spacing (Å) | Relative Intensity (%) |
|---|---|---|
| 6.464 | 13.6629 | 1.1 |
| 10.457 | 8.4529 | 28.8 |
| 11.482 | 7.7003 | 20.8 |
| 12.546 | 7.0495 | 4.2 |
| 14.185 | 6.2387 | 100.0 |
| 15.056 | 5.8797 | 27.6 |
| 16.099 | 5.5007 | 7.2 |
| 16.545 | 5.3536 | 25.9 |
| 17.792 | 4.9810 | 37.9 |
| 18.253 | 4.8563 | 26.8 |
| 19.455 | 4.5590 | 8.7 |
| 20.056 | 4.4237 | 22.6 |
| 20.858 | 4.2552 | 17.2 |
| 21.604 | 4.1100 | 12.8 |
| 23.139 | 3.8407 | 36.5 |
| 24.741 | 3.5955 | 11.5 |
| 25.152 | 3.5377 | 7.4 |
| 25.848 | 3.4440 | 12.7 |
| 27.347 | 3.2585 | 13.6 |
| 28.700 | 3.1079 | 6.2 |
| 29.910 | 2.9849 | 2.3 |
| 30.898 | 2.8917 | 5.6 |
| 32.599 | 2.7445 | 1.5 |
| 33.142 | 2.7008 | 3.5 |
| 33.633 | 2.6625 | 1.4 |
| 34.265 | 2.6148 | 1.5 |
| 35.520 | 2.5252 | 1.3 |
| 36.055 | 2.4890 | 8.1 |
| 37.016 | 2.4266 | 4.4 |
| 37.735 | 2.3820 | 1.0 |
| 38.415 | 2.3413 | 2.4 |
| 39.349 | 2.2879 | 1.8 |

Example 50

Crystalline 17β-hydroxy-7α-(5'-methyl-2'-furyl)-pregna-4,9(11)-dien-3-one-21-carboxylic acid, γ-lactone (II)

Following the general procedure of EXAMPLE 39 and making non-critical variations another sample of crystalline 17β-hydroxy-7α-(5'-methyl-2'-furyl)-pregna-4,9(11)-dien-3-one-21-carboxylic acid, γ-lactone (II) is subjected to PXRD with spin with the following results:

| Two-Theta Angle (°) | d-spacing (Å) | Relative Intensity (%) |
|---|---|---|
| 10.652 | 8.2987 | 21.1 |
| 11.647 | 7.5915 | 18.4 |
| 12.751 | 6.9370 | 2.4 |
| 14.350 | 6.1673 | 100.0 |
| 15.252 | 5.8044 | 22.5 |
| 16.303 | 5.4325 | 8.5 |
| 16.707 | 5.3020 | 19.7 |
| 17.996 | 4.9252 | 29.0 |
| 18.455 | 4.8037 | 24.7 |
| 19.679 | 4.5076 | 6.1 |
| 20.247 | 4.3823 | 21.0 |
| 21.058 | 4.2154 | 16.1 |
| 21.759 | 4.0812 | 12.6 |
| 23.343 | 3.8076 | 27.8 |
| 24.899 | 3.5731 | 12.2 |
| 25.346 | 3.5111 | 6.1 |
| 26.050 | 3.4177 | 12.1 |
| 27.542 | 3.2358 | 9.5 |
| 28.899 | 3.0870 | 5.7 |
| 30.099 | 2.9666 | 2.3 |
| 31.100 | 2.8733 | 5.6 |
| 32.042 | 2.7909 | 1.3 |

-continued

| Two-Theta Angle (°) | d-spacing (Å) | Relative Intensity (%) |
|---|---|---|
| 32.790 | 2.7290 | 2.2 |
| 33.346 | 2.6848 | 4.5 |
| 33.801 | 2.6496 | 1.1 |
| 34.489 | 2.5983 | 1.4 |
| 35.708 | 2.5124 | 1.8 |
| 36.244 | 2.4765 | 7.9 |
| 37.208 | 2.4145 | 5.0 |
| 37.912 | 2.3712 | 1.5 |
| 38.599 | 2.3306 | 1.2 |

Example 51

Crystalline 17β-hydroxy-7α-(5'-methyl-2'-furyl)-pregna-4,9(11)-dien-3-one-21-carboxylic acid, γ-lactone (II)

Following the general procedure of EXAMPLE 39 and making non-critical variations another sample of crystalline 17β-hydroxy-7α-(5'-methyl-2'-furyl)-pregna-4,9(11)-dien-3-one-21-carboxylic acid, γ-lactone (11) is subjected to PXRD with the following results:

| Two-Theta Angle (°) | d-spacing (Å) | Relative Intensity (%) |
|---|---|---|
| 6.575 | 13.4329 | 1.1 |
| 10.552 | 8.3766 | 29.8 |
| 11.551 | 7.6546 | 15.3 |
| 12.608 | 7.0148 | 3.0 |
| 14.256 | 6.2077 | 100.0 |
| 15.150 | 5.8432 | 28.5 |
| 16.606 | 5.3342 | 29.7 |
| 17.856 | 4.9633 | 49.9 |
| 18.353 | 4.8301 | 20.9 |
| 19.587 | 4.5284 | 7.8 |
| 20.187 | 4.3952 | 19.5 |
| 20.955 | 4.2357 | 17.2 |
| 21.696 | 4.0928 | 15.4 |
| 23.242 | 3.8239 | 41.8 |
| 24.800 | 3.5871 | 13.5 |
| 25.237 | 3.5260 | 5.2 |
| 25.948 | 3.4310 | 17.2 |
| 27.449 | 3.2467 | 16.2 |
| 28.794 | 3.0979 | 8.1 |
| 29.956 | 2.9804 | 2.5 |
| 30.997 | 2.8826 | 5.9 |
| 32.661 | 2.7395 | 0.9 |
| 33.210 | 2.6955 | 3.2 |
| 33.801 | 2.6497 | 2.6 |
| 34.398 | 2.6050 | 1.6 |
| 35.600 | 2.5197 | 1.7 |
| 36.145 | 2.4830 | 11.9 |
| 37.107 | 2.4208 | 4.0 |
| 37.801 | 2.3780 | 1.4 |
| 38.531 | 2.3346 | 2.1 |

Example 52

Crystalline 17β-hydroxy-7α-(5'-methyl-2'-furyl)-pregna-4,9(11)-dien-3-one-21-carboxylic acid, γ-lactone (II)

Following the general procedure of EXAMPLE 39 and making non-critical variations another sample of crystalline 17β-hydroxy-7α-(5'-methyl-2'-furyl)-pregna-4,9(11)-dien-3-one-21-carboxylic acid, γ-lactone (II) is subjected to PXRD with the following results:

| Two-Theta Angle (°) | d-spacing (Å) | Relative Intensity (%) |
|---|---|---|
| 6.575 | 13.4329 | 1.1 |
| 10.552 | 8.3766 | 29.8 |
| 11.551 | 7.6546 | 15.3 |
| 12.608 | 7.0148 | 3.0 |
| 14.256 | 6.2077 | 100.0 |
| 15.150 | 5.8432 | 28.5 |
| 16.606 | 5.3342 | 29.7 |
| 17.856 | 4.9633 | 49.9 |
| 18.353 | 4.8301 | 20.9 |
| 19.587 | 4.5284 | 7.8 |
| 20.187 | 4.3952 | 19.5 |
| 20.955 | 4.2357 | 17.2 |
| 21.696 | 4.0928 | 15.4 |
| 23.242 | 3.8239 | 41.8 |
| 24.800 | 3.5871 | 13.5 |
| 25.237 | 3.5260 | 5.2 |
| 25.948 | 3.4310 | 17.2 |
| 27.449 | 3.2467 | 16.2 |
| 28.794 | 3.0979 | 8.1 |
| 29.956 | 2.9804 | 2.5 |
| 30.997 | 2.8826 | 5.9 |
| 32.661 | 2.7395 | 0.9 |
| 33.210 | 2.6955 | 3.2 |
| 33.801 | 2.6497 | 2.6 |
| 34.398 | 2.6050 | 1.6 |
| 35.600 | 2.5197 | 1.7 |
| 36.145 | 2.4830 | 11.9 |
| 37.107 | 2.4208 | 4.0 |
| 37.801 | 2.3780 | 1.4 |
| 38.531 | 2.3346 | 2.1 |

Example 53

Crystalline 17β-hydroxy-7α-(5'-methyl-2'-furyl)-pregna-4,9(11)dien-3-one-21-carboxylic acid, γ-lactone (II)

Following the general procedure of EXAMPLE 39 and making non-critical variations another sample of crystalline 17β-hydroxy-7α-(5'-methyl-2'-furyl)-pregna-4,9(11)-dien-3-one-21-carboxylic acid, γ-lactone (II) is subjected to PXRD with the following results:

| Two-Theta Angle (°) | d-spacing (Å) | Relative Intensity (%) |
|---|---|---|
| 6.545 | 13.4926 | 1.6 |
| 10.598 | 8.3404 | 27.3 |
| 11.595 | 7.6258 | 15.6 |
| 12.735 | 6.9456 | 2.9 |
| 14.296 | 6.1902 | 100 |
| 15.193 | 5.8268 | 29.5 |
| 16.649 | 5.3203 | 28.8 |
| 17.902 | 4.9506 | 41.1 |
| 18.399 | 4.8181 | 31.6 |
| 19.561 | 4.5344 | 10.4 |
| 20.153 | 4.4025 | 24 |
| 21.049 | 4.2171 | 21.4 |
| 21.708 | 4.0906 | 14.8 |
| 23.253 | 3.8222 | 38.7 |
| 24.804 | 3.5865 | 13.4 |
| 25.289 | 3.5189 | 6.8 |
| 26.006 | 3.4235 | 18.2 |
| 27.492 | 3.2416 | 15.7 |
| 28.802 | 3.0972 | 9 |
| 29.998 | 2.9764 | 2.6 |
| 30.961 | 2.8859 | 8.2 |
| 32.719 | 2.7348 | 1.5 |
| 33.293 | 2.6889 | 3.8 |

-continued
| Two-Theta Angle (°) | d-spacing (Å) | Relative Intensity (%) |
|---|---|---|
| 33.756 | 2.6531 | 2.8 |
| 36.156 | 2.4823 | 11 |
| 37.113 | 2.4204 | 6.2 |
-continued
| Two-Theta Angle (°) | d-spacing (Å) | Relative Intensity (%) |
|---|---|---|
| 37.863 | 2.3742 | 1 |
| 38.550 | 2.3335 | 2.1 |
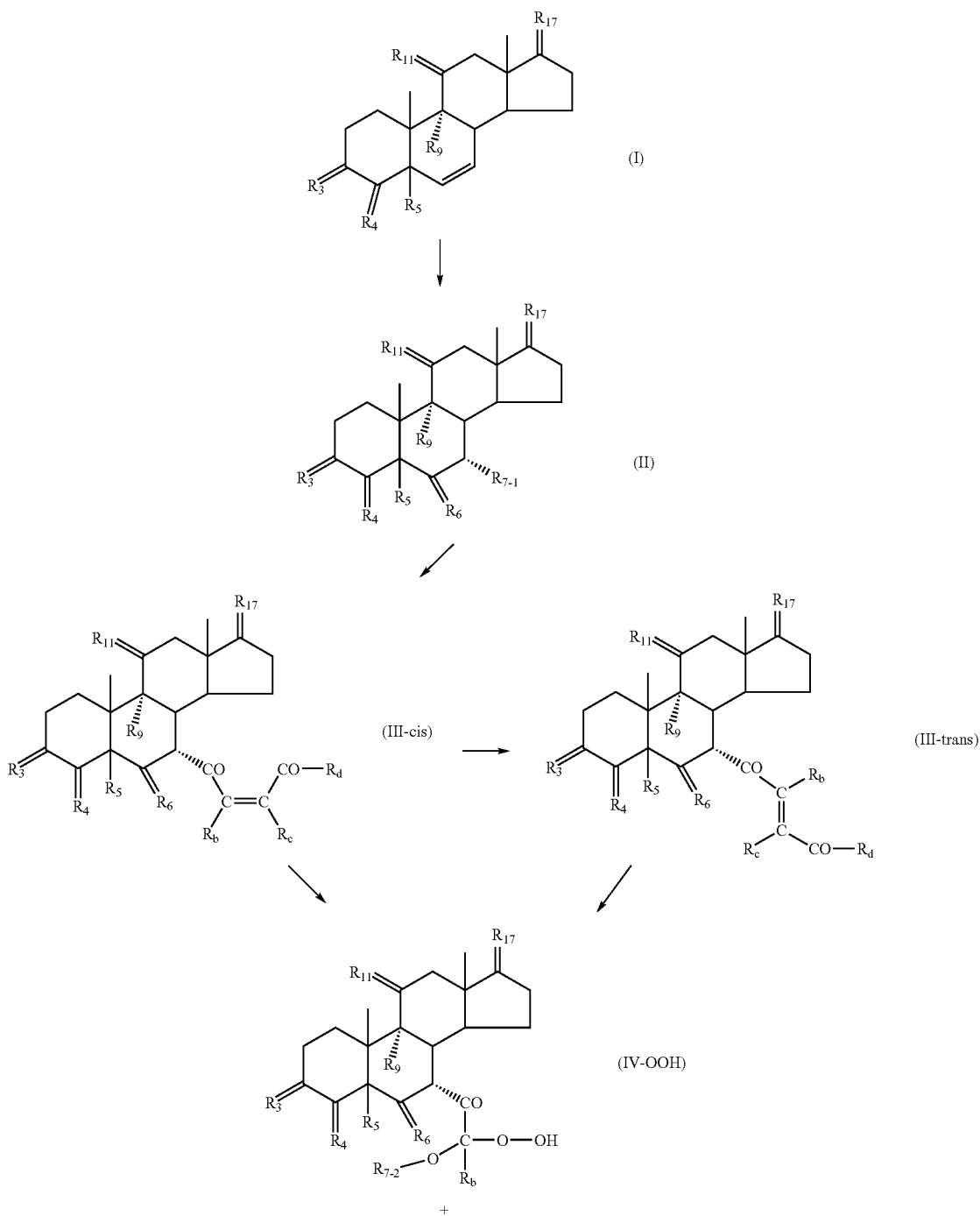

-continued
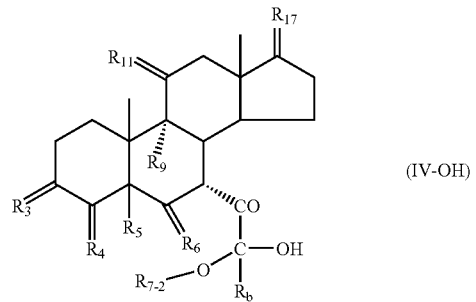
(IV-OH)
+
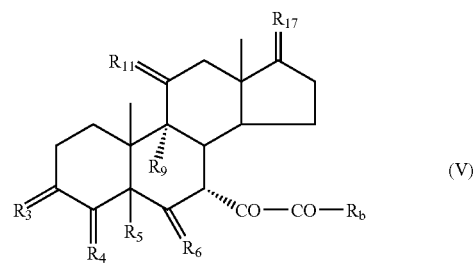
(V)
+
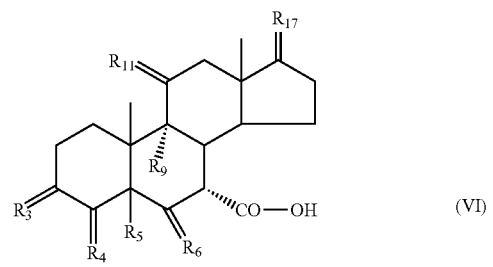
(VI)
+
(IV—OH) + (V)
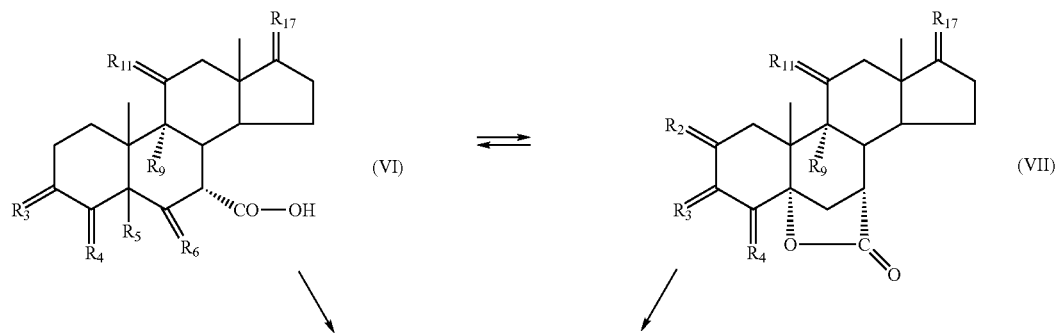

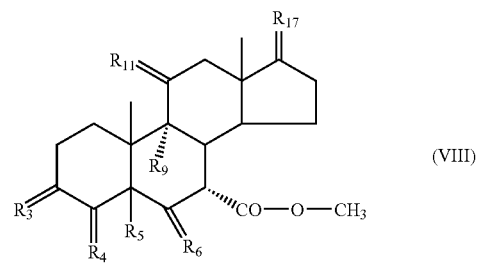
(VIII)
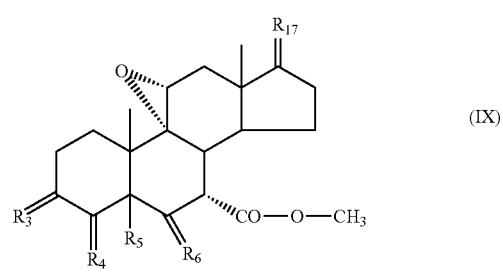
(IX)
CHART B
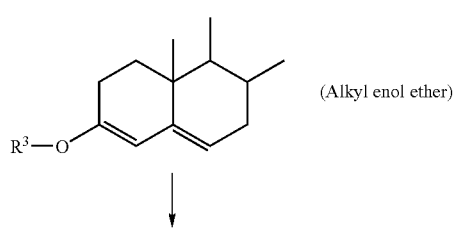
(Alkyl enol ether)
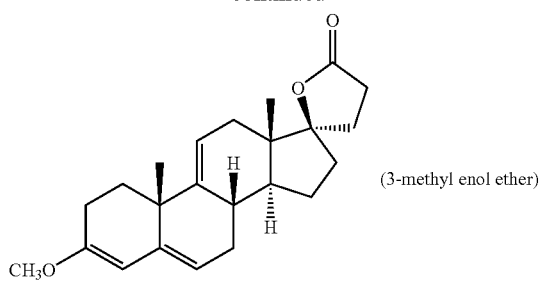
(3-methyl enol ether)
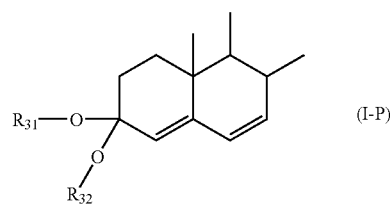
(I-P)
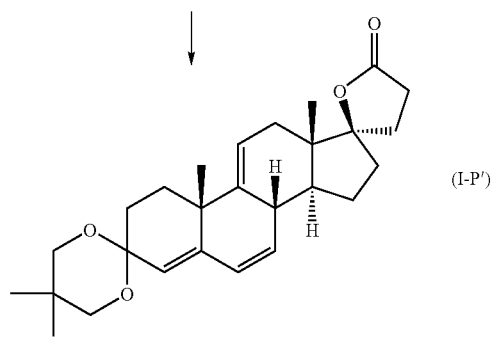
(I-P')

CHART C
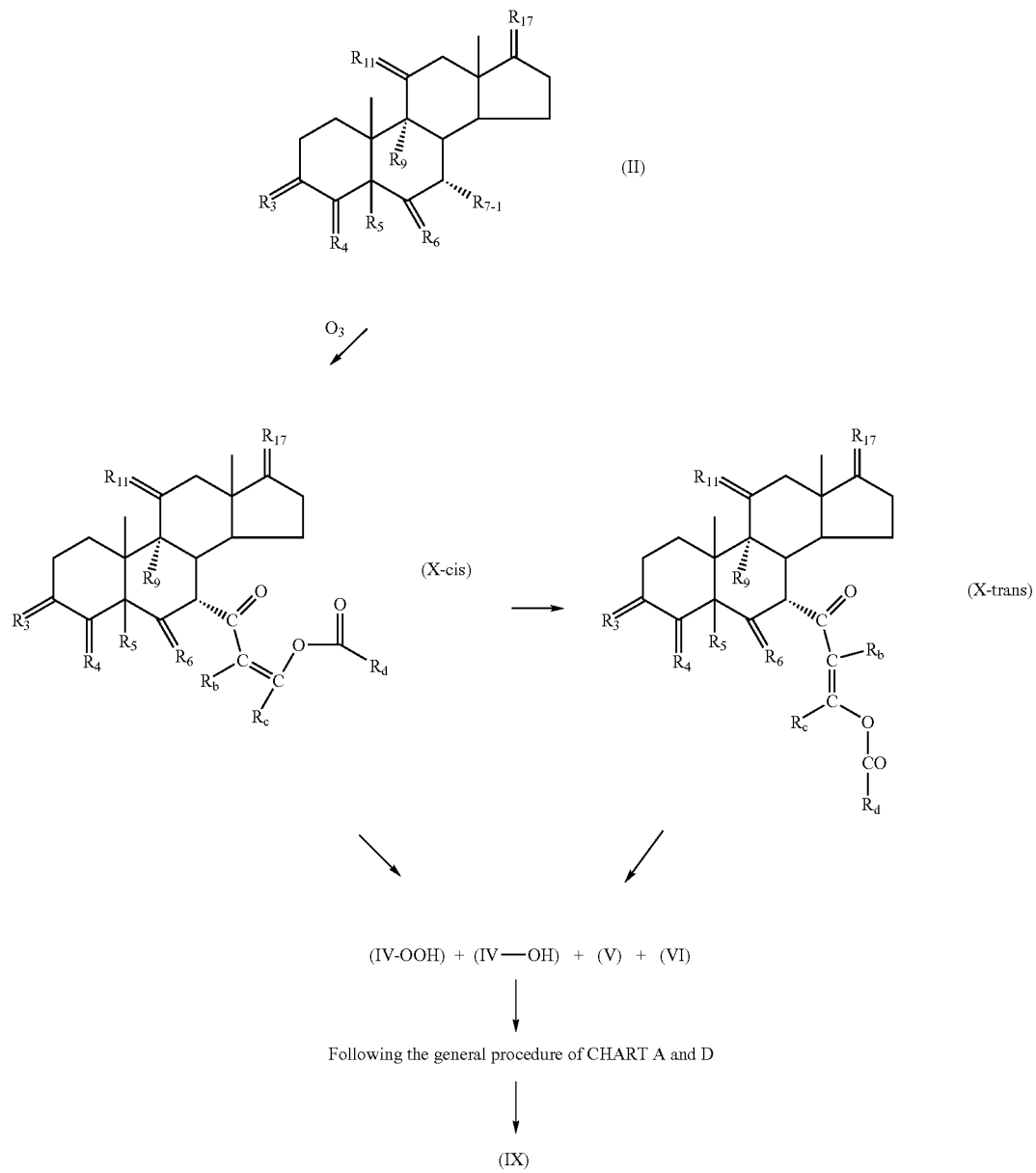
CHART D
When R<sub>7-1</sub> is (—A1)
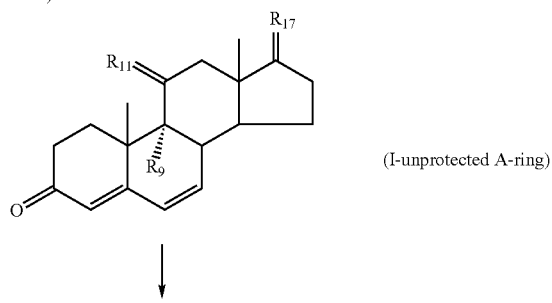

-continued
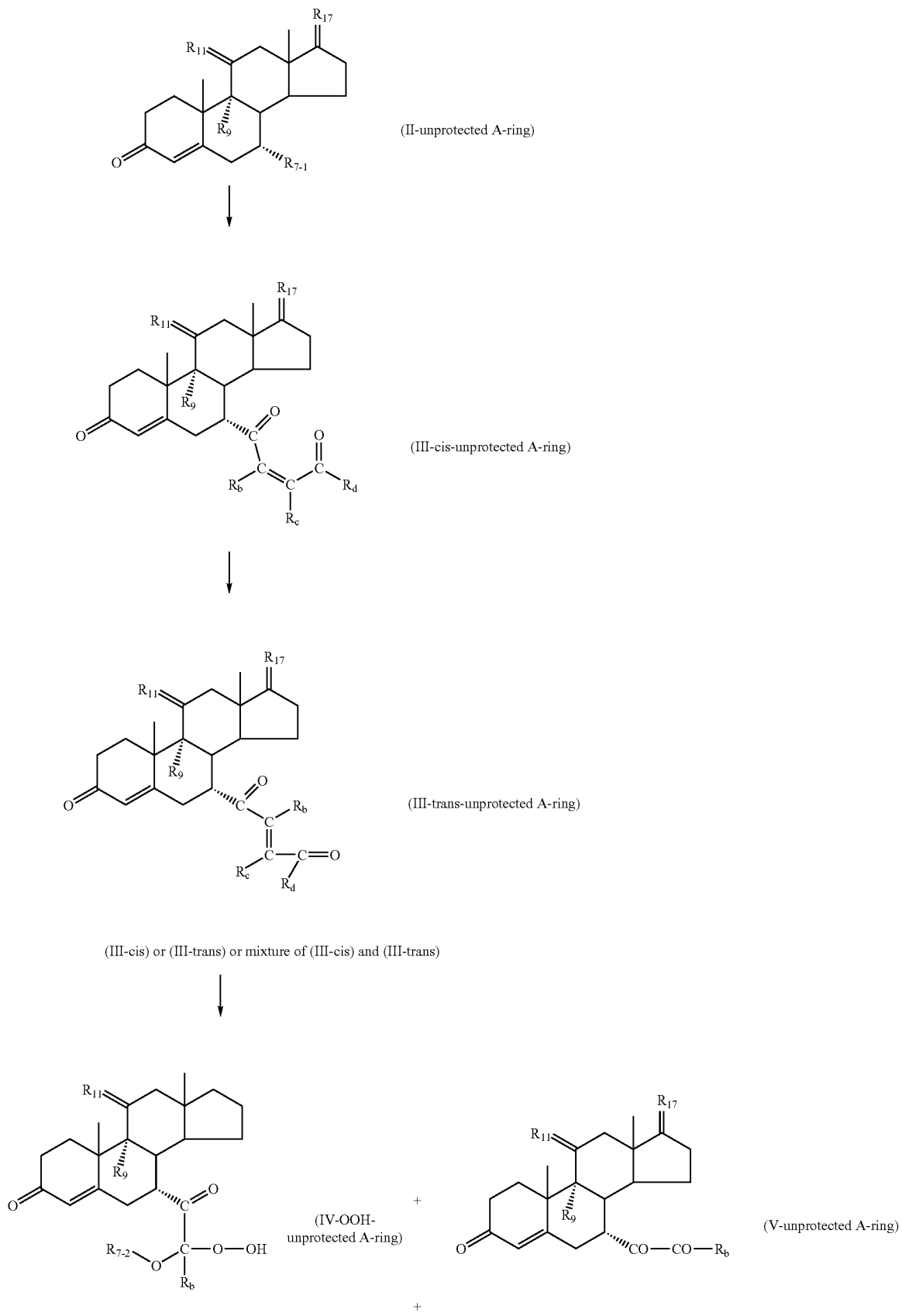
(II-unprotected A-ring)
(III-cis-unprotected A-ring)
(III-trans-unprotected A-ring)
(III-cis) or (III-trans) or mixture of (III-cis) and (III-trans)
(IV-OOH-unprotected A-ring)
(V-unprotected A-ring)

-continued
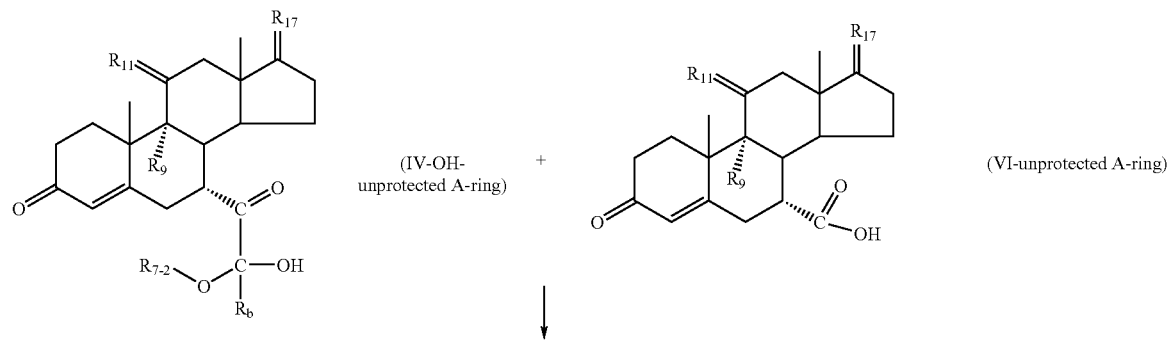
(IV-OH-unprotected A-ring) + (VI-unprotected A-ring)
(IV-OH-unprotected A-ring) + (V-unprotected A-ring) + (VI-unprotected A-ring)
(IV-OH-unprotected A-ring) + (V-unprotected A-ring)
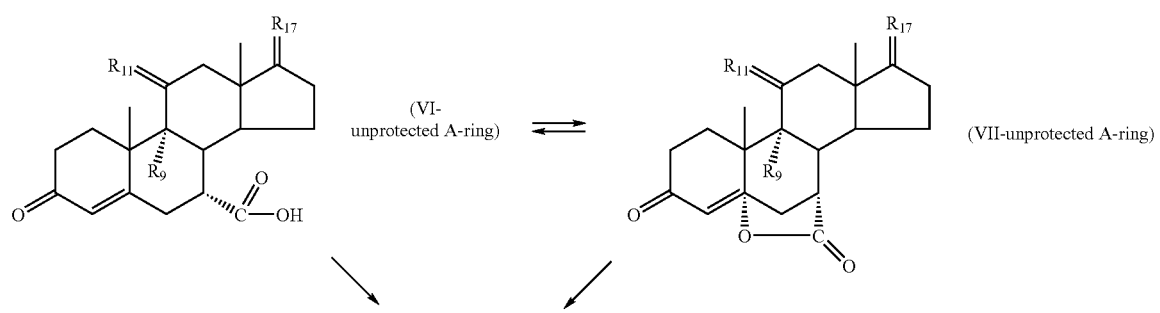
(VI-unprotected A-ring) ⇌ (VII-unprotected A-ring)
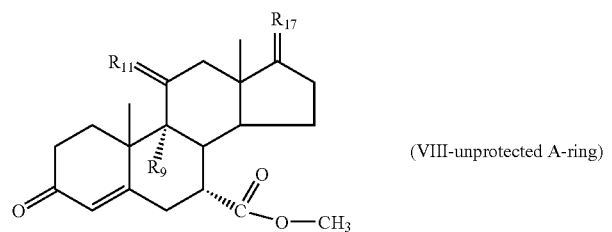
(VIII-unprotected A-ring)
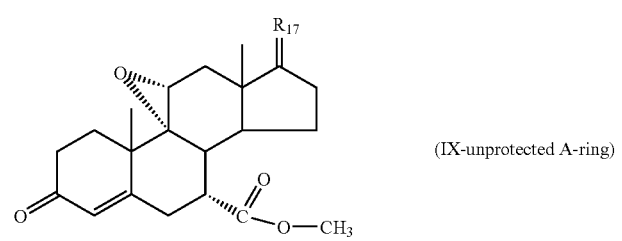
(IX-unprotected A-ring)

CHART E
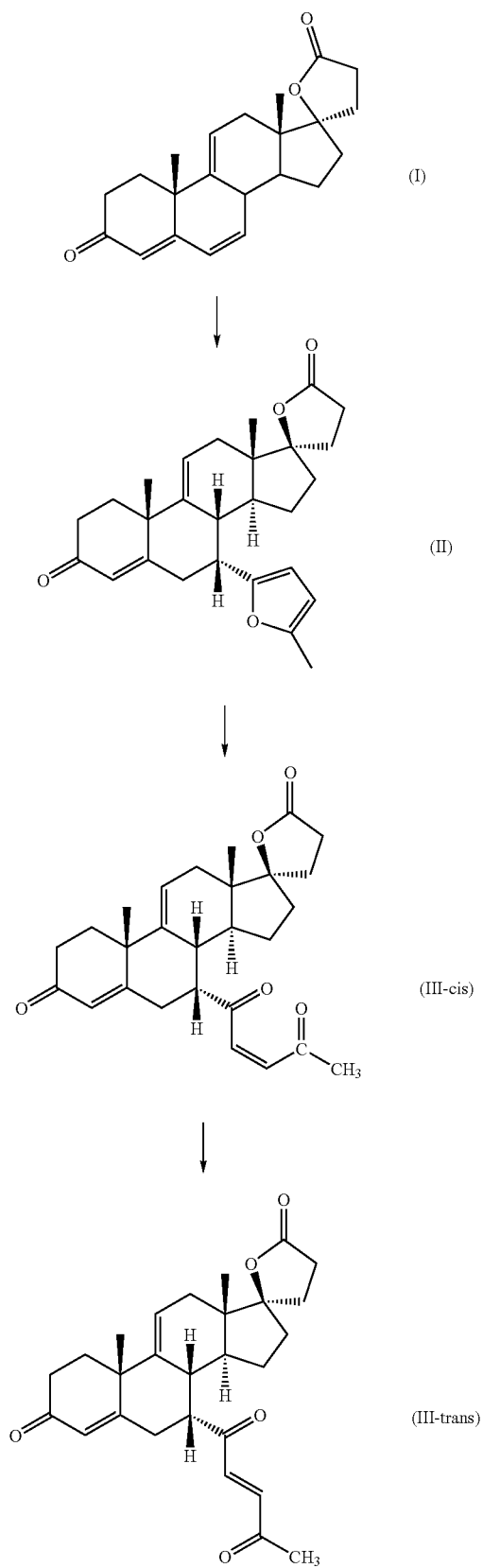

-continued
(III-cis) or (III-trans) or mixture of (III-cis) or (III-trans)
↓
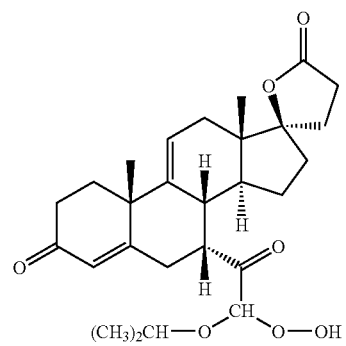 (IV-OOH)
+
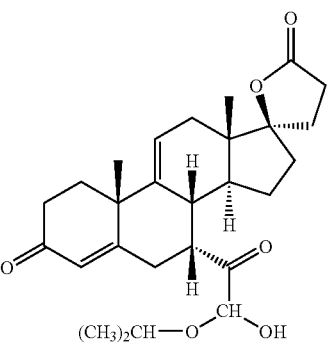 (IV-OH)
+
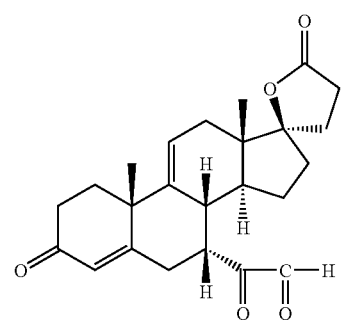 (V)
+
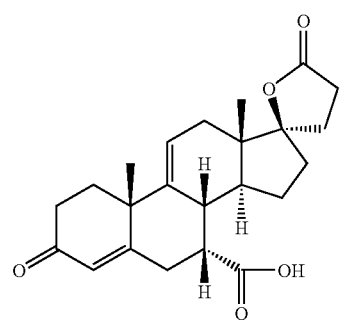 (VI)
↓
(IV-OH) + (V) + (VI)
(IV-OH) + (V)
↙
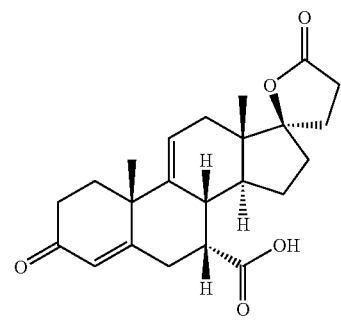 (VI) ⇌ 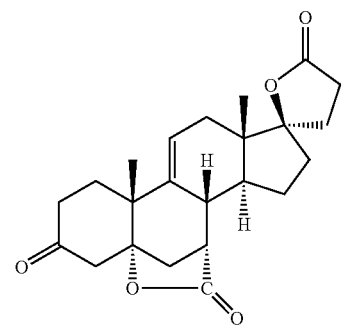 (VII)
↙ ↙

-continued
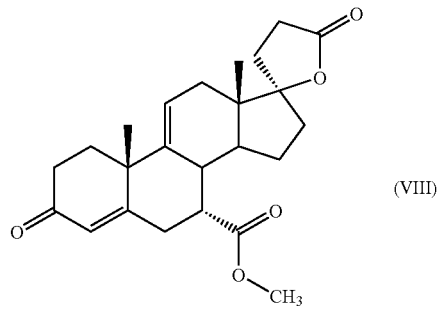
(VIII)
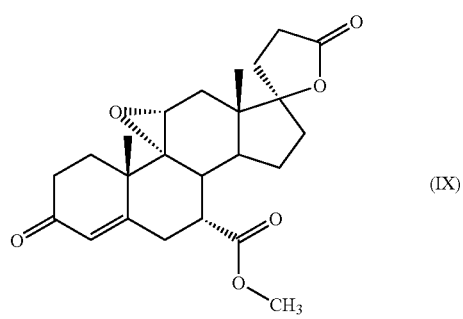
(IX)
CHART F
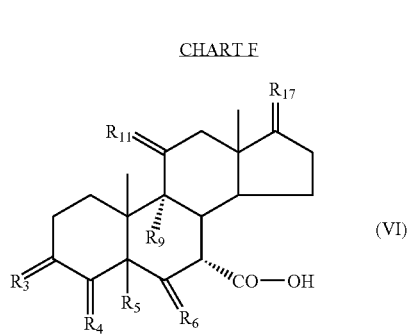
(VI)
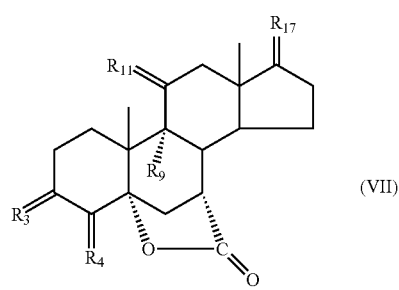
(VII)
-continued
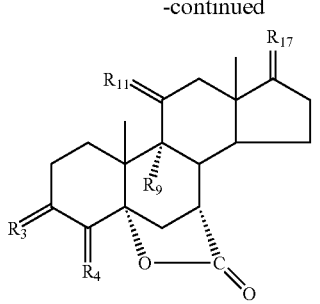
(VII)
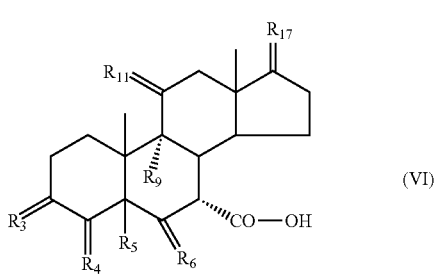
(VI)

CHART G
When R$_{7-1}$ is (—A2)
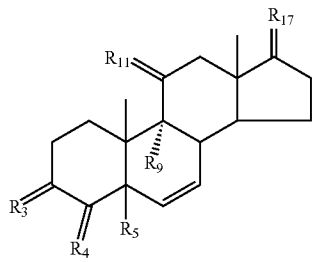
(I)
↓
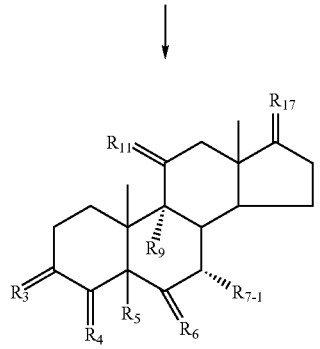
(II)
↓
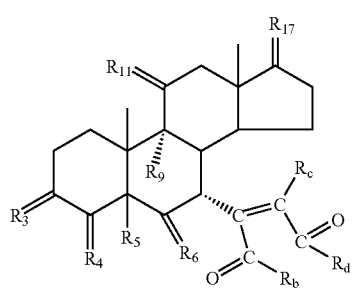
(XIV)
↓
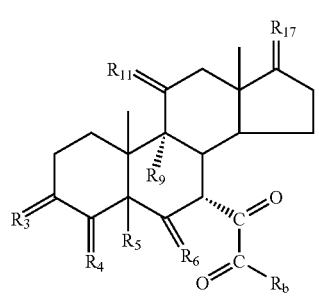
(XV)
↓
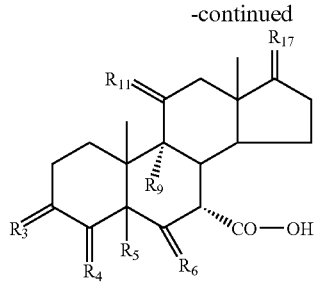
(VI)
CHART H
When R$_{7-1}$ is (—B), (—C) or (—D1, —D2, —D3)
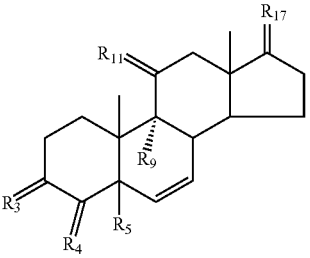
(I)
↓
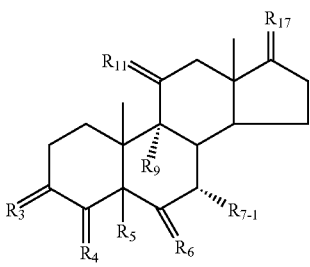
(II)
↓
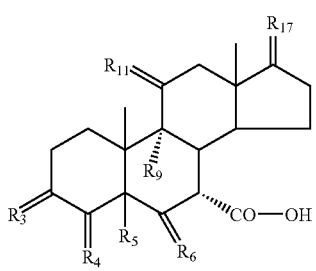
(VI)

CHART I
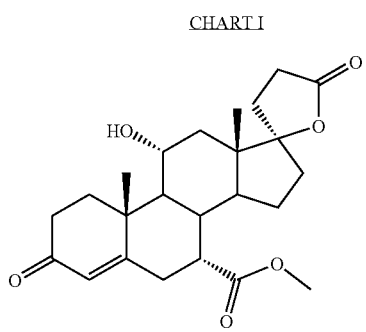
(CI)
↓
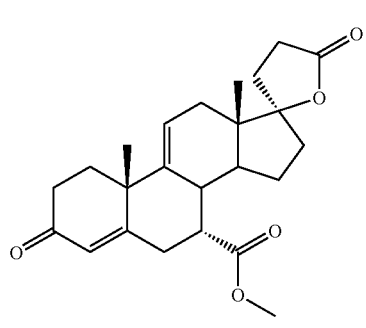
(CII)
↓
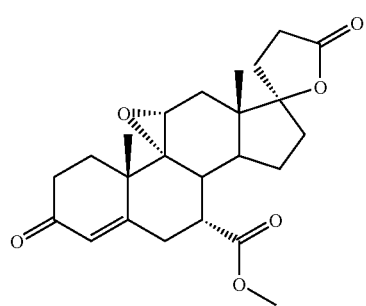
(CIII)
CHART J
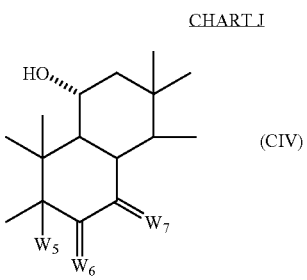
(CIV)
↓
-continued
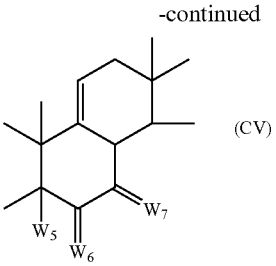
(CV)
CHART K
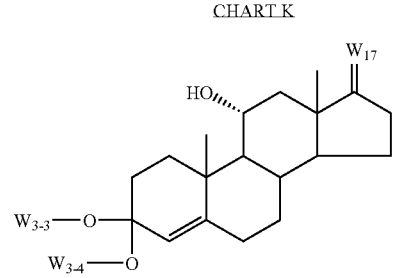
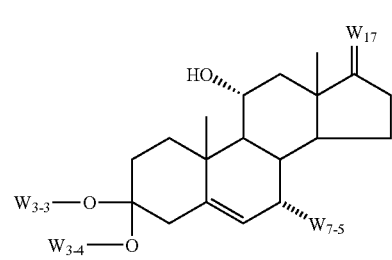
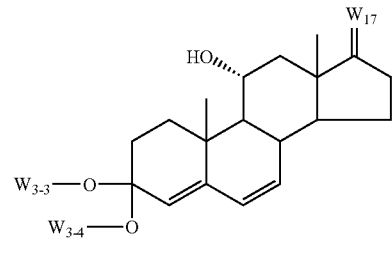
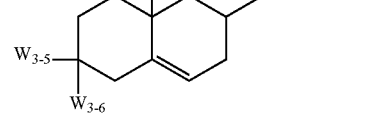
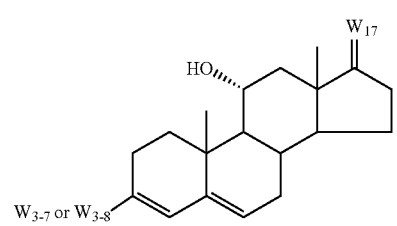

-continued
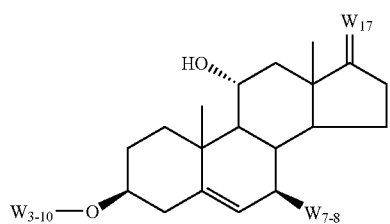
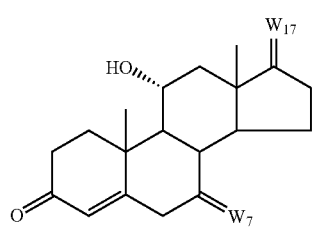
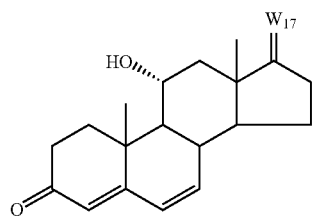
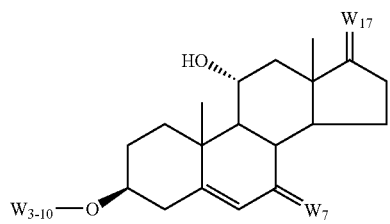
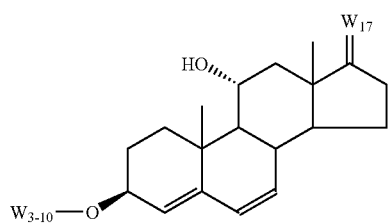
-continued
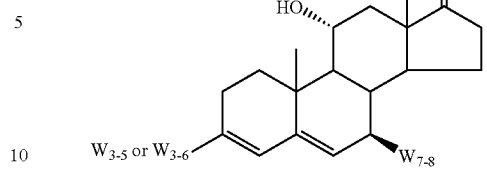
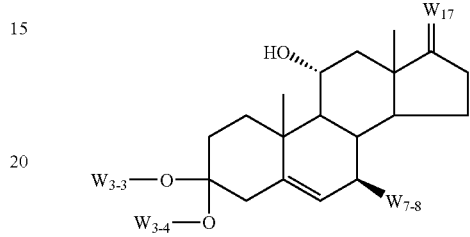
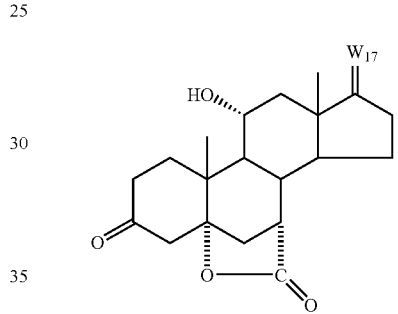
CHART L
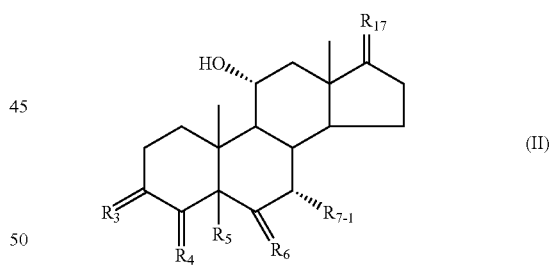
(II)
↓ Ishikawa Reagent
or
$(CH_3)_2N-CF_2-CF_2-H$
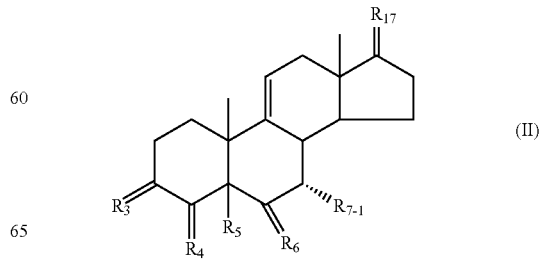
(II)

CHART M
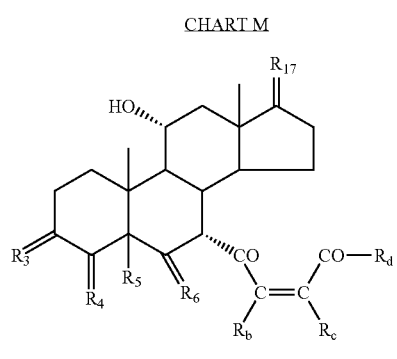
(III-cis)
or
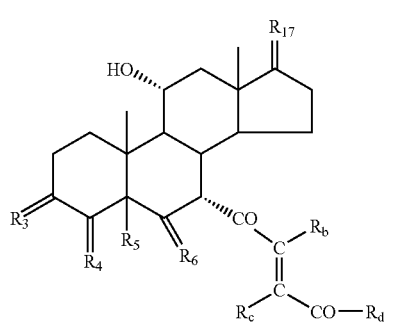
(III-trans)
↓ Ishikawa Reagent
or
$(CH_3)_2N-CF_2-CF_2-H$
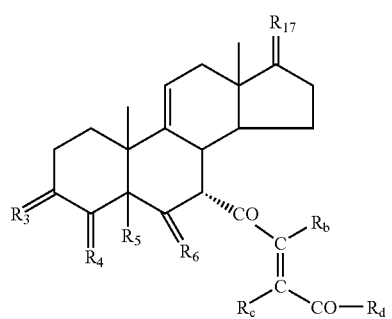
(III-trans)
CHART N
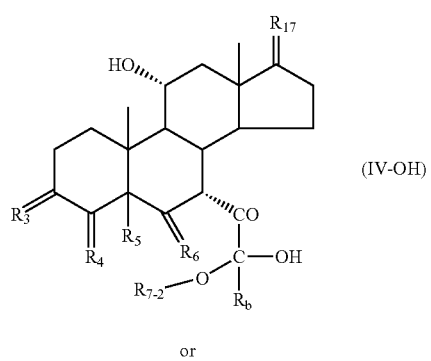
(IV-OH)
or
-continued
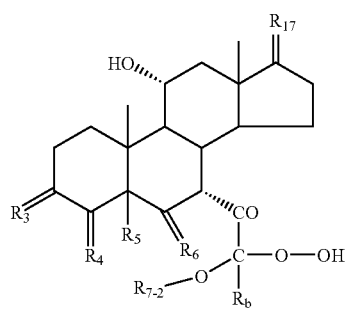
(IV-OOH)
or
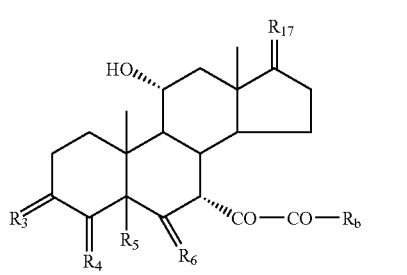
(V)
↓ Ishikawa Reagent
or
$(CH_3)_2N-CF_2-CF_2-H$
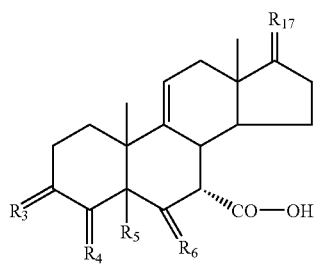
(VI)
CHART O
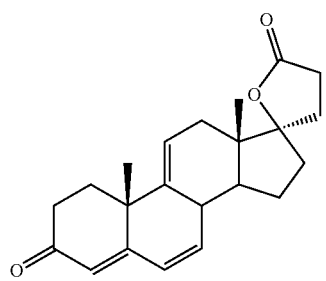
(I)
↓
2-methylfuran
absolute ethanol
boron trifluoride etherate
↓

-continued
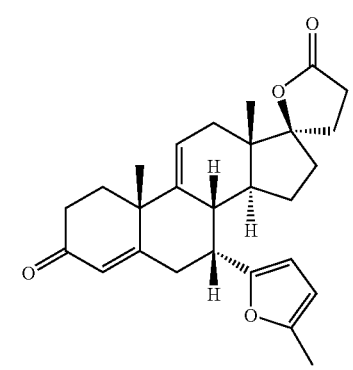
(II)
diboromatin
acetate
aqueous hydrochloric acid
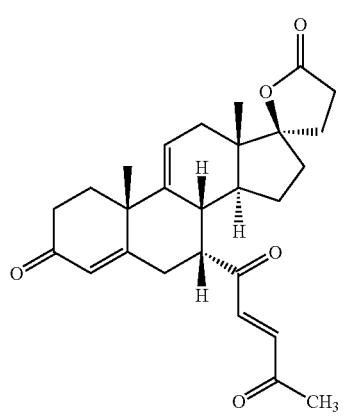
(III-trans)
ozone
dimethylsulfide
hydrogen peroxide
bicarbonate
-continued
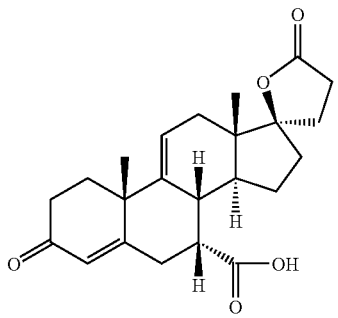
(VI)
p-toluenesulfonic acid
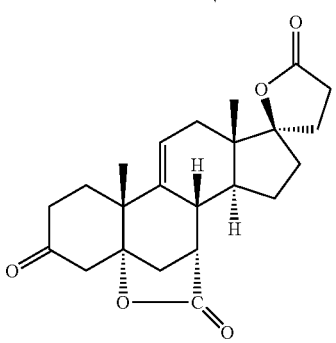
(VII)
bicarbonate, dimethylsulfate
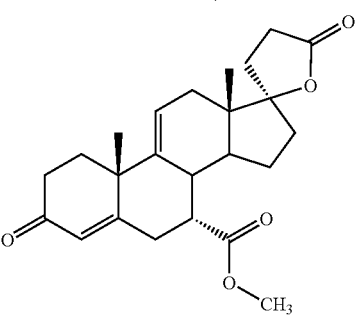
(VIII)
tricholoroacetamide/hydrogen peroxide
ethanol
methyl ethyl ketone

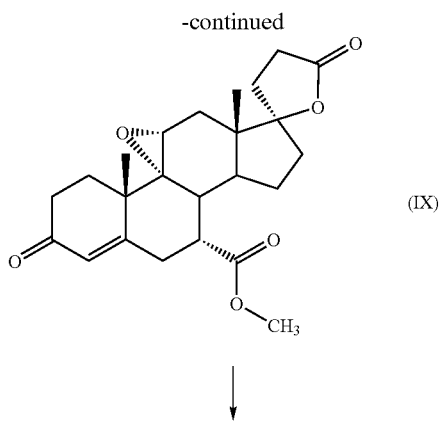

The invention claimed is:
1. A compound of the formula

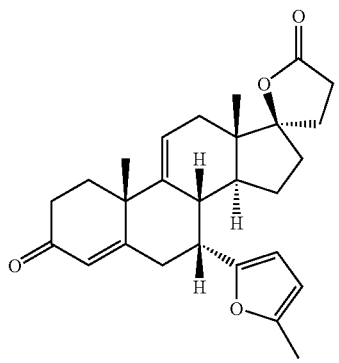

in crystalline form having a powder X-ray diffraction spectrum with a peak at about 14.2±0.2 degrees two theta.

2. The compound according to claim 1 having an X-ray powder diffraction pattern with peaks at about 10.6±0.2, about 14.2±0.2, and about 17.8±0.2 degrees two theta.

3. The compound according to claim 2 having an X-ray powder diffraction pattern spectrum of
Two-Theta Angle (°) with a range of

| From about | To about |
|---|---|
| 6.46 | 6.59 |
| 10.46 | 10.70 |
| 11.48 | 11.70 |
| 12.55 | 12.79 |
| 14.19 | 14.36 |
| 15.06 | 15.30 |
| 16.10 | 16.65 |
| 16.55 | 16.74 |
| 17.79 | 18.01 |
| 18.25 | 18.46 |
| 19.46 | 19.70 |
| 20.06 | 20.30 |
| 20.86 | 21.25 |
| 21.60 | 21.80 |
| 23.14 | 23.35 |
| 24.74 | 24.95 |
| 25.15 | 25.96 |
| 25.85 | 26.05 |
| 27.35 | 27.55 |
| 28.26 | 28.90 |
| 28.75 | 28.85 |
| 29.91 | 30.14 |
| 30.90 | 31.10 |
| 31.86 | 32.05 |
| 32.59 | 32.79 |
| 33.14 | 33.89 |
| 33.63 | 34.00 |
| 34.27 | 34.49 |
| 35.52 | 35.75 |
| 36.06 | 36.30 |
| 37.02 | 37.21 |
| 37.74 | 37.91 |
| 38.42 | 38.64 |
| 39.35 | 39.39 | where
Two-Theta Angle is measured in degrees.

4. The compound according to claim 2 having an average powder X-ray diffraction spectrum of about:

| Two-Theta Angle (°) average |
|---|
| 6.53 |
| 10.59 |
| 11.58 |
| 12.68 |
| 14.28 |
| 15.18 |
| 16.35 |
| 16.64 |
| 17.90 |
| 18.38 |
| 19.58 |
| 20.17 |
| 21.05 |
| 21.71 |
| 23.25 |
| 24.82 |
| 25.32 |
| 25.95 |
| 27.45 |
| 28.44 |
| 28.80 |
| 30.01 |
| 31.00 |
| 31.97 |
| 32.69 |
| 33.32 |
| 33.80 |
| 34.37 |
| 35.65 |
| 36.17 |
| 37.12 |
| 37.83 |
| 38.53 |
| 39.37. |

5. The compound according to claim 2 having an X-ray powder diffraction pattern spectrum of:
Two-Theta Angle (°) and Relative Intensity (%) with ranges of

| Two-Theta Angle (°) | | Relative Intensity (%) | |
|---|---|---|---|
| From about | To about | From about | To about |
| 6.46 | 6.59 | 1.0 | 1.6 |
| 10.46 | 10.70 | 10.7 | 58.3 |

-continued

| Two-Theta Angle (°) | | Relative Intensity (%) | |
|---|---|---|---|
| From about | To about | From about | To about |
| 11.48 | 11.70 | 11.7 | 20.8 |
| 12.55 | 12.79 | 2.2 | 4.2 |
| 14.19 | 14.36 | 14.4 | 100.0 |
| 15.06 | 15.30 | 15.3 | 29.5 |
| 16.10 | 16.65 | 7.2 | 50.3 |
| 16.55 | 16.74 | 16.7 | 66.4 |
| 17.79 | 18.01 | 18.0 | 100.0 |
| 18.25 | 18.46 | 18.5 | 34.5 |
| 19.46 | 19.70 | 6.1 | 12.6 |
| 20.06 | 20.30 | 19.5 | 28.1 |
| 20.86 | 21.25 | 16.1 | 36.3 |
| 21.60 | 21.80 | 10.8 | 20.0 |
| 23.14 | 23.35 | 23.3 | 48.0 |
| 24.74 | 24.95 | 11.5 | 19.0 |
| 25.15 | 25.96 | 4.4 | 30.3 |
| 25.85 | 26.05 | 12.1 | 31.2 |
| 27.35 | 27.55 | 9.5 | 22.7 |
| 28.26 | 28.90 | 2.1 | 6.2 |
| 28.75 | 28.85 | 6.6 | 11.1 |
| 29.91 | 30.14 | 1.9 | 3.5 |
| 30.90 | 31.30 | 5.6 | 10.4 |
| 31.86 | 32.05 | 1.2 | 3.7 |
| 32.59 | 32.79 | 0.9 | 2.3 |
| 33.14 | 33.89 | 1.6 | 4.5 |
| 33.63 | 34.00 | 1.1 | 4.9 |
| 34.27 | 34.49 | 1.4 | 2.2 |
| 35.52 | 35.75 | 1.3 | 3.9 |
| 36.06 | 36.30 | 7.9 | 27.0 |
| 37.02 | 37.21 | 3.9 | 6.2 |
| 37.74 | 37.91 | 1.0 | 2.2 |
| 38.42 | 38.64 | 1.2 | 2.9 |
| 39.35 | 39.39 | 1.6 | 1.8 | where

Two-Theta Angle is measured in degrees and

Relative Intensity is the intensity percentage of each peak relative to the strongest peak.

6. The compound according to claim 2 having an average X-ray powder diffraction pattern spectrum of about and an average Relative Intensity of about:

| Two-Theta Angle (°) average | Relative Intensity (%) average |
|---|---|
| 6.53 | 1.3 |
| 10.59 | 40.9 |
| 11.58 | 15.9 |
| 12.68 | 2.9 |
| 14.28 | 98.2 |
| 15.18 | 26.1 |
| 16.35 | 18.7 |
| 16.64 | 40.3 |
| 17.90 | 62.9 |
| 18.38 | 27.7 |
| 19.58 | 9.4 |
| 20.17 | 23.8 |
| 21.05 | 25.1 |
| 21.71 | 15.6 |
| 23.25 | 36.4 |
| 24.82 | 13.5 |
| 25.32 | 8.4 |
| 25.95 | 23.1 |
| 27.45 | 17.0 |
| 28.44 | 3.8 |
| 28.80 | 8.5 |
| 30.01 | 2.5 |
| 31.00 | 7.9 |
| 31.97 | 2.5 |
| 32.69 | 1.7 |
| 33.32 | 3.4 |
| 33.80 | 2.7 |
| 34.37 | 1.7 |
| 35.65 | 2.5 |
| 36.1 | 15.3 |
| 37.12 | 4.8 |
| 37.83 | 1.6 |
| 38.53 | 2.3 |
| 39.37 | 1.7. |

7. The compound according to claim 2 having an X-ray powder diffraction pattern spectrum of:

| Two-Theta Angle (°) | | d-spacing (Å) | | Relative Intensity (%) | |
|---|---|---|---|---|---|
| From About | To About | From About | To About | From About | To About |
| 6.46 | 6.59 | 13.39 | 13.66 | 1.0 | 1.6 |
| 10.46 | 10.70 | 8.26 | 8.45 | 10.7 | 58.3 |
| 11.48 | 11.70 | 7.56 | 7.70 | 11.7 | 20.8 |
| 12.55 | 12.79 | 6.92 | 7.05 | 2.2 | 4.2 |
| 14.19 | 14.36 | 6.16 | 6.24 | 14.4 | 100.0 |
| 15.06 | 15.30 | 5.79 | 5.88 | 15.3 | 29.5 |
| 16.10 | 16.65 | 5.32 | 5.50 | 7.2 | 50.3 |
| 16.55 | 16.74 | 5.29 | 5.35 | 16.7 | 66.4 |
| 17.79 | 18.01 | 4.92 | 4.98 | 18.0 | 100.0 |
| 18.25 | 18.46 | 4.80 | 4.86 | 18.5 | 34.5 |
| 19.46 | 19.70 | 4.50 | 4.56 | 6.1 | 12.6 |
| 20.06 | 20.30 | 4.37 | 4.42 | 19.5 | 28.1 |
| 20.86 | 21.25 | 4.18 | 4.26 | 16.1 | 36.3 |
| 21.60 | 21.80 | 4.07 | 4.11 | 10.8 | 20.0 |
| 23.14 | 23.35 | 3.81 | 3.84 | 23.3 | 48.0 |
| 24.74 | 24.95 | 3.57 | 3.60 | 11.5 | 19.0 |
| 25.15 | 25.96 | 3.43 | 3.54 | 4.4 | 30.3 |
| 25.85 | 26.05 | 3.42 | 3.44 | 12.1 | 31.2 |
| 27.35 | 27.55 | 3.24 | 3.26 | 9.5 | 22.7 |
| 28.26 | 28.90 | 3.09 | 3.16 | 2.1 | 6.2 |
| 28.75 | 28.85 | 3.09 | 3.10 | 6.6 | 11.1 |
| 29.91 | 30.14 | 2.96 | 2.98 | 1.9 | 3.5 |
| 30.90 | 31.10 | 2.87 | 2.89 | 5.6 | 10.4 |
| 31.86 | 32.05 | 2.79 | 2.81 | 1.2 | 3.7 |
| 32.59 | 32.79 | 2.73 | 2.75 | 0.9 | 2.3 |
| 33.14 | 33.89 | 2.64 | 2.70 | 1.6 | 4.5 |
| 33.63 | 34.00 | 2.63 | 2.66 | 1.1 | 4.9 |
| 34.27 | 34.49 | 2.60 | 2.61 | 1.4 | 2.2 |
| 35.52 | 35.75 | 2.51 | 2.53 | 1.3 | 3.9 |
| 36.06 | 36.30 | 2.47 | 2.49 | 7.9 | 27.0 |
| 37.02 | 37.21 | 2.41 | 2.43 | 3.9 | 6.2 |
| 37.74 | 37.91 | 2.37 | 2.38 | 1.0 | 2.2 |
| 38.42 | 38.64 | 2.33 | 2.34 | 1.2 | 2.9 |
| 39.35 | 39.39 | 2.29 | 2.29 | 1.6 | 1.8 | where

Two-Theta Angle is measured in degrees, d-Spacing is measured in angstroms, and

Relative Intensity is the intensity percentage of each peak relative to the strongest peak.

8. The compound according to claim 2 having a average powder X-ray diffraction pattern spectrum of about, an average d-Spacing of about and an average Relative Intensity of about:

| Two-Theta Angle (°) average | d-spacing (Å) average | Relative Intensity (%) average |
|---|---|---|
| 6.53 | 13.52 | 1.3 |
| 10.59 | 8.35 | 40.9 |
| 11.58 | 7.63 | 15.9 |

-continued

| Two-Theta Angle (°) average | d-spacing (Å) average | Relative Intensity (%) average |
|---|---|---|
| 12.68 | 6.98 | 2.9 |
| 14.28 | 6.20 | 98.2 |
| 15.18 | 5.83 | 26.1 |
| 16.35 | 5.42 | 18.7 |
| 16.64 | 5.32 | 40.3 |
| 17.90 | 4.95 | 62.9 |
| 18.38 | 4.82 | 27.7 |
| 19.58 | 4.53 | 9.4 |
| 20.17 | 4.40 | 23.8 |
| 21.05 | 4.22 | 25.1 |
| 21.71 | 4.09 | 15.6 |
| 23.25 | 3.82 | 36.4 |
| 24.82 | 3.58 | 13.5 |
| 25.32 | 3.51 | 8.4 |
| 25.95 | 3.43 | 23.1 |
| 27.45 | 3.25 | 17.0 |
| 28.44 | 3.14 | 3.8 |
| 28.80 | 3.10 | 8.5 |

-continued

| Two-Theta Angle (°) average | d-spacing (Å) average | Relative Intensity (%) average |
|---|---|---|
| 30.01 | 2.98 | 2.5 |
| 31.00 | 2.88 | 7.9 |
| 31.97 | 2.80 | 2.5 |
| 32.69 | 2.74 | 1.7 |
| 33.32 | 2.69 | 3.4 |
| 33.80 | 2.65 | 2.7 |
| 34.37 | 2.61 | 1.7 |
| 35.65 | 2.52 | 2.5 |
| 36.1 | 2.48 | 15.3 |
| 37.12 | 2.42 | 4.8 |
| 37.83 | 2.38 | 1.6 |
| 38.53 | 2.33 | 2.3 |
| 39.37 | 2.29 | 1.7. |

* * * * *